US006358696B1

(12) United States Patent
McBurney

(10) Patent No.: US 6,358,696 B1
(45) Date of Patent: Mar. 19, 2002

(54) METHODS OF TREATMENT OF EYE TRAUMA AND DISORDERS

(76) Inventor: Robert N. McBurney, 20 Leslie Rd., Newton, MA (US) 02158

( * ) Notice: Subject to any disclaimer, the term of this patent is extended or adjusted under 35 U.S.C. 154(b) by 0 days.

(21) Appl. No.: 09/635,309

(22) Filed: Aug. 9, 2000

Related U.S. Application Data

(63) Continuation of application No. 08/686,494, filed on Jul. 25, 1996, now Pat. No. 6,242,198.

(51) Int. Cl.$^7$ ...................... G01N 33/53; C07C 277/00; C07D 311/02; A61F 2/00
(52) U.S. Cl. ...................... 435/7.2; 564/238; 549/288; 424/427
(58) Field of Search .................. 435/7.2; 564/238; 549/288; 424/427

(56) References Cited

U.S. PATENT DOCUMENTS

| 2,633,474 A | 3/1953 | Beaver | 260/565 |
|---|---|---|---|
| 2,704,710 A | 3/1955 | Sprung | 95/2 |

(List continued on next page.)

FOREIGN PATENT DOCUMENTS

| CA | 1081711 | 7/1980 |
|---|---|---|
| DE | 3108564 | 11/1982 |
| EP | 0 035 374 | 9/1981 |
| EP | 0 179 642 | 4/1986 |
| EP | 0 235 942 | 9/1987 |
| EP | 0 266 574 | 5/1988 |
| EP | 0 296 560 | 12/1988 |
| EP | 0 372 934 | 6/1990 |
| EP | 0 501 552 | 9/1992 |
| GB | 966493 | 8/1964 |
| WO | WO 90/14067 | 11/1990 |
| WO | WO 92/19621 | 11/1992 |
| WO | WO 94/22807 | 10/1994 |
| WO | WO 94/27591 | 12/1994 |
| WO | WO 95/14467 | 6/1995 |
| WO | WO 95/20950 | 8/1995 |
| WO | WO 96/17612 | 6/1996 |
| ZA | 92/0990 | 11/1992 |
| ZA | 92/0944 | 10/1993 |
| ZA | 94/9253 | 3/1996 |

OTHER PUBLICATIONS

J. Mosinger et al., *Experimental Neurology*, 113:10–17 (1991).
Y. Yoon et al., *Arch. Ophthalmol.*, 107:409–411 (1989).
L. Gupta et al., *Arch. Ophthalmol.*, 111:384–388 (1993).
Doull et al., A Survey of Compounds for Radiation Protection (USAF Radiation Laboratory).
Database Crossfire, Beilsteninformationsysteme GmbH, BRN 3095078, 3094377, 3093029, *J. Org. Chem. USSR*, 4:459 (1968).
Database Crossfire, Beilsteninformationsysteme GmbH, BRN 2938786, *Curr. Sci.*, 45:764 (1976).
Database Crossfire, Beilsteninformationsysteme GmbH, BRN 3430469, *Yuki Gosei Kaguku Kukaisha*, 8:38,42 (1950).
K. Miura et al., *Chem. Abstracts*, 109:114, 75454d (1988).
P. Vasilev et al., *Chem. Abstracts*, 93:150095u (1980).
S. Ahmad, *Chem. Abstracts*, 108:538, 221382b (1988).
A. Ginsburg et al., *Chem. Abstracts*, 57:4518d (1962).
G. Durant et al., *J. Med. Chem.*, 9:22–27 (1966).
C. Kroger et al., *Ber.*, 97:396–404 (1964).
E. Podrebarac et al., *J. Med. Chem.*, 6:283–288 (1963).
R. Prasad, *Can. J. Chem.*, 45:2247–2252 (1967).
D. Lloyd et al., *Tetrahedron*, 33:1379–1389 (1977).
H. Shimazu et al., *Chem. Abstracts*, 111(2):16337m (1989).
T. Tada et., *Chem. Abstracts*, 104(24):208252g (1986).
L. Kiselev et al., *Chem. Abstracts*, 91(21):175291b (1979).
A. Heesing et al., *Chem. Abstracts*, 64(11):15776h (1966).
K. Akiba et al., *Bull. Chem. Soc. Jap.*, 47(4):935–937 (1974).
Database Rtecs, "National Institute of Occupational Safety and Health", RTECS No. MF735000.
J. Keana et al., *Proc. Natl. Acad. Sci.*, 86:5631–5635 (1989).
S. Siddique et al., *Pakistan journal of Scientific and Industrial Res.*, 30(3):163–181 (1987).
E. Maida et al., *Winer Klinische Wochenschrift*, 90(2):43–48 (1978).
C. Chavkin et al., *Advances in the Biosciences*, 75407–410 (1989).
P. Bhargava et al., *Chem. Abstracts*, 86:598, 189787b (1977).
H. Geluk et al., *J. Med. Chem.*, 12:712–715 (1969).
M. Scherz et al., *J. Med. Chem.*, 33:2421–2429 (1990).
A. Stolyarchuk et al., *Chem. Abstracts*, 86:522–523, 121071h (1977).
T. Weakley et al., *Acta. Cryst.*, 46:2234–2236 (1990).
J. Adams et al., *Eur. J. Pharm.*, 142:61–71 (1987).
B. Campbell et al., *J. Neurosci.*, 9:3380–3391 (1989).
G. Durant et al., *J. Med. Chem.*, 28:1414–1422 (1985).
B. Tester et al., *Society for Neuroscience*, 19$^{th}$ Annual Meeting, 983, 396.17 (1989).
M. Kavanaugh et al., *Proc. Natl. Acad. Sci. USA*, 85:2844–2848 (1988).
E. Weber et al., *Proc. Natl. Acad. Sci. USA*, 83:8784–8788 91986).
C. Maryanoff et al., *J. Org. Chem.*, 51:1882–1884 (1986).
S. Safir et al., *J. Org. Chem.*, 13:924–932 (1948).
F. Sharp et al., *Society for Neuroscience Abstr.*, vol. 18, Abstr. No. 482.3 (1992).
B. Clement et al., *Xenobiotica*, 23(2):155–167 (1993).
Kiselev et al., *Chem. Abstracts*, vol. 66 (1967).

Primary Examiner—Hankyel T. Park
(74) Attorney, Agent, or Firm—David G. Conlin; Peter F. Corless; Edwards & Angell, LLP

(57) ABSTRACT

Methods are provided for treatment of eye disorders and injury, including methods for treatment of reduced flow of blood or other nutrients to retinal tissue and/or optic nerve, methods for treatment of retinal ischemia and trauma and methods for treatment for optic nerve injury/damage.

33 Claims, No Drawings

U.S. PATENT DOCUMENTS

| | | | |
|---|---|---|---|
| 3,119,831 A | 1/1964 | Homer | 260/296 |
| 3,121,645 A | 2/1964 | Bindler et al. | 117/138.5 |
| 3,122,555 A | 2/1964 | Janssen | 260/292.4 |
| 3,140,231 A | 7/1964 | Luskin et al. | 167/65 |
| 3,159,676 A | 12/1964 | Spickett et al. | 260/564 |
| 3,168,562 A | 2/1965 | Walton et al. | 260/564 |
| 3,200,151 A | 8/1965 | Spickett et al. | 260/564 |
| 3,228,975 A | 1/1966 | Abraham et al. | 260/501 |
| 3,248,426 A | 4/1966 | Dvornil | 260/564 |
| 3,252,861 A | 5/1966 | Mull | 167/65 |
| 3,256,278 A | 6/1966 | Petracek | 260/247.5 |
| 3,270,054 A | 8/1966 | Gagneux et al. | 260/564 |
| 3,283,003 A | 11/1966 | Jack et al. | 260/564 |
| 3,284,289 A | 11/1966 | Duerr et al. | 167/30 |
| 3,301,755 A | 1/1967 | Mull | 167/65 |
| 3,305,552 A | 2/1967 | Cragoe, Jr. et al. | 260/250 |
| 3,320,229 A | 5/1967 | Szabo et al. | 260/96.5 |
| 3,403,156 A | 9/1968 | Humber et al. | 260/286 |
| 3,409,669 A | 11/1968 | Dyke | 260/564 |
| 3,479,437 A | 11/1969 | Sazabo et al. | 424/304 |
| 3,527,871 A | 9/1970 | Engelhardt et al. | 424/330 |
| 3,547,951 A | 12/1970 | Hardie et al. | 260/340.9 |
| 3,597,433 A | 8/1971 | Dobson et al. | 260/286 R |
| 3,624,259 A | 11/1971 | Galantay | 260/479 R |
| 3,639,477 A | 2/1972 | L'Italien | 260/564 A |
| 3,678,109 A | 7/1972 | Knowles | 260/564 R |
| 3,681,459 A | 8/1972 | Hughes et al. | 260/565 |
| 3,689,675 A | 9/1972 | Knowles | 424/258 |
| 3,723,463 A | 3/1973 | Yale et al. | 260/327 B |
| 3,804,898 A | 4/1974 | Panneman | 260/564 A |
| 3,812,119 A | 5/1974 | Walker | 260/247 |
| 3,822,262 A | 7/1974 | Bream et al. | 260/256.4 H |
| 3,888,927 A | 6/1975 | Hamakawa et al. | 260/564 R |
| 3,903,163 A | 9/1975 | McCarthy, Jr. | 260/564 R |
| 3,906,044 A | 9/1975 | Algami et al. | 260/564 R |
| 3,908,013 A | 9/1975 | Hughes et al. | 424/258 |
| 3,914,306 A | 10/1975 | Douglas et al. | 260/562 R |
| 3,949,089 A | 4/1976 | Maxwell et al. | 424/326 |
| 3,965,176 A | 6/1976 | Gold | 260/564 RF |
| 3,968,211 A | 7/1976 | DuCharme | 424/248 |
| 3,972,931 A | 8/1976 | McCarthy, Jr. | 260/564 R |
| 3,975,533 A | 8/1976 | Kodama et al. | 424/326 |
| 3,976,643 A | 8/1976 | Diamond et al. | 260/247.5 R |
| 3,976,787 A | 8/1976 | Hughes et al. | 424/326 |
| 3,983,250 A | 9/1976 | Abdallah et al. | 424/326 |
| 3,987,158 A | 10/1976 | Hodson | 424/9 |
| 3,988,474 A | 10/1976 | Abdallah et al. | 424/326 |
| 4,014,934 A | 3/1977 | Hughes et al. | 260/565 |
| 4,051,256 A | 9/1977 | Swallow | 424/304 |
| 4,052,455 A | 10/1977 | Matier et al. | 260/562 R |
| 4,052,508 A | 10/1977 | Anderson et al. | 424/258 |
| 4,060,640 A | 11/1977 | Kodama et al. | 424/326 |
| 4,064,139 A | 12/1977 | Anderson et al. | 260/313.1 |
| 4,093,655 A | 6/1978 | Miller et al. | 260/564 RF |
| 4,109,014 A | 8/1978 | Liu et al. | 424/326 |
| 4,130,663 A | 12/1978 | Matier et al. | 424/326 |
| 4,134,992 A | 1/1979 | Abdallah et al. | 424/326 |
| 4,154,947 A | 5/1979 | Goldman et al. | 542/417 |
| 4,161,541 A | 7/1979 | Rasmussen | 424/326 |
| 4,284,642 A | 8/1981 | Toldy et al. | 424/273 R |
| 4,318,915 A | 3/1982 | Cohnen et al. | 424/273 R |
| 4,332,822 A | 6/1982 | Ward | 424/324 |
| 4,342,765 A | 8/1982 | Jones et al. | 424/249 |
| 4,353,912 A | 10/1982 | Neumeyer | 424/258 |
| 4,369,325 A | 1/1983 | Toldy et al. | 548/315 |
| 4,374,836 A | 2/1983 | Yellin et al. | 424/251 |
| 4,374,838 A | 2/1983 | Anderson et al. | 424/256 |
| 4,379,160 A | 4/1983 | Harfenist et al. | 424/274 |
| 4,393,077 A | 7/1983 | Douglas et al. | 424/326 |
| 4,400,383 A | 8/1983 | Davidson et al. | 424/250 |
| 4,465,677 A | 8/1984 | DeMarinis et al. | 424/244 |
| 4,470,989 A | 9/1984 | Henning et al. | 424/267 |
| 4,471,137 A | 9/1984 | Barton et al. | 564/240 |
| 4,504,482 A | 3/1985 | Lesher et al. | 514/275 |
| 4,575,514 A | 3/1986 | Carson | 514/542 |
| 4,649,222 A | 3/1987 | Georgiev et al. | 564/459 |
| 4,680,300 A | 7/1987 | Nelson et al. | 514/312 |
| 4,709,094 A | 11/1987 | Weber et al. | 564/238 |
| 4,742,054 A | 5/1988 | Naftchi | 514/215 |
| 4,778,812 A | 10/1988 | Jirkovsky | 514/323 |
| 4,780,466 A | 10/1988 | Hrib et al. | 514/254 |
| 4,789,673 A | 12/1988 | Donatsch et al. | 514/214 |
| 4,833,138 A | 5/1989 | Olney | 514/226.2 |
| 4,837,218 A | 6/1989 | Olney | 514/646 |
| 4,863,953 A | 9/1989 | Leeson et al. | 514/425 |
| 4,866,062 A | 9/1989 | Toth et al. | 514/255 |
| 4,866,076 A | 9/1989 | Gribble | 514/307 |
| 4,873,262 A | 10/1989 | Jung et al. | 514/510 |
| 4,888,347 A | 12/1989 | Woodruff et al. | 514/289 |
| 4,898,978 A | 2/1990 | Bergfeld et al. | 564/231 |
| 4,906,779 A | 3/1990 | Weber et al. | 564/238 |
| 4,918,064 A | 4/1990 | Cordi et al. | 514/114 |
| 4,940,789 A | 7/1990 | Childers, Jr. et al. | 540/581 |
| 4,945,097 A | 7/1990 | Olney | 514/318 |
| 4,962,107 A | 10/1990 | Nakamura et al. | 514/237.5 |
| 4,962,115 A | 10/1990 | Van Daele | 514/326 |
| 5,011,834 A | 4/1991 | Weber et al. | 514/212 |
| 5,089,634 A | 2/1992 | Powers et al. | 549/285 |
| 5,093,525 A | 3/1992 | Weber et al. | 564/238 |
| 5,190,976 A | 3/1993 | Weber et al. | 514/634 |
| 5,231,102 A | 7/1993 | Baker et al. | 514/312 |
| 5,262,568 A | 11/1993 | Weber et al. | 564/238 |
| 5,308,869 A | 5/1994 | Keana et al. | 514/637 |
| 5,312,840 A | 5/1994 | Keana et al. | 514/634 |
| 5,336,689 A | 8/1994 | Weber et al. | 514/634 |
| 5,384,322 A | 1/1995 | Vincent et al. | 514/299 |
| 5,385,946 A | 1/1995 | Keana et al. | 514/634 |
| 5,393,760 A | 2/1995 | Ackermann et al. | 514/323 |
| 5,403,861 A | 4/1995 | Goldin et al. | 514/634 |
| 5,478,863 A | 12/1995 | Keana et al. | 514/634 |
| 5,502,255 A | 3/1996 | Keana et al. | 564/230 |
| 5,507,974 A | 4/1996 | Gompper et al. | 252/299.01 |
| 5,552,443 A | 9/1996 | Keana et al. | 514/631 |
| 5,559,154 A | 9/1996 | Weber et al. | 514/634 |
| 5,604,228 A | 2/1997 | Keana et al. | 514/255 |
| 5,614,630 A | 3/1997 | Goldin et al. | 546/159 |
| 5,622,968 A | 4/1997 | Goldin et al. | 514/313 |
| 5,637,622 A | 6/1997 | Weber et al. | 514/634 |
| 5,637,623 A | 6/1997 | Goldin et al. | 514/634 |
| 5,652,269 A | 7/1997 | Goldin et al. | 514/632 |
| 5,670,519 A | 9/1997 | Goldin et al. | 514/313 |
| 5,672,608 A | 9/1997 | Goldin et al. | 514/313 |
| 5,677,348 A | 10/1997 | Goldin et al. | 514/634 |
| 5,681,861 A | 10/1997 | Goldin et al. | 514/634 |
| 5,686,495 A | 11/1997 | Goldin et al. | 514/632 |
| 5,688,789 A | 11/1997 | Webster et al. | 514/214 |

METHODS OF TREATMENT OF EYE TRAUMA AND DISORDERS

This application is a Continuation of U.S. Ser. No. 08/686,494, filed Jul. 25, 1996, the now U.S. Pat. No. 6,242,198 the teachings of which are incorporated herein by reference.

BACKGROUND OF THE INVENTION

1. Field of the Invention

The present invention relates to use of substituted guanidines and other compounds for use in treatment of eye disease, particularly retinal ischemia and trauma, optic nerve disorders and trauma, and related eye disorders and trauma.

2. Background

Retinal ischemia or degeneration may be produced by injury, tumors or the like, or be associated with various disorders such as where occlusion of a blood vessel or elevated intraocular pressure reduces availability of blood, oxygen or other nutrients to the retina or optic nerve which can result in neuronal cell death (degeneration) and loss of vision. Such disorders include e.g. diabetes, atherosclerosis, venous capillary insufficiency, obstructive arterial and venous retinopathies, glaucoma, diabetic retinopathy and senile macular degeneration. Optic nerve injury and damage also can result in vision loss and can arise from a variety of conditions or incidents.

Certain therapies have been reported to alleviate such disorders. For example, certain calcium blockers have been reported for use in treating disorders arising from poor blood flow in the eye. See U.S. Pat. No. 5,431,907. Other therapies have included use of fibrinolytic agents and anticoagulants. See U.S. Pat. No. 4,795,423. However, such treatments have had limited effectiveness.

It thus would be desirable to have new agents for treatment of retinal ischemia and trauma, optic nerve injury and associated disorders.

SUMMARY OF THE INVENTION

The present invention includes methods for treatment of eye disorders and injury, including methods for treatment of reduced flow of blood or other nutrients to retinal tissue or optic nerve, methods for treatment of retinal ischemia and trauma and associated disorders, and methods for treatment for optic nerve injury/damage. Disorders associated with retinal or optic nerve injury or ischemia that may be treated in accordance with the invention include e.g. diabetes, atherosclerosis, venous capillary insufficiency, obstructive arterial or venous retinopathies, senile macular degeneration, cystoid macular edema and glaucoma.

The present methods in general comprise administering a therapeutically effective amount of one or more substituted guanidines or other compounds as described below to a patient in need of treatment, such as a mammal suffering from or susceptible to retinal ischemia or injury or trauma, or optic nerve injury or trauma, or associated disorder.

Compounds useful in the methods of the invention have been disclosed in U.S. Pat. No. 4,906,779 (Weber et al.; issued Mar. 6, 1990); U.S. Pat. No. 5,011,834 (Weber et al.; issued Apr. 30, 1991); U.S. Pat. No. 5,093,525 (Weber et al.; issued Mar. 3, 1992); U.S. Pat. No. 5,190,976 (Weber et al.; issued Mar. 2, 1990); U.S. Pat. No. 5,262,568 (Weber et al.; issued Nov. 16, 1993); U.S. Pat. No. 5,403,861 (Goldin et al.; issued Apr. 4, 1995); and International Applications PCT/US91/03594 (Keana et al.; International Publication No. WO 91/18868); PCT/US92/0105 (Goldin et al.; International Publication No. WO 92/14697); PCT/US92/03554 (Weber et al.; International Publication No. WO 92/19621); PCT/US94/06008 (Durant et al.; International Publication No. WO 94/27591); PCT/US94/13245 (Durant et al.; International Publication No. WO 95/14461); PCT/US94/13541 (Magar et al.; International Publication No. WO 95/14467); and PCT/US95/01536 (Goldin et al.; International Publication No. 95/20950). Each of those documents and the substituted guanidines and other therapeutic compounds disclosed therein are fully herein by reference. Thus, for example, preferred compounds for use in present methods include substituted guanidines include N,N'-disubstituted guanidines, N,N,N'-trisubstituted guanidines and N,N,N',N'-tetrasubstituted guanidines.

DETAILED DESCRIPTION OF THE INVENTION

Preferred N,N'-disubstituted guanidines for use in the present methods include compounds of the following Formula I:

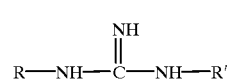

wherein R and R' each are an alkyl group of at least 4 carbon atoms or carbocyclic aryl groups of at least 6 carbon atoms, or heterocyclic or heteroaromatic of having 1 to 3 rings, 3 to 8 ring members in each and 1 to 3 heteroatoms, e.g., R and R', which can be the same or different, are alkyl of 4 or more carbon atoms, e.g., a 4 to 12 carbon atoms, preferably a straight chain, alkyl group and more preferably a 4 to 8 carbon atom alkyl group, for example, butyl, isobutyl, tertbutyl, amyl, hexyl, octyl, nonyl and decyl; cycloalkyl of 3 to 12 carbon atoms, e.g., cyclopropyl, cyclopentyl, cyclohexyl, cycloheptyl, 1,4-methylenecyclohexane, adamantyl, cyclopentylmethyl, cyclohexylmethyl, 1- or 2-cyclohexylethyl and 1-, 2- or 3-cyclohexylpropyl; carbocyclic aryl, alkaryl or aralkyl, e.g., of up to 18 carbon atoms and containing 1–3 separate or fused aromatic rings, e.g., phenyl, benzyl, 1- and 2-phenylethyl, 1-, 2-, or 3-phenylpropyl; o-, m-, or p-tolyl, m,m'-dimethylphenyl, o-, m-, or p-ethylphenyl, m,m'-diethylphenyl, m-methyl-m'-ethylphenyl and o-, m-, or p-propylphenyl, naphthyl, 2-naphthyl, and biphenyl, and heterocyclic aromatic rings including pyridyl, pyrazinyl, pyrimidyl, furyl, pyrrolyl, thienyl, thiazolyl, oxazolyl, imidazolyl, indolyl, and benzothiazolyl.

Additionally, 1, 2, 3 or more substituents may be present on the R and R' groups, e.g., alkyl of 1–8 carbon atoms, e.g., methyl, ethyl; halo, e.g., chloro, bromo, iodo, fluoro; nitro; azido; cyano; isocyanate; amino; lower-alkylamino; di-lower alkylamino; trifluoromethyl; alkoxy of 1–8 carbon atoms; e.g., methoxy, ethoxy and propoxy; acyloxy, e.g., alkanoyloxy of 1–8 carbon atoms, e.g., acetoxy and benzoxy; amido, e.g., acetamido, N-ethylacetamido; carbamido, e.g., carbamyl, N-methylcarbamyl, N,N'-dimethylcarbamyl; etc.

Especially preferred are compounds of Formula I wherein R and R' each are phenyl groups, which need not necessarily be identical, substituted with one or more of the foregoing substituents, for example, in the o-, m- or p-position or the o-, p- or m,m'-position, when the phenyl group is disubstituted, or R is phenyl or otherwise defined herein and R' is adamantyl.

Preferred compounds N,N'-disubstituted compounds for use in the present methods include N,N'-di-m-tolylguanidine; N,N'-di-o-iodophenylguanidine; N,N'-di-o-ethylphenylguanidine; N,N'-di-m-ethylphenylguanidine; N,N'-bis(2-iodophenyl)guanidine; N,N'-bis(3-tolyl)guanidine; N,N'-bis(3-ethylphenyl)guanidine; N,N'-bis(2-isopropylphenyl)guanidine; N,N'-bis(3-isopropylphenyl)guanidine; N,N'-bis(1-naphthyl)guanidine; N,N'-bis(3-methoxyphenyl)guanidine; N,N'-bis(3-trifluoromethylphenyl)guanidine; N,N'-bis(4-fluoro-3-ethylphenyl)guanidine; N,N'-bis(3,5-diethylphenyl)guanidine; N,N'-bis(3-nitrophenyl)guanidine; N,N'-bis(4-fluoro-3-nitrophenyl)guanidine; N,N'-bis(3-nitro-5-ethylphenyl)guanidine; N,N'-bis(3-azidophenyl)guanidine; N,N'-bis(quinolin-8-yl)guanidine; N,N'-bis(coumarin-8-yl)guanidine; N,N'-dibutylguanidine; N,N'-diphenylguanidine; N,N'-di-o-tolylguanidine; N,N'-di-(2-methyl-4-bromophenyl)guanidine; N,N'-di-(2-methyl-4-iodophenyl)guanidine; N,N'-di(cyclohexyl)guanidine; N,N'-di-(m-propylphenyl)guanidine; N, N'-di-(1-tetralinyl)guanidine; N,N'-di(±-endo-2-norbornyl)guanidine; N,N'-di-(exo-2-norbornyl)guanidine; N,N-di-(4-indanyl)guanidine; N,N'-diadamantylguanidine; and N,N'-dibenzylguanidine; and pharmaceutically acceptable salts of said compounds.

Asymmetrical N,N'-disubstituted guanidines are also preferred for use in methods of the invention (present methods), such as compounds of Formula I above wherein R and R' are different. Particularly preferred are asymmetrical compounds of Formula I wherein R and R' each are nonidentical aryl groups, including aryl groups substituted with one or more of the substituents discussed above with respect to Formula I, for example, in the o-, m- or p-position or the o-, p- or m,m'-position, when the phenyl group is disubstituted.

Especially preferred asymmetrical guanidines for use in the present methods include N-(1-naphthyl)-N'-(o-ethylphenyl)guanidine; N-(1-naphthyl)-N'-(m-isopropylphenyl)guanidine; N-(1-naphthyl)-N'-(m-methoxyphenyl)guanidine; N-(1-naphthyl)-N'-(4-indanyl)guanidine; N-(1-naphthyl)-N'-(m-ethylphenyl)guanidine; N-(m-ethylphenyl)-N'-(m-tolyl)guanidine; N-(m-ethylphenyl)-N'-(o-iodophenyl)guanidine; N-(m-ethylphenyl)-N'-(o-ethylphenyl)guanidine; N-(m-ethylphenyl)-N'-(o-isopropylphenyl)guanidine; N-(m-ethylphenyl)-N'-(m-isopropylphenyl)guanidine; N-(m-methylphenyl)-N'-(m-methoxyphenyl)guanidine; N-(m-ethylphenyl)-N'-(4-indanyl)guanidine; N-(m-ethylphenyl)-N'-(o-ethylphenyl)guanidine; N-(o-ethylphenyl)-N'-(m-tolyl)guanidine; N-(o-ethylphenyl)-N'-(o-iodophenyl)guanidine; N-(o-ethylphenyl)-N'-(o-isopropylphenyl)guanidine; N-(o-ethylphenyl)-N'-(m-isopropylphenyl)guanidine; N-(o-ethylphenyl)-N'-(m-methoxyphenyl)guanidine; N-(o-ethylphenyl)-N'-(4-indanyl)guanidine; N-(o-ethylphenyl)-N'-(m-ethylphenyl)guanidine; N-(o-iodophenyl)-N'-(m-tolyl)guanidine; N-(o-iodophenyl)-N'-(o-isopropylphenyl)guanidine; N-(o-iodophenyl)-N'-(m-isopropylphenylguanidine; N-(o-iodophenyl)-N'-(m-methoxyphenyl)guanidine; N-(o-iodophenyl)-N'-(4-indanyl)guanidine; N-(o-iodophenyl)-N'-(o-ethylphenyl)guanidine; N-(o-iodophenyl)-N'-(m-ethylphenyl)guanidine; N-(o-isopropylphenyl)-N'-(m-tolyl)guanidine; N-(o-isopropylphenyl)-N'-(m-isopropylphenyl)guanidine; N-(o-isopropylphenyl)-N'-(m-methoxyphenyl)guanidine; N-(o-isopropylphenyl)-N'-(4-indanyl)guanidine; N-(o-isopropylphenyl)-N'-(o-ethylphenyl)guanidine; N-(o-isopropylphenyl)-N'-(m-ethylphenyl)guanidine; N-(m-isopropylphenyl)-N'-(m-tolyl)guanidine, N-(m-isopropylphenyl)-N'-(m-methoxyphenyl)guanidine; N-(m-isopropylphenyl)-N'-(4-indanyl)guanidine; N-(m-isopropylphenyl)-N'-(o-ethylphenyl)guanidine; N-(m-isopropylphenyl)-N'-(m-ethylphenyl)guanidine; N-(m-methoxyphenyl)-N'-(m-tolyl)guanidine; N-(m-methoxyphenyl)-N'-(m-tolyl)guanidine; N-(2,4-di-iodo-5-hydroxyphenyl)-N'-(2-tolyl)guanidine; N-(1-naphthyl)-N'-(2-iodophenyl)guanidine; N-(1-naphthyl)-N'-(3-ethylphenyl)guanidine; N-(1-naphthyl)-N'-(2-isopropylphenyl)guanidine; N-(1-naphthyl)-N'-(3-tolyl)guanidine; N-(1-naphthyl)-N-(4-bromo-3-ethylphenyl)guanidine; N-(1-naphthyl)-N'-(6-methoxy-3-ethylphenyl)guanidine; N-(1-naphthyl)-N'-(4-nitro-3-ethylphenyl)guanidine; N-(1-naphthyl)-N'-[3-(1-hydroxy-ethyl)phenyl]guanidine; N-(4-fluoronaphthyl)-N'-(3-ethylphenyl)guanidine; N-(1-naphthyl)-N'-(4-fluoro-3-tolyl)guanidine; N-(1-naphthyl)-N'-(4-bromo-3-tolyl)guanidine; N-(1-naphthyl)-N'-(3-trifluoromethylphenyl)guanidine; N-(m-trifluoromethylphenyl)-N'-(m-tolyl)guanidine; N-(m-trifluoromethylphenyl)-N'-(o-isopropylphenyl)guanidine; N-(m-trifluoromethylphenyl)-N'-(m-isopropylphenyl)guanidine; N-(m-trifluoromethylphenyl)-N'-(m-methoxyphenyl)guanidine; N-(m-trifluoromethylphenyl)-N'-(4-indanyl)guanidine; N-(m-trifluoromethylphenyl)-N'-(o-ethylphenyl)guanidine; N-(m-trifluoromethylphenyl)-N'-(m-ethylphenyl)guanidine; N-(m-trifluoromethylphenyl)-N'-(o-iodophenyl)guanidine; N-(1-naphthyl)N'-(4-fluoro-3-trifluoromethylphenyl)guanidine; N-(1-naphthyl)-N'-(4-fluoro-3-ethylphenyl)guanidine; N-(7-fluoronaphthyl)-N'-(3-ethylphenyl)guanidine; N-(4-fluoronaphthyl)-N'-(4-fluoro-3-ethylphenyl)guanidine; N-(4-fluoronaphthyl)-N'-(2-isopropylphenyl)guanidine; N-(7-fluoronaphthyl)-N'-(2-isopropylphenyl)guanidine; N-(1-naphthyl)-N'-(4-fluoro-2-isopropylphenyl)guanidine; N-(4-fluoronaphthyl)-N'-(4-fluoro-2-isopropylphenyl)guanidine; N-(4-fluoronaphthyl)-N'-(6-methoxy-3-ethylphenyl)guanidine; N-(7-fluoronaphthyl)-N'-(6-methoxy-3-ethylphenyl)guanidine; N-(4-fluoronaphthyl)-N'-(6-methoxy-4-fluoro-3-ethyl)guanidine; N-(4-fluoronaphthyl)-N'-(4-fluoro-3-tolyl)guanidine; N-(7-fluoronaphthyl)-N'-(4-fluoro-3-tolyl)guanidine; N-(4-fluoronaphthyl)-N'-(4-fluoro-3-trifluoromethylphenyl)guanidine; N-(1-naphthyl)-N'-(4-fluoro-3-trifluoromethylphenyl)guanidine; N-(7-fluoronaphthyl)-N'-(4-fluoro-3-trifluoromethylphenyl)guanidine; N-(coumarin-8-yl)-N-(3-ethylphenyl)guanidine; N-(coumarin-8-yl)-N'-(3-tolyl)guanidine; N-(quinolin-8-yl)-N'-(3-ethylphenyl)guanidine; N-(quinolin-8-yl)-N'-(3-tolyl)guanidine; N-(cyclohexyl)-N'-(4-bromo-2-methylphenyl)guanidine; N-(1-naphthyl)-N'-(o-iodophenyl)guanidine; N-(1-naphthyl)-N'-(m-ethylphenyl)guanidine; N-(1-naphthyl)-N'-(o-isopropylphenyl)guanidine; N-(1-naphthyl)-N'-(m-tolylphenyl)guanidine; N-(1-naphthyl)-N'-(o-ethylphenyl)guanidine; N-(1-naphthyl)-N'-(m-isopropylphenyl)guanidine; N-(1-naphthyl)-N'-(m-methoxyphenyl)guanidine; N-(1-naphthyl)-N'-(4-indanylphenyl)guanidine; N-(m-ethylphenyl)-N'-(o-iodophenyl)guanidine; N-(m-ethylphenyl)-N'-(m-ethylphenyl)guanidine; N-(m-ethylphenyl)-N'-(o-isopropylphenyl)guanidine; N-(m-ethylphenyl)-N'-(m-tolylphenyl)guanidine; N-(m-ethylphenyl)-N'-(o-ethylphenyl)guanidine; N-(m-ethylphenyl)-N'-(m-isopropylphenyl)guanidine; N-(m-ethylphenyl)-N'-(m-methoxyphenyl)guanidine; N-(m-ethylphenyl)-N'-(4-indanylphenyl)guanidine; N-(o-ethylphenyl)-N'-(m-tolyl)guanidine; N-(o-ethylphenyl)-N'-(o-iodophenyl)guanidine; N-(o-ethylphenyl)-N'-(o-isopropylphenyl)guanidine; N-(o-ethylphenyl)-N'-(m-isopropylphenyl)guanidine; N-(o-ethylphenyl)-N'-(m-methoxyphenyl)guanidine; N-(o- ethylphenyl)-N'-(4-indanyl)guanidine; N-(o-iodophenyl)-N'-(m-tolyl)guanidine; N-(o-iodophenyl)-N'-(o-isopropylphenyl)guanidine; N-(o-iodophenyl)-N'-(m-isopropylphenyl)guanidine; N-(o-iodophenyl)-N'-(m-isopropylphenyl)guanidine; N-(o-iodophenyl)-N'-(m-methoxyphenyl)guanidine; N-(o-iodophenyl)-N'-(4-indanyl)guanidine; N-(o-isopropylphenyl)-N'-(m-tolyl) guanidine; N-(o-isopropylphenyl)-N'-(m-isopropylphenyl) guanidine; N-(o-isopropylphenyl)-N'-(m-methoxyphenyl) guanidine; N-(o-isopropylphenyl)-N'-(4-indanyl)guanidine; N-(m-isopropylphenyl)-N'-(m-tolyl)guanidine; N-(m-isopropylphenyl)-N'-(m-methoxyphenyl)guanidine; N-(m-isopropylphenyl)-N'-(4-indanyl)guanidine; N-(m-methoxyphenyl)-N'-(m-tolyl)guanidine; N-(m-methoxyphenyl)-N'-(4-indanyl)guanidine; N-(4-indanyl)-N'-(m-tolyl)guanidine; N-(2-methylazidophenyl)-N'-(2-methylphenyl)guanidine; N-adamantyl-N'-(2-methylphenyl)guanidine; N-(iodophenyl)-N'-(2-methylphenyl)guanidine; N-(2-methyl-4-nitrophenyl)-N'-(2-methylphenyl)guanidine; N-(2-iodophenyl)-N'-(adamantyl)guanidine; N-(2-methylphenyl)-N'-(cyclohexyl) guanidine; N-adamantyl-N'-phenylguanidine; N-(3,5-dimethyl-1-adamantyl)-N'-(o-tolyl)guanidine; N-(3,5-dimethyl-1-adamantyl)-N'-(o-iodophenyl)guanidine; N-(1-adamantyl)-N'-(o-nitrophenyl)guanidine; N-(exo-2-isobornyl)-N'-(o-iodophenyl)guanidine; N-(exo-2-isobornyl)-N'-(o-tolyl)guanidine; N-(o-iodophenyl)-N'-(t-butyl)guanidine; N-(adamant-1-yl)-N'-(o-isopropylphenyl) guanidine; N-(adamant-1-yl)-N'-(p-bromo-o-tolyl) guanidine; N-(cyclohexyl)-N'-(p-bromo-o-tolyl)guanidine; N-(adamant-2-yl)-N'-(p-iodophenyl)guanidine; N-(adamantan-1-yl)-N'-(2-trifluoromethylphenyl) guanidine; N-(adamantan-1-yl)-N'-(2-methylphenyl)-N'-methylguanidine; N-(adamantan-1-yl)-N'-(6-coumarinyl) guanidine; N-(adamantan-1-yl)-N'-(8-coumarinyl) guanidine; N-(adamantan-1-yl)-N'-(2,4-difluorophenyl) guanidine; and N-(adamantan-1-yl)-N'-(2-trifluoromethyl-4-fluorophenyl)guanidine; and pharmaceutically acceptable salts of said compounds.

N,N,N'-trisubstituted guanidines are also preferred for use in methods of the invention, including compounds of the following Formula II:

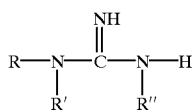

II wherein R, R' and R" are independently a $C_1$–$C_8$ alkyl group, a $C_2$–$C_8$ alkenyl group, $C_2$–$C_8$ alkynyl group, cycloalkyl group, cycloalkyl group substituted by one or more substituents, cycloalkenyl group, cycloalkenyl group substituted with one or more substituents, carbocyclic aryl group, carbocyclic aryl group substituted by one or more substituents, alkaryl group, alkaryl group substituted by one or more substituents, heterocyclic group, heterocyclic group substituted by one or more substituents, heteroaryl group, or a heteroaryl group substituted by one or more substituents; or a physiologically acceptable salt thereof;

wherein said substituent is a halogen of chloro, fluoro, bromo, iodo, $C_1$–$C_8$ alkyl, $C_1$–$C_8$ alkoxy, cyano, $C_3$–$C_{15}$ dialkylaminoalkyl, carboxy, carboxamido, $C_1$–$C_8$ alkylthio, allyl, aralkyl, alkaryl, $C_3$–$C_6$ cycloalkyl, aroyl, aralkoxy, $C_2$–$C_8$ acyl, aryl, heteroaryl, an aryl fused to a benzene ring, a heteroaryl fused to a benzene ring, $C_3$–$C_6$ heterocycloalkyl, a $C_3$–$C_6$ heterocycloalkyl ring fused to a benzene ring, $C_1$–$C_8$ alkylsulfonyl, arylthio, amino, $C_1$–$C_8$ alkylamino, $C_2$–$C_{15}$ dialkylamino, hydroxy, hydroxyalkyl, carbamoyl, $C_1$–$C_8$ N-alkylcarbamoyl, $C_2$–$C_{15}$ N,N'-diaLkylcarbamoyl, nitro, azido or a $C_2$–$C_{15}$ dialkylsulfamoyl.

Preferably, with reference to Formula II, preferred N,N, N'-trisubstituted guanidines are wherein R and R" are independently a cycloalkyl group, a cycloalkyl group substituted with one or more substituents, cycloalkenyl, cycloalkenyl substituted by one or more substituents, carbocyclic aryl group, carbocyclic aryl group substituted with one or more substituents, alkaryl group, alkaryl group substituted with one or more substituents, aralkyl, aralkyl group substituted with one or more substituents, heterocyclic group, heterocyclic group substituted with one or more substituents, heteroaryl group, or a heteroaryl group substituted with one or more substituents; and R' is independently a $C_1$–$C_8$ alkyl group, $C_2$–$C_6$ alkenyl group, $C_2$–$C_6$ alkynyl group, an alkaryl group, or a substituted alkaryl group.

Especially preferred N,N,N'-trisubstituted guanidines for use in the present methods include N,N'-di-(1-naphthyl)-N-methylguanidine; N,N'-di-(1-naphthyl)-N-ethylguanidine; N,N'-di-(m-ethylphenyl)-N-methylguanidine; N-(o-isopropylphenyl)-N'-methyl-N'-(1-naphthyl)guanidine; N-(m-ethylphenyl)-N-methyl-N'-(1-naphthyl)guanidine; N-ethyl-N,N'-di-(m-ethylphenyl)guanidine; N-ethyl-N-(m-ethylphenyl)-N'-(4-indanyl)guanidine; N-ethyl-N-(m-ethylphenyl)-N'-(4-indenyl)guanidine; N-ethyl-N-(m-ethylphenyl)-N'-(o-iodophenyl)guanidine; N-ethyl-N-(m-ethylphenyl)-N'-(o-isopropylphenyl)guanidine; N-ethyl-N-(m-ethylphenyl)-N'-(1-naphthyl)guanidine; N-ethyl-N-(m-ethylphenyl)-N'-(m-methylphenyl)guanidine; N-ethyl-N-(4-indanyl)-N'-(m-ethylphenyl)guanidine; N-ethyl-N-(4-indenyl)-N'-(m-ethylphenyl)guanidine; N-ethyl-N-(o-iodophenyl)-N'-(m-ethylphenyl)guanidine; N-ethyl-N-(o-isopropylphenyl)-N'-(m-ethylphenyl)guanidine; N-ethyl-N-(1-naphthyl)-N'-(m-ethylphenyl)guanidine; N-ethyl-N-(m-methylphenyl)-N'-(m-ethylphenyl)guanidine; N-isopropyl-N,N'-di-(m-ethylphenyl)guanidine; N-isopropyl-N-(m-ethylphenyl)-N'-(4-indanyl)guanidine; N-isopropyl-N-(m-ethylphenyl)-N'-(4-indenyl)guanidine; N-(isopropyl)-N-(m-ethylphenyl)-N'-(o-iodophenyl)guanidine; N-isopropyl-N-(m-ethylphenyl)-N'-(o-isopropylphenyl)guanidine; N-isopropyl-N-(m-ethylphenyl)-N'-(1-naphthyl)guanidine; N-isopropyl-N-(m-ethylphenyl)-N'-(m-methylphenyl) guanidine; N-isopropyl-N-(4-indanyl)-N'-(m-ethylphenyl) guanidine; N-isopropyl-N-(4-indenyl)-N'-(m-ethylphenyl) guanidine; N-isopropyl-N-(o-iodophenyl)-N'-(m-ethylphenyl)guanidine; N-isopropyl-N-(o-isopropylphenyl)-N'-(m-ethylphenyl)guanidine; N-isopropyl-N-(1-naphthyl)-N'-(m-ethylphenyl)guanidine; N-isopropyl-N-(m-methylphenyl)-N'-(m-ethylphenyl) guanidine; N-methyl-N-(m-ethylphenyl)-N'-(4-indanyl) guanidine; N-methyl-N-(m-ethylphenyl)-N'-(4-indenyl) guanidine; N-methyl-N-(m-ethylphenyl)-N'-(o-iodophenyl) guanidine; N-methyl-N-(m-ethylphenyl)-N'-(o-isopropylphenyl)guanidine; N-methyl-N-(m-ethylphenyl)-N'-(m-methylphenyl)guanidine; N-methyl-N-(4-indanyl)-N'-(m-ethylphenyl)guanidine; N-methyl-N-(4-indenyl)-N'-(m-ethylphenyl)guanidine; N-methyl-N-(o-iodophenyl)-N'-(m-ethylphenyl)guanidine; N-methyl-N-(o-isopropylphenyl)-N'-(m-ethylphenyl)guanidine; N-methyl-N-(o-isopropylphenyl)-N'-(m-ethylphenyl)guanidine; N-methyl-N-(1-naphthyl)-N'-(m-ethylphenyl)guanidine; N-methyl-N-(m-methylphenyl)-N'-(m-ethylphenyl) guanidine; N-(8-coumarinyl)-N'-(3-ethylphenyl)-N'-methylguanidine; N-(1-naphthyl)-N'-(8-coumarinyl)-N- ethylguanidine; N-(8-coumarinyl)-N'-(3-ethylphenyl)-N-ethylguanidine; N-(1-naphthyl)-N'-(8-coumarinyl)-N-ethylguanidine; N-(1-naphthyl)-N'-(3-methylphenyl)-N'-methylguanidine; N-(1-naphthyl)-N'-(3-nitrophenyl)-N'-methylguanidine; N-(1-naphthyl)-N'-(3-azidophenyl)-N'-methylguanidine; N-(7-fluoro-1-naphthyl)-N'-(3-ethylphenyl)-N'-methylguanidine; N-(4-fluoro-1-naphthyl)-N'-(3-ethylphenyl)-N'-methylguanidine; N-(1-naphthyl)-N'-(4-fluoro-3-ethylphenyl)-N'-methylguanidine; N-(2-fluoro-1-naphthyl)-N'-(3-ethylphenyl)-N'-methylguanidine; N-(5-fluoro-1-naphthyl)-N'-(3-ethylphenyl)-N'-methylguanidine; N-(8-fluoro-1-naphthyl)-N'-(3-ethylphenyl)-N'-methylguanidine; N-(1-naphthyl)-N'-(2-fluoro-3-ethylphenyl)-N'-methylguanidine; N-(1-naphthyl)-N'-(6-fluoro-3-ethylphenyl)-N'-methylguanidine; N-(1-naphthyl)-N'-(2,4-difluoro- 3-ethylphenyl)-N'-methylguanidine; N-(1-napthyl)-N'-(6-difluoro-3-ethylphenyl)-N'-methylguanidine; N-(1-naphthyl)-N'-(2,4,6-trifluoro-3-ethylphenyl)-N'-methylguanidine; N-(2,4-difluoro-1-naphthyl)-N'-(3-ethylphenyl)-N'-methylguanidine; N-(2,4-difluoro-1-naphthyl)-N'-(3-ethylphenyl)-N'-methylguanidine; N-(2,4,5-trifluoro-1-naphthyl)-N'-(3-ethylphenyl)-N'-methylguanidine; N-(2,4,8-trifluoro-1-naphthyl)-N'-(3-ethylphenyl)-N'-methylguanidine; N-(4-fluoro-1-naphthyl)-N'-(2,6-difluoro-3-ethylphenyl)-N'-methylguanidine; N-(4-fluoro-1-naphthyl)-N'-(2,4-difluoro-3-ethylphenyl)-N'-methylguanidine; N-(7-fluoro-1-naphthyl)-N'-(4-fluoro-3-ethylphenyl)-N'-methylguanidine; N-(4-fluoro-1-naphthyl)-N'-(4-fluoro-3-ethylphenyl)-N'-methylguanidine; N-(4-fluoro-1-naphthyl)-N'-(6-fluoro-3-ethylphenyl)-N'-methylguanidine; N-(8-coumarinyl)-N'-(3-ethylphenyl)-N'-ethylguanidine; N-(1-naphthyl)-N'-(8-coumarinyl)-N-ethylguanidine; N-(8-coumarinyl)-N'-(3-nitrophenyl)-N'-methylguanidine; N-(8-coumarinyl)-N'-(3-methylphenyl)-N'-methylguanidine; N-(8-coumarinyl)-N'-(4-fluoro-3-ethylphenyl)-N'-methylguanidine; N,N'-di(8-coumarinyl)-N-methylguanidine; N,N'-di(8-coumarinyl)-N-ethylguanidine; N-(2-fluoronaphthyl)-N'-(3-methylphenyl)-N'-methylguanidine; N-(4-fluoronaphthyl)-N'-(3-methylphenyl)-N'-methylguanidine; N-(5-fluoronaphthyl)-N'-(3-methylphenyl)-N'-methylguanidine; N-(7-fluoronaphthyl)-N'-(3-methylphenyl)-N'-methylguanidine; N-(2,4-difluoronaphthyl)-N'-(3-methylphenyl)-N'-methylguanidine; N-(2,4,5-trifluoronaphthyl)-N'-(3-methylphenyl)-N'-methylguanidine; N-(2,4,8-trifluoronaphthyl)-N'-(3-methylphenyl)-N'-methylguanidine; N-(1-naphthyl)-N'-(2-fluoro-3-methylphenyl)-N'-methylguanidine; N-(1-naphthyl)-N'-(4-fluoro-3-methylphenyl)-N'-methylguanidine; N-(1-naphthyl)-N'-(5-fluoro-3-methylphenyl)-N'-methylguanidine; N-(1-naphthyl)-N'-(3-nitrophenyl)-N'-ethylguanidine; N-(1-naphthyl)-N'-(4-fluoro-3-ethylphenyl)-N-methylguanidine; N-(1-naphthyl)-N'-(3-trifluoromethylphenyl)-N'-methylguanidine; N-(8-coumarinyl)-N'-(3-trifluoromethylphenyl)-N'-methylguanidine; N-(1-naphthyl)-N'-(3-trifluoromethylphenyl)-N'-ethylguanidine; and N-(8-coumarinyl)-N'-(3-trifluoromethylphenyl)-N'-ethylguanidine; and pharmaceutically acceptable salts of said compounds.

N,N,N',N'-tetrasubstituted guanidines are also preferred for use in methods of the invention, including compounds of the following Formula III:

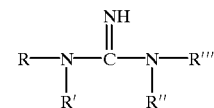

wherein R, R', R" and R'" are independently a $C_1$–$C_8$ alkyl group, a $C2$–$C_8$ alkenyl group, $C_2$–$C_8$ alkynyl group, cycloalkyl group, cycloalkyl group substituted by one or more substituents, cycloalkenyl group, cycloalkenyl group substituted with one or more substituents, carbocyclic aryl group, carbocyclic aryl group substituted by one or more substituents, alkaryl group, alkaryl group substituted by one or more substituents, heterocyclic group, heterocyclic group substituted by one or more substituents, heteroaryl group, or a heteroaryl group substituted by one or more substituents;
or a physiologically acceptable salt thereof;
wherein said substituent is halogen such as chloro, fluoro, bromo, iodo, $C_1$–$C_8$ alkyl, $C_1$–$C_8$ alkoxy, cyano, $C_3$–$C_{15}$ dialkylaminoalkyl, carboxy, carboxamido, $C_1$–$C_8$ alkylthio, allyl, aralkyl, alkaryl, $C_3$–$C_6$ cycloalkyl, aroyl, aralkoxy, $C_2$–$C_8$ acyl, aryl, heteroaryl, an aryl fused to a benzene ring, a heteroaryl fused to a benzene ring, $C_3$–$C_6$ heterocycloalkyl, a $C_3$–$C_6$ heterocycloalkyl ring fused to a benzene ring, $C_1$–$C_8$ aLkylsulfonyl, arylthio, amino, $C_1$–$C_8$ alkylamino, $C_2$–$C_{15}$ dialkylamino, hydroxy, hydroxyalkyl, carbamoyl, $C_1$–$C_8$ N-alkylcarbamoyl, $C_2$–$C_{15}$ N,N'-dialkylcarbamoyl, nitro, azido or a $C_2$–$C_{15}$ dialkylsulfamoyl.

With reference to Formula II, preferable N,N,N',N'-tetrasubstituted guanidines are wherein R and R" are independently a cycloalkyl group, a cycloalkyl group substituted with one or more substituents, a cycloalkyl group, a cycloalkyl group substituted with one or more substituents, a cycloalkenyl group, cycloalkenyl group substituted with one or more substituents, carbocyclic aryl group, carbocyclic aryl group substituted with one or more substituents, alkaryl group, alkaryl group substituted with one or more substituents, aralkyl group, aralkyl group substituted with one or more substituents, heterocyclic group, heterocyclic group substituted with one or more substituents, heteroaryl group, or a heteroaryl group substituted with one or more substituents; and R' and R'" are independently a $C_1$–$C_8$ alkyl group, $C_2$–$C_6$ alkenyl group, $C_2$–$C_6$ alkynyl group, an alkaryl group, a substituted alkaryl, a cycloalkaryl, or substituted cycloalkaryl group.

Especially preferred guanidines of Formula III are those wherein R and R" are independently carbocyclic aryl groups, substituted cycloalkyl groups, cycloalkenyl groups, cycloalkenyl groups substituted with one or more substituents, carbocyclic aryl groups, substituted carbocyclic aryl groups, alkaryl groups, substituted aralkyl groups, heterocyclic groups, substituted heterocyclic groups, heteroaryl groups, or substituted heteroaryl groups; and R' and R'" are $C_1$–$C_8$ alkyl groups. Particularly preferred N,N,N'N'-tetrasubstituted guanidines include N,N'-diethyl-N,N'-di-(m-ethylphenyl)guanidine; N,N'-diethyl-N,N'-di-(1-naphthyl)guanidine; N,N'-diethyl-N-(m-ethylphenyl)-N'-(4-indanyl)guanidine; N,N'-diethyl-N-(m-ethylphenyl)-N'-(4-indenyl)guanidine; N,N'-diethyl-N-(m-ethylphenyl)-N'-(o-iodophenyl)guanidine; N,N'-diethyl-N-(m-ethylphenyl)-N'-(o-isopropylphenyl)guanidine; N,N'-diethyl-N-(m-ethylphenyl)-N'-(1-naphthyl)guanidine; N,N'-diethyl-N-(1-naphthyl)-N'-(m-ethylphenyl)guanidine; N,N'-diethyl-N-(m-methylphenyl)-N'-(m-ethylphenyl)guanidine; N,N'-diisopropyl-N,N'-di-(m-ethylphenyl)guanidine; N,N'- diisopropyl-N-(m-ethylphenyl)-N'-(4-indanyl)guanidine; N,N'-diisopropyl-N-(m-ethylphenyl)-N'-(4-indenyl) guanidine; N,N'-diisopropyl-N-(m-ethylphenyl)-N'-(o-iodophenyl)guanidine; N,N'-diisopropyl-N-(m-ethylphenyl)-N'-(o-isopropylphenyl)guanidine; N,N'-diisopropyl-N-(m-ethylphenyl)-N'-(1-naphthyl)guanidine; N,N'-diisopropyl-N-(m-ethylphenyl)-N'-(m-methylphenyl) guanidine; N,N'-dimethyl-N,N'-di-(m-ethylphenyl) guanidine; N,N'-dimethyl-N-(m-ethylphenyl)-N'-(4-indanyl)guanidine; N,N'-dimethyl-N-(m-ethylphenyl)-N'-(4-indenyl)guanidine; N,N'-dimethyl-N-(m-ethylphenyl)-N'-(o-iodophenyl)guanidine; N,N'-dimethyl-N-(m-ethylphenyl)-N'-(o-isopropylphenyl)guanidine; N,N'-dimethyl-N-(m-ethylphenyl)-N'-(1-naphthyl)guanidine; N,N'-dimethyl-N-(m-ethylphenyl)-N'-(m-methylphenyl) guanidine; N-ethyl-N'-isopropyl-N,N'-di-(m-ethylphenyl) guanidine; N-ethyl-N-(m-ethylphenyl)-N'-(4indanyl)-N'-isopropylguanidine; N-ethyl-N-(m-ethylphenyl)-N'-(4-indenyl)-N'-isopropylguanidine; N-ethyl-N-(m-ethylphenyl)-N'-(o-iodophenyl)-N'-isopropylguanidine; N-ethyl-N-(m-ethylphenyl)-N'-(o-isopropylphenyl)-N'-isopropylguanidine; N-ethyl-N-(m-ethylphenyl)-N'-(1-naphthyl)-N'-isopropylguanidine; N-ethyl-N-(m-ethylphenyl)-N'-(m-methylphenyl)-N'-isopropylguanidine; N-ethyl-N-(4-indanyl)-N'-(m-ethylphenyl)-N'-isopropylguanidine; N-ethyl-N-(4-indenyl)-N'-(m-ethylphenyl)-N'-isopropylguanidine; N-ethyl-N-(o-iodophenyl)-N'-(m-ethylphenyl)-N'-isopropylguanidine; N-ethyl-N-(o-isopropylphenyl)-N'-(m-ethylphenyl)-N'-isopropylguanidine; N-ethyl-N-(1-naphthyl)-N'-(m-ethylphenyl)-N'-isopropylguanidine; N-ethyl-N-(m-methylphenyl)-N'-(m-ethylphenyl)-N'-isopropylguanidine; N,N'-diisopropyl-N,N'-di-(m-ethylphenyl)guanidine; N,N'-diisopropyl-N-(m-ethylphenyl)-N'-(4-indanyl)guanidine; N,N'-diisopropyl-N-(m-ethylphenyl)-N'-(4-indenyl) guanidine; N,N'-diisopropyl-N-(m-ethylphenyl)-N'-(o-iodophenyl)guanidine; N,N'-diisopropyl- N-(m-ethylphenyl)-N'-(o-isopropylphenyl)guanidine; N,N'-diisopropyl-N-(m-ethylphenyl)-N'-(1-naphthyl)guanidine; N,N'-diisopropyl-N-(m-ethylphenyl)-N'-(m-methylphenyl) guanidine; N,N'-diisopropyl-N-(4-indanyl)-N'-(m-ethylphenyl)guanidine; N,N'-diisopropyl-N-(4-indenyl)-N'-(m-ethylphenyl)guanidine; N,N'-diisopropyl)-N-(o-iodophenyl)-N'-(m-ethylphenyl)guanidine; N,N'-diisopropyl-N-(o-isopropylphenyl)-N'-(m-ethylphenyl) guanidine; N,N'-diisopropyl-N-(1-naphthyl)-N'-(m-ethylphenyl)guanidine; N,N'-diisopropyl-N-(m-methylphenyl)-N'-(m-ethylphenyl)guanidine; N-methyl-N,N'-di-(m-ethylphenyl)-N'-isopropylguanidine; N-methyl-N-(m-ethylphenyl)-N'-(4-indanyl)-N'-isopropylguanidine; N-methyl-N-(m-ethylphenyl)-N'-(4-indenyl)-N'-isopropylguanidine; N-methyl-N-(m-ethylphenyl)-N'-(o-iodophenyl)-N'-isopropylguanidine; N-methyl-N-(m-ethylphenyl)-N'-(o-isopropylphenyl)-N'-isopropylguanidine; N-methyl-N-(m-ethylphenyl)-N'-(1-naphthyl)-N'-isopropylguanidine; N-methyl-N-(m-ethylphenyl)-N'-(m-methylphenyl)-N'-isopropylguanidine; N-methyl-N-(4-indanyl)-N'-(m-ethylphenyl)-N'-isopropylguanidine; N-methyl-N-(4-indenyl)-N'-(m-ethylphenyl)-N'-isopropylguanidine; N-methyl-N-(o-iodophenyl)-N'-(m-ethylphenyl)-N'-isopropylguanidine; N-methyl-N-(o-isopropylphenyl)-N'-(m-ethylphenyl)-N'-isopropylguanidine; N-methyl-N-(1-naphthyl)-N'-(m-ethylphenyl)-N'-isopropylguanidine; N-methyl-N-(m-methylphenyl)-N'-(m-ethylphenyl)-N'-isopropylguanidine; N-ethyl-N,N'-di-(m-ethylphenyl)-N'-methylguanidine; N-ethyl-N-(m-ethylphenyl)-N'-(4-indanyl)-N'-methylguanidine; N-ethyl-N-(m-ethylphenyl)-N'-(4-indenyl)-N'-methylguanidine; N-ethyl-N-(m-ethylphenyl)-N'-(o-iodophenyl)-N'-methylguanidine; N-ethyl-N-(m-ethylphenyl)-N'-(o-isopropylphenyl)-N'-methylguanidine; N-ethyl-N-(m-ethylphenyl)-N'-(1-naphthyl)-N'-methylguanidine; N-ethyl-N-(m-ethylphenyl)-N'-(m-methylphenyl)-N'-methylguanidine; N,N'-di(1-naphthyl)-N,N'-dimethylguanidine; N-(8-coumarinyl)-N'-(3-ethylphenyl)-N,N-dimethylguanidine; N,N'-di(8-coumarinyl)-N,N'-dimethylguanidine; N,N'-di(8-coumarinyl)-N-methyl-N'-ethylguanidine; N-(1-naphthyl)-N'-(3-nitrophenyl)-N,N'-dimethylguanidine; N-(1-naphthyl)-N'-(3-azidophenyl)-N,N'-dimethylguanidine; N-(8-coumarinyl)-N'-(3-nitrophenyl)-N,N'-dimethylguanidine; N-(8-coumarinyl)-N'-(3-azidophenyl)-N,N'-dimethylguanidine; N-(7-fluoro-1-naphthyl)-N'-(3-ethylphenyl)-N,N'-dimethylphenylguanidine; N-(4-fluoro-1-naphthyl)-N'-(3-ethylphenyl)-N,N'-dimethylguanidine; N-(1-naphthyl)-N'-(4-fluoro-3-ethylphenyl-N,N'-dimethylguanidine; N-(1-naphthyl)-N'-(3-methylphenyl)-N,N'-dimethylguanidine; N-(8-coumarinyl)-N-(3-methylphenyl)-N,N'-dimethylguanidine; N-(1-naphthyl)-N'-(3-nitrophenyl)-N,N'-diethylguanidine; N-(1-naphthyl)-N'-(3-azidophenyl)-N,N'-diethylguanidine; N-(8-coumarinyl)-N'-(3-nitrophenyl)-N,N'-diethylguanidine; N-(8-coumarinyl)-N'-(3-azidophenyl)-N,N'-diethylguanidine; N-(7-fluoro-1-naphthyl)-N'-(3-ethylphenyl)-N,N'-diethylphenylguanidine; N-(4-fluoro-1-naphthyl)-N'-(3-ethylphenyl)-N,N'-diethylguanidine; N-(1-naphthyl)-N'-(4-fluoro-3-ethylphenyl)-N,N'-diethylguanidine; N-(1-naphthyl)-N'-(3-methylphenyl)-N,N'-diethylguanidine; and N-(8-coumarinyl)-N-(3-methylphenyl)-N,N'-diethylguanidine; and pharmaceutically acceptable salts of said compounds.

With respect to the N,N,N'-trisubstituted and N,N,N',N'-tetrasubstituted guanidines of Formulae II and III above, typical alkyl groups are, for example, methyl, ethyl, propyl, isopropyl, butyl, isobutyl, tert-butyl, amyl, hexyl, heptyl and octyl.

With respect to the N,N,N'-trisubstituted and N,N,N',N'-tetrasubstituted guanidines of Formulae II and III above, typical cycloalkyl groups have 3 to 12 carbon atoms, e.g., cyclopropyl, cyclopentyl, cyclohexyl, cycloheptyl, 1,4-methylenecyclohexyl, adamantyl, norbornyl, isobornyl, menthyl, cyclopentylnethyl, cyclohexylmethyl, 1- or 2-cyclohexylethyl and 1-, 2- or 3-cyclohexylpropyl.

With respect to the N,N,N'-trisubstituted and N,N,N',N'-tetrasubstituted guanidines of Formulae II and III above, typical cycloalkenyl groups have 5 to 12 carbon atoms and include cyclopentenyl, cyclohexenyl, cycloheptenyl, and cycloctenyl groups.

With respect to the N,N,N'-trisubstituted and N,N,N',N'-tetrasubstituted guanidines of Formulae II and III above, typical carbocyclic aryl groups include phenyl, 1-naphthyl, 2-naphthyl, biphenyl, phenanthracyl, and anthracyl groups.

With respect to the N,N,N'-trisubstituted and N,N,N',N'-tetrasubstituted guanidines of Formulae II and III above, typical alkaryl or aralkyl groups, e.g., of up to 18 carbon atoms, may contain 1–3 separate or fused aromatic rings, e.g., benzyl, $C_1$–$C_3$ alkylphenol, nitrophenyl, naphthyl, 1- and 2-phenylethyl, 1-, 2-, or 3-phenylpropyl, o-, m-, or p-tolyl, m,m'-dimethylphenyl, o-, m-, or p-ethylphenyl, m,m'-diethylphenyl, m-methyl-m-ethylphenyl, o-propyl phenyl, and o-isopropylphenyl.

With respect to the N,N,N'-trisubstituted and N,N,N',N'-tetrasubstituted guanidines of Formulae II and III above, typical heterocyclic aromatic rings include coumarinyl, pyridyl, pyrazinyl, pyrimidyl, furyl, pyrrolyl, thienyl, thiazolyl, oxazolyl, imidazolyl, indolyl, benzofuranyl and benzthiazolyl.

With respect to the N,N,N'-trisubstituted and N,N,N',N'-tetrasubstituted guanidines of Formulae II and III above, typical alkenyl groups include allyl, 2-butenyl, 2-pentenyl and 2-hexenyl groups.

With respect to the N,N,N'-trisubstituted and N,N,N',N'-tetrasubstituted guanidines of Formulae II and III above, typical alkynyl groups include 2-butynyl, 2-pentynyl and 2-hexynyl groups.

With respect to the N,N,N'-trisubstituted and N,N,N',N'-tetrasubstituted guanidines of Formulae II and III above, typical aroyl groups include carbonyl substituted by the above-listed aryl groups.

With respect to the N,N,N'-trisubstituted and N,N,N',N'-tetrasubstituted guanidines of Formulae II and III above, typical aralkoxy groups include $C_1-C_8$ alkoxy groups substituted by the above-listed aryl groups.

With respect to N,N,N'-trisubstituted and N,N,N',N'-tetrasubstituted guanidines of Formulae II and III above, typical heterocycloalkyl groups include tetrahydrofuranyl, tetrahydropyranyl, piperidinyl, morpholino and pyrrolidinyl groups.

Also preferred for use in the present methods are substituted N,N'-disubstituted, N,N,N'-trisubstituted and N,N,N',N'-tetrasubstituted guanidines having a 2,5-substituted-phenyl substituent, particularly compounds of the following Formula IV:

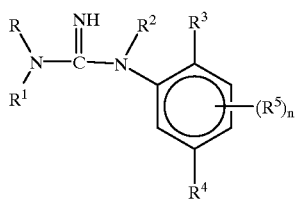

IV wherein R, $R^1$ and $R^2$ are each independently hydrogen, substituted or unsubstituted alkyl having from 1 to about 20 carbon atoms, substituted or unsubstituted alkenyl having from 2 to about 20 carbon atoms, substituted or unsubstituted alkynyl having from 2 to about 20 carbon atoms, substituted or unsubstituted alkoxy having from 1 to about 20 carbon atoms, substituted or unsubstituted alkylthio having from 1 to about 20 carbon atoms, substituted or unsubstituted alkylsulfinyl having from 1 to about 20 carbon atoms, substituted or unsubstituted alkylsulfonyl having from 1 to about 20 carbon atoms, substituted or unsubstituted aminoalkyl having 1 to about 20 carbon atoms, substituted or unsubstituted carbocyclic aryl having at least about 6 carbon atoms, substituted or unsubstituted aralkyl having at least about 6 carbon ring atoms, or a substituted or unsubstituted heteroaromatic or heteroalicyclic group having 1 to 3 rings, 3 to 8 ring members in each ring and 1 to 3 heteroatoms;

$R^3$, $R^4$, and each $R^5$ substituent are each independently halogen, hydroxyl, azido, substituted or unsubstituted alkyl having from 1 to about 20 carbon atoms, substituted or unsubstituted alkenyl having from 2 to about 20 carbon atoms, substituted or unsubstituted alkynyl having from 2 to about 20 carbon atoms, substituted or unsubstituted alkoxy having from 1 to about 20 carbon atoms, substituted or unsubstituted alkylthio having from 1 to about 20 carbon atoms, substituted or unsubstituted alkylsulfinyl having from 1 to about 20 carbon atoms, substituted or unsubstituted alkylsulfonyl having from 1 to about 20 carbon atoms, substituted or unsubstituted aminoalkyl having from 1 to about 20 carbon atoms, substituted or unsubstituted carbocyclic aryl having at least about 6 carbon ring atoms, substituted or unsubstituted aralkyl having at least about 6 carbon ring atoms, nitro, cyano, substituted or unsubstituted alkanoyl such as $C_{1-8}$ alkanoyl, e.g. acyl, or substituted or unsubstituted carboxy such as acid or ester groups of the formula —$(CH_2)_q$COOY where q is an integer of 0–8, Y is hydrogen or substituted or unsubstituted $C_{1-8}$ alkyl; n is 0 ($R^5$ is hydrogen), 1, 2 or 3; or a pharmaceutically acceptable salt thereof.

In the above Formula IV, at least one of R and $R^1$ will typically be other than hydrogen. Preferred compounds of Formula IV include trisubstituted compounds where one of the guanidine substituents R, $R^1$ and $R^2$ of Formula IV above is hydrogen and the other two substituents are other than hydrogen, more preferably where R or $R^1$ is heterocyclic aryl or carbocyclic aryl, still more preferably where R is substituted or unsubstituted heterocyclic aryl or substituted or unsubstituted carbocyclic aryl and one of $R^1$ and $R^2$ is hydrogen and one of $R^1$ and $R^2$ is substituted or unsubstituted alkyl. Also preferred are N,N'-disubstituted compounds, i.e. where one of R and $R^1$ of Formula IV is hydrogen and $R^2$ is hydrogen, preferably where R is substituted or unsubstituted heterocyclic aryl or substituted or unsubstituted carbocyclic aryl and $R^1$ and $R^2$ are hydrogen. Also preferred are N,N,N'N'-tetrasubstituted compounds, i.e. where each of R, $R^1$ and $R^2$ substituents of Formula IV is other than hydrogen, preferably where R or $R^1$ is substituted or unsubstituted heterocyclic aryl or substituted or unsubstituted carbocyclic aryl, more preferably where R is substituted or unsubstituted heterocyclic aryl or substituted or unsubstituted carbocyclic aryl and $R^1$ and $R^2$ are each substituted or unsubstituted alkyl.

Preferred phenyl ring substituents $R^3$, $R^4$ and $R^5$ of compounds of Formula IV include halogen such as F, Cl, Br and I, hydroxyl azido, substituted or unsubstituted alkyl including halogenated alkyl, substituted or unsubstituted alkoxy including halogenated alkoxy and substituted and unsubstituted alkylthio. Typically preferred phenyl ring substituents have 1 to 4 carbon atoms with methyl, ethyl and propyl including isopropyl being particularly preferred. Halogen-substituted alkyl and alkoxy groups are also particularly preferred including fluoroalkyl having 1, 2, 3 or 4 carbon atoms such as trifluoromethyl and fluoro-substituted alkoxy having 1, 2, 3 or 4 carbon atoms such as trifluoromethoxy (—$OCF_3$). Methylthio (—$SCH_3$) and ethylthio (—$SCH_2CH_3$) are also particularly preferred phenyl ring substituents.

Particularly preferred R and $R^1$ groups of Formula IV include phenyl substituted at least at the 2,5 ring positions. For example, preferred are the following compounds of Formula IVa:

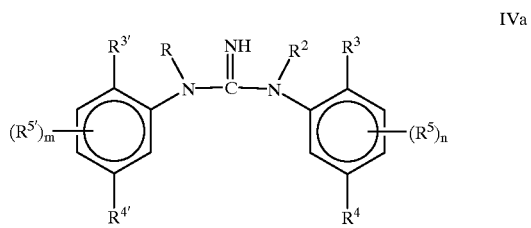

IVa wherein R and $R^2$ are the same as defined above for Formula IV; each $R^3$, $R^4$, $R^5$, $R^{3'}$, $R^{4'}$ and $R^{5'}$ substituent is independently selected from the same group of substituents as defined above for $R^3$–$R^5$ of Formula IV; m and n are each independently 0 ($R^5$ and $R^{5'}$ are hydrogen when m and n are respectively 0), 1, 2 or 3; and pharmaceutically acceptable salts thereof. Preferred compounds of Formula IVa include those compounds where at least one of R and $R^2$ is other than heterocyclic aryl or carbocyclic aryl, e.g. where at least one of R and $R^2$ is hydrogen or substituted or unsubstituted alkyl, particularly substituted or unsubstituted alkyl having 1, 2, 3 or 4 carbon atoms. Preferred values of m and n of Formula IVa are 0 and 1.

Further preferred compounds of Formula IV include those compounds where the value n equals 1, particularly where n equals 1 and the phenyl ring is substituted by a $R^5$ group at the 3- or 4-position, i.e. the phenyl ring is 2,3,5-substituted or 2,4,5-substituted.

Especially preferred compounds of Formula IV are those where n is equal to zero (i.e., the 3, 4 and 6 positions of the phenyl ring are hydrogen-substituted), specifically compounds of the following Formula IVb:

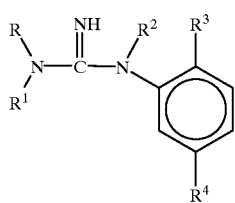

IVb where the groups R through $R^4$ are the same as specified above for Formula IV; and pharmaceutically acceptable salts thereof. Particularly preferred compounds of Formula IVb include those compounds where R is substituted or unsubstituted heterocyclic aryl or substituted or unsubstituted carbocyclic aryl such as substituted or unsubstituted phenyl or naphthyl and where at least one of $R^1$ and $R^2$ is other than heterocyclic aryl or carbocyclic aryl, e.g. where at least one of $R^1$ and $R^2$ is hydrogen or substituted or unsubstituted alkyl, particularly substituted or unsubstituted alkyl having 1, 2, 3 or 4 carbon atoms.

A still further group of preferred compounds of the invention have, in addition to a 2,5-substituted phenyl moiety, at least one guanidine substituent (i.e., R, $R^1$ or $R^2$ of Formula IV) that is a phenyl group substituted at the 3-position, preferably without substitution at other ring positions. Particularly preferred are N-(3-substituted phenyl)-N'-(2,5-disubstituted phenyl)guanidines of the following Formula IVc:

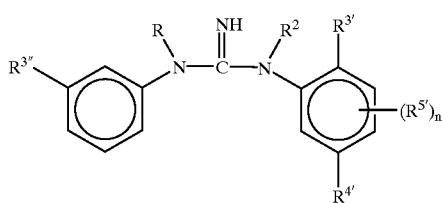

IVc wherein R, $R^2$ and n are the same as defined above for Formula IV; each $R^{3'}$, $R^{4'}$, $R^{5'}$ and $R^{3''}$ substituent is independently selected from the same group of substituents as defined above for $R^3$, $R^4$ and $R^5$ for Formula IV; and pharmaceutically salts of said compounds. Preferred compounds of Formula IVc include those compounds where at least one of R and $R^2$ is other than heterocyclic aryl or carbocyclic aryl, e.g. where at least one of R and $R^2$ is hydrogen or substituted or unsubstituted alkyl, particularly substituted or unsubstituted alkyl having 1 to about 4 carbon atoms. Especially preferred are compounds of Formula IVc are those where one of R and $R^2$ is hydrogen and the other is substituted or unsubstituted alkyl having 1, 2, 3 or 4 carbon atoms, more preferably where R is methyl, ethyl or propyl and $R^2$ is hydrogen. Preferred values of n of Formula IVc are 0 and 1.

Specifically preferred compounds of Formula IV for use in the present methods include N-(3-ethylphenyl)-N,N'-dimethyl-N'-(2,5-dichlorophenyl)guanidine; N-(3-ethylphenyl)-N-methyl-N'-(2,5-dichlorophenyl)guanidine; N-(3-ethylphenyl)-N'-(2,5-dichlorophenyl)-N'-methylguanidine; N-(3-ethylphenyl)-N'-(2,5-dichlorophenyl)guanidine; N-(3-ethylphenyl)-N-methyl-N'-(2,5-dibromophenyl)guanidine; N-(3-ethylphenyl)-N'-(2,5-dibromophenyl)-N'-methylguanidine; N-(3-ethylphenyl)-N'-(2,5-dibromophenyl)guanidine; N-(3-ethylphenyl)-N-methyl-N'-(2-chloro-5-trifluoromethylphenyl)guanidine; N-(3-ethylphenyl)-N'-(2-chloro-5-trifluoromethylphenyl)guanidine; N-(3-ethylphenyl)-N,N'-dimethyl-N'-(2-bromo-5-trifluoromethyl)guanidine; N-(3-ethylphenyl)-N-methyl-N'-(2-bromo-5-trifluromethylphenyl)guanidine; N-(3-ethylphenyl)-N'-(2-bromo-5-trifluoromethylphenyl)guanidine; N-(3-ethylphenyl)-N-methyl-N'-(2-fluoro-5-trifluromethylphenyl)guanidine; N-(3-ethylphenyl)-N'-(2-fluoro-5-trifluoromethylphenyl)guanidine; N-(3-ethylphenyl)-N,N'-dimethyl-N'-(2-chloro-5-ethylphenyl)guanidine; N-(3-ethylphenyl)-N-methyl-N'-(2-chloro-5-ethylphenyl)guanidine; N-(3-ethylphenyl)-N'-(2-chloro-5-ethylphenyl)guanidine; N-(3-ethylphenyl)-N,N'-dimethyl-N'-(2-bromo-5-ethylphenyl)guanidine; N-(3-ethylphenyl)-N-methyl-N'-(2-bromo-5-ethylphenyl)guanidine; N-(3-ethylphenyl)-N'-(2-bromo-5-ethylphenyl)guanidine; N-(3-ethylphenyl)-N,N'-dimethyl-N'-(2-fluoro-5-ethylphenyl)guanidine; N-(3-ethylphenyl)-N-methyl-N'-(2-fluoro-5-ethylphenyl)guanidine; N-(3-ethylphenyl)-N'-(2-fluoro-5-ethylphenyl)guanidine; N-(3-ethylphenyl)-N,N'-dimethyl-N'-(2-chloro-5-methylphenyl); N-(3-ethylphenyl)-N-methyl-N'-(2-chloro-5-methylphenyl)guanidine; N-(3-ethylphenyl)-N'-(2-chloro-5-ethylphenyl)guanidine; N-(3-ethylphenyl)-N'-(2-chloro-5-methylphenyl)guanidine; N-(3-ethylphenyl)-N-methyl-N'-(2-chloro-5-methylthio)guanidine; N-(3-ethylphenyl)-N'-(2-chloro-5-methylthio)guanidine; N-(1-naphthyl)-N'-(2-bromo-5-ethylphenyl)guanidine; N-(1-naphthyl-N'-(2-fluoro-5-ethylphenyl)guanidine; N-(1-naphthyl)-N'-(2,5-dichlorophenyl)guanidine; N-(1-naphthyl)-N'-(2-fluoro-5-methylphenyl)guanidine; N-(3-ethylphenyl)-N-methyl-N'-(2,4,5-trichlorophenyl)guanidine; N-(3-ethylphenyl)-N'-(2,4,5-trichlorophenyl)guanidine; N-(3-ethylphenyl)-N-methyl-N'-(2,3,5-trichlorophenyl)guanidine; N-(3-ethylphenyl)-N'-(2,3,5-trichlorophenyl)guanidine; N-(1-naphthyl)-N'-(2,4,5-trichlorophenyl)guanidine; N-(1-naphthyl)-N'-(2,3,5-trichlorophenyl)guanidine; N-(1-naphthyl)-N'-(2,5-dichlorophenyl)-N'-methylguanidine; N-(1-naphthyl)-N'-(2-chloro-5-methylphenyl)guanidine; N-(1-naphthyl)-N'-(2,5-dimethylphenyl)guanidine; N-(1-naphthyl)-N'-(2,5-dibromophenyl)guanidine; N-(1-naphthyl)-N'-(2-chloro-5-methylphenyl)-N'-methylguanidine; N-(1-naphthyl)-N'-(2-5-dimethylphenyl)-N'-methylguanidine; N-(1-naphthyl)-N'-(2,5-dibromophenyl)-N-methylguanidine; N-(1-naphthyl)-N'-(2,5-dibromophenyl)-N'-methylguanidine; N-(1-naphthyl)-N'-(2-chloro-5-thiomethylphenyl)guanidine; N-(1-naphthyl)-N'-(2-fluoro-5-trifluoromethylphenyl)

guanidine; N-(1-naphthyl)-N'-(2-chloro-5-trifluoromethylphenyl)guanidine; N-(1-naphthyl)-N'-(2-bromo-5-trifluoromethylphenyl)guanidine; N-(1-naphthyl)-N'-(2-thiomethyl-5-trifluoromethylphenyl)guanidine; N-(1-naphthyl)-N'-(2-methoxy-5-methylphenyl)guanidine; N-(1-naphthyl)-N'-(2-chloro-5-ethylphenyl)guanidine; N-(1-naphthyl)-N'-(2-chloro-5-ethylphenyl)-N'-methylguanidine; N-(1-naphthyl)-N'-methyl-N'-(2-chloro-5-thiomethylphenyl)guanidine; N-(8-quinolinyl)-N'-(2-chloro-5-methylphenyl)guanidine; N-(8-quinolinyl)-N'-(2-chloro-5-ethylphenyl)guanidine; N-(8-quinolinyl)-N'-methyl-(2-chloro-5-ethylphenyl)guanidine; N-(3-methylthiophenyl)-N-methyl-N'-(2-chloro-5-methylthiophenyl)guanidine; N-(3-methylthiophenyl)-N'-methyl-N'-(2-chloro-5-methylthiophenyl)guanidine; N-(3-methylthiophenyl)-N'-(2-chloro-5-methylthiophenyl)guanidine; N-(3-methylthiophenyl)-N-methyl-N'-(2-chloro-5-ethylphenyl)guanidine; N-(3-methylthiophenyl)-N'-methyl-N'-(2-chloro-5-ethylphenyl)guanidine; N-(3-methylthiophenyl)-N'-(2-chloro-5-ethylphenyl)guanidine; N-(3-methylthiophenyl)-N-methyl-N'-(2-bromo-5-ethylphenyl)guanidine; N-(3-methylthiophenyl)-N'-methyl-N'-(2-bromo-5-ethylphenyl)guanidine; N-(3-methylthiophenyl)-N'-(2-bromo-5-ethylphenyl)guanidine; N-(3-methylthiophenyl-N-methyl-N'-(2,5-dichlorophenyl)guanidine; N-(3-methylthiophenyl-N'-methyl-N'-(2,5-dichlorophenyl)guanidine; N-(3-methylthiophenyl)-N'-(2,5-dichlorophenyl)guanidine; N-(3-methylthiophenyl)-N-methyl-N'-(2,5-dibromophenyl)guanidine; N-(3-methylthiophenyl)-N'-methyl-N'-(2,5-dibromophenyl)guanidine; N-(3-methylthiophenyl)-N'-(2,5-dibromophenyl)guanidine; N-(3-trifluoromethylphenyl)-N-methyl-N'-(2-chloro-5-methylthiophenyl)guanidine; N-(3-trifluoromethylphenyl)-N'-methyl-N'-(2-chloro-5-methylthiophenyl)guanidine; N-(3-trifluoromethylphenyl)-N'-(2-chloro-5-methylthiophenyl)guanidine; N-(3-trifluoromethylphenyl)-N-methyl-N'-(2-chloro-5-ethylphenyl)guanidine; N-(3-trifluoromethylphenyl)-N'-methyl-N'-(2-chloro-5-ethylphenyl)guanidine; N-(3-trifluoromethylphenyl)-N'-(2-chloro-5-ethylphenyl)guanidine; N-(3-trifluoromethylphenyl)-N-methyl-N'-(2-bromo-5-ethylphenyl)guanidine; N-(3-trifluoromethylphenyl)-N'-methyl-N'-(2-bromo-5-ethylphenyl)guanidine; N-(3-trifluoromethylphenyl)-N'-(2-bromo-5-ethylphenyl)guanidine; N-(3-trifluoromethylphenyl)-N-methyl-N'-(2,5-dichlorophenyl)guanidine; N-(3-trifluoromethylphenyl)-N'-methyl-N'-(2,5-dichlorophenyl)guanidine; N-(3-trifluoromethylphenyl)-N'-(2,5-dichlorophenyl)guanidine; N-(3-trifluoromethylphenyl)-N-methyl-N'-(2,5-dibromophenyl)guanidine; N-(3-trifluoromethylphenyl)-N'-methyl-N'-(2,5-dibromophenyl)guanidine; N-(3-trifluoromethylphenyl)-N'-(2,5-dibromophenyl)guanidine; N-(3-ethylphenyl)-N-methyl-N'-(2-bromo-5-methylthiophenyl)guanidine; N-(3-ethylphenyl)-N'-methyl-N'-(2-bromo-5-methylthiophenyl)guanidine; N-(3-ethylphenyl)-N'-(2-bromo-5-methylthiophenyl)guanidine; N-(3-methylthiophenyl)-N-methyl-N'-(2-bromo-5-methylthiophenyl)guanidine; N-(3-methylthiophenyl)-N'-methyl-N'-(2-bromo-5-methylthiophenyl)guanidine; N-(3-methylthiophenyl)-N'-(2-bromo-5-methylthiophenyl)guanidine; N-(3-methylthiophenyl)-N-methyl-N'-(2-bromo-5-ethylphenyl)guanidine; N-(3-methylthiophenyl)-N'-methyl-N'-(2-bromo-5-ethylphenyl)guanidine; N-(3-methylthiophenyl)-N'-(2-bromo-5-ethylphenyl)guanidine; N-(3-trifluoromethylphenyl)-N-methyl-N'-(2-bromo-5-methylthiophenyl)guanidine; N-(3-trifluoromethylphenyl)-N'-methyl-N'-(2-bromo-5-methylthiophenyl)guanidine; N-(3-trifluoromethylphenyl)-N'-(2-bromo-5-methylthiophenyl)guanidine; N-(3-bromophenyl)-N-methyl-N'-(2-chloro-5-methylthiophenyl)guanidine; N-(3-bromophenyl)-N'-methyl-N'-(2-chloro-5-methylthiophenyl)guanidine; N-(3-bromophenyl)-N'-(2-chloro-5-methylthiophenyl)guanidine; N-(3-trifluoromethoxyphenyl)-N-methyl-N'-(2,5-dibromophenyl)guanidine; N-(3-trifluoromethoxyphenyl)-N'-methyl-N'-(2,5-dibromophenyl)guanidine; N-(3-trifluoromethoxyphenyl)-N'-(2,5-dibromophenyl)guanidine; N-(3-trifluoromethoxyphenyl)-N-methyl-N'-(2-bromo-5-ethylphenyl)guanidine; N-(3-trifluoromethoxyphenyl)-N'-methyl-N'-(2-bromo-5-ethylphenyl)guanidine; N-(3-trifluoromethoxyphenyl)-N'-(2-bromo-5-ethylphenyl)guanidine; N-(3-iodophenyl)-N-methyl-N'-(2-chloro-5-methylthiophenyl)guanidine; N-(3-iodophenyl)-N'-methyl-N'-(2-chloro-5-methylthiophenyl)guanidine; N-(3-iodophenyl)-N'-(2-chloro-5-methylthiophenyl)guanidine; N-(3-iodophenyl)-N-methyl-N'-(2-chloro-5-ethylphenyl)guanidine; N-(3-iodophenyl)-N'-methyl-N'-(2-chloro-5-ethylphenyl)guanidine; N-(3-iodophenyl)-N'-(2-chloro-5-ethylphenyl)guanidine; N-(3-ethylphenyl)-N'-(2-chloro-5-ethylthiophenyl)guanidine; N-(3-ethylphenyl)-N-methyl-N'-(2-chloro-5-ethylthiophenyl)guanidine; N-(3-ethylphenyl)-N'-methyl-N'-(2-chloro-5-ethylthiophenyl)guanidine; N-(3-ethylphenyl)-N,N'-dimethyl-N'-(2-chloro-5-ethylthiophenyl)guanidine; N-(3-ethylphenyl)-N'-(2-bromo-5-ethylthiophenyl)guanidine; N-(3-ethylphenyl)-N-methyl-N'-(2-bromo-5-ethylthiophenyl)guanidine; N-(3-ethylphenyl)-N'-methyl-N'-(2-bromo-5-ethylthiophenyl)guanidine; N-(3-ethylphenyl)-N,N'-dimethyl-N'-(2-bromo-5-ethylthiophenyl)guanidine; N-(3-methylthiophenyl)-N'-(2-chloro-5-ethylthiophenyl)guanidine; N-(3-methylthiophenyl)-N-methyl-N'-(2-chloro-5-ethylthiophenyl)guanidine; N-(3-methylthiophenyl)-N'-methyl-N'-(2-chloro-5-ethylthiophenyl)guanidine; N-(3-methylthiophenyl)-N,N'-dimethyl-N'-(2-chloro-5-ethylthiophenyl)guanidine; N-(3-methylthiophenyl)-N'-(2-bromo-5-ethylthiophenyl)guanidine; N-(3-methylthiophenyl)-N-methyl-N'-(2-bromo-5-ethylthiophenyl)guanidine; N-(3-methylthiophenyl)-N'-methyl-N'-(2-bromo-5-ethylthiophenyl)guanidine; N-(3-methylthiophenyl)-N,N'-dimethyl-N'-(2-bromo-5-ethylthiophenyl)guanidine; N-(3-trifluoromethylphenyl)-N'-(2-chloro-5-ethylthiophenyl)guanidine; N-(3-trifluoromethylphenyl)-N-methyl-N'-(2-chloro-5-ethylthiophenyl)guanidine; N-(3-trifluoromethylphenyl)-N'-methyl-N'-(2-chloro-5-ethylthiophenyl)guanidine; N-(3-trifluoromethylphenyl)-N,N'-dimethyl-N'-(2-chloro-5-ethylthiophenyl)guanidine; N-(3-trifluoromethylphenyl)-N'-(2-bromo-5-ethylthiophenyl)guanidine; N-(3-trifluoromethylphenyl)-N-methyl-N'-(2-bromo-5-ethylthiophenyl)guanidine; N-(3-trifluoromethylphenyl)-N'-methyl-N'-(2-bromo-5-ethylthiophenyl)guanidine; N-(3-trifluoromethylphenyl)-N,N'-dimethyl-N'-(2-bromo-5-ethylthiophenyl)guanidine; N-(3-ethylphenyl)-N'-(2-chloro-5-trifluoromethylthiophenyl)guanidine; N-(3-ethylphenyl)-N-methyl-N'-(2-chloro-5-trifluoromethylthiophenyl)guanidine; N-(3-ethylphenyl)-N'-methyl-N'-(2-chloro-5-trifluoromethylthiophenyl)guanidine; N-(3-ethylphenyl)-N,N'-dimethyl-N'-(2-chloro-5-trifluoromethyl thiophenyl)guanidine; N-(3-ethylphenyl)-N'-(2-bromo-5-trifluoromethylthiophenyl)guanidine; N-(3-ethylphenyl)-N-methyl-N'-(2-bromo-5-trifluoromethylthiophenyl)guanidine; N-(3-ethylphenyl)-N'-methyl-N'-(2-bromo-5-trifluoromethyl thiophenyl)guanidine; N-(3-ethylphenyl)-N, N'-dimethyl-N'-(2-bromo-5-trifluoromethyl thiophenyl) guanidine; N-(3-methylthiophenyl)-N'-(2-chloro-5-trifluoromethylthiophenyl)guanidine; N-(3-methylthiophenyl)-N-methyl-N'-(2-chloro-5-trifluoromethylthiophenyl)guanidine; N-(3-methylthiophenyl)-N'-methyl-N'-(2-chloro-5-trifluoromethylthiophenyl)guanidine; N-(3-methylthiophenyl)-N,N'-dimethyl-N'-(2-chloro-5-trifluoromethylthiophenyl)guanidine; N-(3-methylthiophenyl)-N'-(2-bromo-5-trifluoromethylthiophenyl)guanidine; N-(3-methylthiophenyl)-N-methyl-N'-(2-bromo-5-trifluoromethylthiophenyl)guanidine; N-(3-methylthiophenyl)-N'-methyl-N'-(2-bromo-5-trifluoromethylthiophenyl)guanidine; N-(3-methylthiophenyl)-N,N'-dimethyl-N'-(2-bromo-5-trifluoromethylthiophenyl)guanidine; N-(3-trifluoromethylphenyl)-N'-(2-chloro-5-trifluoromethylthiophenyl)guanidine; N-(3-trifluoromethylphenyl)-N-methyl-N'-(2-chloro-5-trifluoromethylthiophenyl)guanidine; N-(3-trifluoromethylphenyl)-N'-methyl-N'-(2-chloro-5-trifluoromethylthiophenyl)guanidine; N-(3-trifluoromethylphenyl)-N,N'-dimethyl-N'-(2-chloro-5-trifluoromethylthiophenyl)guanidine; N-(3-trifluoromethylphenyl)-N'-(2-bromo-5-trifluoromethylthiophenyl)guanidine; N-(3-trifluoromethylphenyl)-N-methyl-N'-(2-bromo-5-trifluoromethylthiophenyl)guanidine; N-(3-trifluoromethylphenyl)-N'-methyl-N'-(2-bromo-5-trifluoromethylthiophenyl)guanidine; N-(3-trifluoromethylphenyl)-N,N'-dimethyl-N'-(2-bromo-5-trifluoromethylthiophenyl)guanidine; N-(1-naphthyl)-N'-(2-chloro-5-methylthiophenyl)guanidine; N-(1-naphthyl)-N'-(2-iodo-5-methylthiophenyl)guanidine; N-(1-naphthyl)-N'-(2-bromo-5-methylthiophenyl)guanidine; N-(3-methylsulfonylphenyl)-N-methyl-N'-(2,5-dibromophenyl)guanidine; N-(3-methylsulfonylphenyl)-N'-(2,5-dibromophenyl)guanidine; N-(3-methylsulfinylphenyl)-N-methyl-N'-(2,5-dibromophenyl)guanidine; N-(3-methylsulfinylphenyl)-N'-(2,5-dibromophenyl)guanidine; and pharmaceutically acceptable salts of said compounds.

Preferred compounds of the above Formulae I through III also include those having a substituent of carbocyclic aryl with at least 6 ring carbons, particularly phenyl, and substituted at one or more ring positions by haloalkyl, substituted or unsubstituted thioalkyl having from 1 to about 3 carbon atoms, substituted or unsubstituted alkylsulfinyl, substituted or unsubstituted alkylsulfonyl and haloalkyl. Specifically preferred compounds include N-(1-naphthyl)-N'-(3-methylthiophenyl)-N'-methylguanidine; N-(1-naphthyl)-N-methyl-N'-(3-methylthiophenyl)guanidine; N-(1-naphthyl)-N,N'-dimethyl-N'-(3-methylthiophenyl)guanidine; N-(1-naphthyl)-N'-(3-methylthiophenyl)guanidine; N-(1-naphthyl)-N'-(3-methylsulfinylphenyl)-N'-methylguanidine; N-(1-naphthyl)-N-methyl-N'-(3-methylsulfinylphenyl)guanidine; N-(1-naphthyl)-N,N'-dimethyl-N'-(3-methylsulfinylphenyl)guanidine; N-(1-naphthyl)-N'-(3-methylsulfinylphenyl)guanidine; N-(1-naphthyl)-N'-(3-methylsulfonylphenyl)-N'-methylguanidine; N-(1-naphthyl)-N-methyl-N'-(3-methylsulfonylphenyl)guanidine; N-(1-naphthyl)-N,N'-dimethyl-N'-(3-methylsulfonylphenyl)guanidine; N-(1-naphthyl)-N'-(3-methylsulfonylphenyl)guanidine; N-(1-naphthyl)-N'-(3-trifluoromethylthiophenyl)-N'-methylguanidine; N-(1-naphthyl)-N-methyl-N'-(3-trifluoromethylthiophenyl)guanidine; N-(1-naphthyl)-N,N'-dimethyl-N'-(3-trifluoromethylthiophenyl)guanidine; N-(1-naphthyl)-N'-(3-trifluoromethylthiophenyl)guanidine; N-(1-naphthyl)-N'-(3-pentafluoroethylphenyl)-N'-methylguanidine; N-(1-naphthyl)-N-methyl-N'-(3-pentafluoroethylphenyl)guanidine; N-(1-naphthyl)-N,N'-dimethyl-N'-(3-pentafluoroethylphenyl)guanidine; N-(1-naphthyl)-N'-(3-pentafluoroethylphenyl)guanidine; N-(1-naphthyl)-N'-(3-trifluoromethoxyphenyl)-N'-methylguanidine; N-(1-naphthyl)-N-methyl-N'-(3-trifluoromethoxyphenyl)-N'-methylguanidine; N-(1-naphthyl)-N'-(3-trifluoromethoxyphenyl)guanidine; N-(3-ethylphenyl)-N'-(3-methylthiophenyl)-N'-methylguanidine; N-(3-ethylphenyl)-N,N'-dimethyl-N'-(3-methylthiophenyl)guanidine; N-(3-ethylphenyl)-N'-(3-methylthiophenyl)guanidine; N-(3-ethylphenyl)-N'-(3-methylsulfinylphenyl)-N'-methylguanidine; N-(3-ethylphenyl)-N,N'-dimethyl-N'-(3-methylsulfinylphenyl)guanidine; N-(3-ethylphenyl)-N'-(3-methylsulfinylphenyl)guanidine; N-(3-ethylphenyl)-N'-(3-methylsulfonylphenyl)-N'-methylguanidine; N-(3-ethylphenyl)-N,N'-dimethyl-N'-(3-methylsulfonylphenyl)guanidine; N-(3-ethylphenyl)-N'-(3-methylsulfonylphenyl)guanidine; N-(3-ethylphenyl)-N'-(3-trifluoromethylthiophenyl)-N'-methylguanidine; N-(3-ethylphenyl)-N-methyl-N'-(3-trifluoromethylthiophenyl)guanidine; N-(3-ethylphenyl)-N,N'-dimethyl-N'-(3-trifluoromethylthiophenyl)guanidine; N-(3-ethylphenyl)-N'-(3-trifluoromethylthiophenyl)guanidine; N-(3-ethylphenyl)-N'-(3-pentafluoroethylphenyl)-N'-methylguanidine; N-(3-ethylphenyl)-N-methyl-N'-(3-pentafluoroethylphenyl)guanidine; N-(3-ethylphenyl)-N-methyl-N'-(3-pentafluoroethylphenyl)-N'-methylguanidine; N-(3-ethylphenyl)-(3-pentafluoroethylphenyl)guanidine; N-(3-ethylphenyl)-N'-(3-trifluoromethylphenyl)-N'-methylguanidine; N-(3-ethylphenyl)-N-methyl-N'-(3-trifluoromethoxyphenyl)guanidine; N-(3-ethylphenyl)-N-methyl-N'-(3-trifluoromethoxyphenyl)-N'-methylguanidine; N-(3-ethylphenyl)-N-methyl-N'-(3-trifluoromethoxyphenyl)guanidine; N-(3-ethylphenyl)-N'-(3-trifluoromethoxyphenyl)guanidine; N-(3-methylthiophenyl)-N'-(3-methylthiophenyl)guanidine; N-(3-methylthiophenyl)-N'-(3-methylthiophenyl)-N'-methylguanidine; N-(3-methylthiophenyl)-N-methyl-N'-(3-methylthiophenyl)guanidine; N-(3-methylthiophenyl)-N,N'-dimethyl-N'-(3-methylthiophenyl)guanidine; N-(3-methylthiophenyl)-N'-(3-bromophenyl)guanidine; N-(3-methylthiophenyl )-N'-(3-bromophenyl)-N'-methylguanidine; N-(3-methylthiophenyl)-N-methyl-N'-(3-bromophenyl)guanidine; N-(3-methylthiophenyl)-N,N'-dimethyl-N'-(3-bromophenyl)guanidine; N-(3-ethylphenyl)-N,N'-dimethyl(3-trifluoromethylphenyl)guanidine; N-(3-ethylphenyl)-N-methyl-N'-(3-trifluoromethylphenyl)guanidine; N-(3-ethylphenyl)-N'-(3-trifluoromethylphenyl)-N'-methylguanidine; N-(1-naphthyl)-N'-(3-trifluoromethylphenyl)-N-methylguanidine; N-(1-naphthyl)-N'-(3-trifluoromethylphenyl)-N,N'-dimethylguanidine; and pharmaceutically acceptable salts thereof.

Compounds of having an acenaphthyl or acenaphthylene substituent are also preferred for use in the methods of the invention, include compounds of the following Formula V:

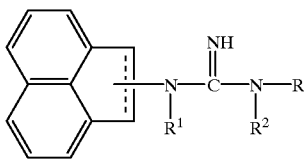

V wherein R is cycloalkyl of 3 to 12 carbon atoms, e.g., cyclopropyl, cyclopentyl, cyclohexyl, cyclohexenyl, cycloheptyl, 1,4-methylenecyclohexyl, 1- or 2-adamantyl, exo or endo 2-norbornyl, exo or endo 2-isobornyl, menthyl, cyclopentylmethyl, cyclohexylmethyl, 1- or 2-cyclohexylethyl and 1-, 2- or 3-cyclohexylpropyl; carbocyclic aryl, alkaryl, aralkyl or heterocyclic, e.g., of 6 to 18 carbon atoms and containing 1–3 separate or fused rings, and 0–5 O, N and/or S ring atoms in an aryl, alicyclic or mixed ring system, e.g., phenyl, benzyl, 1- and 2-phenylethyl, 1-, 2-, or 3-phenylpropyl; o-, m-, or p-tolyl, m,m'-dimethylphenyl, o-, m-, or p-ethylphenyl, m,m'-diethylphenyl, m-methyl-m'-ethylphenyl and o-propylphenyl, 1-naphthyl, 2-naphthyl, biphenyl; indanyl, for example, 4-indanyl; indenyl, for example, 1- or 4-indenyl; 3-acenaphthyl, 5-acenaphthyl; 3-acenaphthylene, 5-acenaphthylene; indolyl, for example, 7-indolyl; benzthiazole, quinolinyl, isoquinolinyl, pyridyl, pyrimidinyl, pyrazinyl, furanyl, thienyl, pyrrolyl, thiazolyl, oxazolyl, coumarinyl, or imidazolyl;

$R^1$ and $R^2$ are the same or different and selected from the group consisting of hydrogen, lower $C_{1-6}$ alkyl, lower $C_{1-6}$ alkylamino, $C_{5-10}$ aryl or substituted aryl;

wherein R and the acenaphthyl group are optionally substituted by hydroxy, acetate, oxo, amino, lower $C_{1-6}$ alkyl, lower $C_{1-6}$ alkyl amino, alkoxy of 1–6 carbon atoms, di-lower $C_{2-12}$ alkyl amino, nitro, azido, sulfhydryl, cyano, isocyanato, halogen, amido, sulfonato or carbamido.

Particularly preferred compounds within the scope of general Formula V include N,N'-di-(1-acenaphthyl) guanidine; N,N'-di-(3-acenaphthyl)guanidine; N,N'-di-(5-acenaphthyl)guanidine; N,N'-di-(acenaphthylen-1-yl) guanidine; N-(adamantan-1-yl)-N'-( 5-acenaphthyl) guanidine; N-(adamantan-2-yl)-N-(5-acenaphthyl) guanidine; N-(adamantan-1-yl)-N-(3-acenaphthyl) guanidine; N-(adamantan-2-yl)-N'-(3-acenaphthyl) guanidine; N-(adamant-1-yl)-N'-(adamant-2-yl)guanidine; N-(3-acenaphthyl)-N'-(4-fluoronaphthyl)guanidine; N-(5-acenaphthyl)-N'-(4-fluoronaphthyl)guanidine; N-(3-acenaphthyl)-N'-(4-hydroxynaphthyl)guanidine; N-(5-acenaphthyl)-N'-(4-hydroxynaphthyl)guanidine; N-(3-acenaphthyl)-N'-(4-methoxynaphthyl)guanidine; N-(5-acenaphthyl)-N'-(4-methoxynaphthyl)guanidine; N-(3-acenaphthyl)-N'-(4-nitronaphthyl)guanidine; N-(5-acenaphthyl)-N'-(4-nitronaphthyl)guanidine; N-(3-acenaphthyl)-N'-(4-aminonaphthyl)guanidine; N-(5-acenaphthyl)-N'-(4-aminonaphthyl)guanidine; N-(3-acenaphthyl)-N'-(4-azidonaphthyl)guanidine; N-(5-acenaphthyl)-N'-(4-azidonaphthyl)guanidine; N-(3-acenaphthyl)-N'-(4-bromonaphthyl)guanidine; N-(3-acenaphthyl)-N'-(4-bromonaphthyl)guanidine; N-(5-acenaphthyl)-N-(4-cyanonaphthyl)guanidine; N-(3-acenaphthyl)-N-(4-cyanonaphthyl)guanidine; N-(5-acenaphthyl)-N'-(4-amidonaphthyl)guanidine; N-(3-acenaphthyl)-N'-(4-amidonaphthyl)guanidine; N-(3-acenaphthyl)-(4-iodonaphthyl)guanidine; N-(5-acenaphthyl)-(4-iodonaphthyl)guanidine; N-(3-acenaphthyl)-N'-(7-fluoronaphthyl)guanidine; N-(5-acenaphthyl)-N'-(7-fluoronaphthyl)guanidine; N-(3-acenaphthyl)-N'-(2-fluoronaphthyl)guanidine; N-(5-acenaphthyl)-N'-(2-fluoronaphthyl)guanidine; N-(3-acenaphthyl)-N'-(2-methoxynaphthyl)guanidine; N-(5-acenaphthyl)-N'-(2-methoxynaphthyl)guanidine; N-(3-acenaphthyl)-N'-(2-hydroxynaphthyl)guanidine; N-(5-acenaphthyl)-N'-(2-hydroxynaphthyl)guanidine; N-(3-acenaphthyl)-N'-(2-aminonaphthyl)guanidine; N-(5-acenaphthyl)-N'-(2-aminonaphthyl)guanidine; N-(3-acenaphthyl)-N'-(4-isopropylphenyl)guanidine; N-(5-acenaphthyl)-N'-(4-isopropylphenyl)guanidine; N-(3-acenaphthyl)-N'-(4n-propylphenyl)guanidine; N-(5-acenaphthyl)-N'-(4n-propylphenyl)guanidine; N-(3-acenaphthyl)-N-(2-isopropylphenyl)guanidine; N-(5-acenaphthyl)-N-(2-isopropylphenyl)guanidine; N-(3-acenaphthyl)-N-(4-cyclopropylphenyl)guanidine; N-(5-acenaphthyl)-N-(4-cyclopropylphenyl)guanidine; N-(3-acenaphthyl)-N'-(coumarinyl)guanidine; N-(5-acenaphthyl)-N'-(coumarinyl)guanidine; N-(3-acenaphthyl)-N'-(quinolinyl)guanidine; N-(5-acenaphthyl)-N'-(quinolinyl)guanidine; N-(4-hydroxy-3-acenaphthyl)-N'-(adamant-1yl)guanidine; N-(4-hydroxy-3-acenaphthyl)-N'-(adamant-2-yl)guanidine; N-(4-hydroxy-5-acenaphthyl)-N'-(adamant-1-yl)guanidine; N-(4-hydroxy-5-acenaphthyl)-N'-(adamant-2-yl)guanidine; N-(4-nitro-5-acenaphthyl)-N'-(adamant-1-yl)guanidine; N-(4-nitro-5-acenaphthyl)-N'-(adamant-2-yl)guanidine; N-(4-amino-3-acenaphthyl)-N'-(adamant-1-yl)guanine; N-(4-amino-3-acenaphthyl)-N'-(adamant-2-yl)guanidine; N-(4-amino-5-acenaphthyl)-N'-(adamant-1-yl)guanidine; N-(4-amino-5-acenaphthyl)-N'-(adamant-2-yl)guanidine; N-(4-methoxy-3-acenaphthyl)-N'-(adamant-1-yl)guanidine; N-(4-methoxy-3-acenaphthyl)-N'-(adamant-2-yl)guanidine; N-(4-methoxy-5-acenaphthyl)-N'-(adamant-1-yl)guanidine; N-(4-methoxy-5-acenaphthyl)-N'-(adamant-2-yl)guanidine; N-(4-bromo-3-acenaphthyl)-N'-(adamant-1-yl)guanidine; N-(4-bromo-3-acenaphthyl)-N'-(adamant-2-yl)guanidine, N-(4-bromo-5-acenaphthyl)-N'-(adamant-1-yl)guanidine; N-(4-bromo-5-acenaphthyl)-N'-(adamant-2-yl)guanidine; N-(1-oxo-3-acenaphthyl)-N'-(adamant-1-yl)guanidine; N-(1-oxo-3-acenaphthyl)-N'-(adamant-2-yl)guanidine; N-(1-oxo-5-acenaphthyl)-N'-(adamant-1-yl)guanidine; N-(1-oxo-5-acenaphthyl)-N'-(adamant-2-yl)guanidine; N-(2-oxo-3-acenaphthyl)-N'-(adamant-1-yl)guanidine; N-(2-oxo-3-acenaphthyl)-N'-(adamant-2-yl)guanidine; N-(2-oxo-5-acenaphthyl)-N'-(adamant-1-yl)guanidine; N-(2-oxo-5-acenaphthyl)-N'-(adamant-2-yl)guanidine; N-(1-bromo-3-acenaphthyl)-N'-(adamant-1-yl)guanidine; N-(1-bromo-3-acenaphthyl)-N'-(adamant-2-yl)guanidine; N-(1-bromo-5-acenaphthyl)-N'-(adamant-1-yl)guanidine; N-(1-bromo-5-acenaphthyl)-N'-(adamant-2-yl)guanidine; N-(2-bromo-3-acenaphthyl)-N'-(adamant-2-yl)guanidine; N-(2-bromo-3-acenaphthyl)-N'-(adamant-2-yl)guanidine; N-(2-bromo-5-acenaphthyl)-N'-(adamant-1-yl)guanidine; N-(2-bromo-5-acenaphthyl)-N'-(adamant-2-yl)guanidine; N-(1-hydroxy-3-acenaphthyl)-N'-(adamant-1-yl)guanidine; N-(1-hydroxy-3-acenaphthyl)-N'-(adamant-2-yl)guanidine; N-(1-hydroxy-5-acenaphthyl)-N'-(adamant-1-yl)guanidine; N-(1-hydroxy-5-acenaphthyl)-N'-(adamant-2-yl)guanidine; N-(2-hydroxy-3-acenaphthyl)-N'-(adamant-1-yl)guanidine; N-(2-hydroxy-3-acenaphthyl)-N'-(adamant-2-yl)guanidine; N-(2-hydroxy-5-acenaphthyl)-N'-(adamant-1-yl)guanidine; N-(2-hydroxy-5-acenaphthyl)-N'-(adamant-2-yl)guanidine; N-(3-acenaphthylenyl)-N'-(adamant- 1-yl)guanidine; N-(3-acenaphthylenyl)-N'-(adamant-2-yl)guanidine; N-(5-acenaphthylenyl)-N'-(adamant-1-yl)guanidine; N-(5-acenaphthylenyl)-N'-(adamant-2-yl)guanidine; N,N'-bis(4- bromo-3-acenaphthyl)guanidine; N,N'-bis(4-bromo-5-acenaphthyl)guanidine; N,N'-bis(4-hydroxy-3-acenaphthyl)guanidine; N,N'-bis(4-hydroxy-5-acenaphthyl)guanidine; N,N'-bis(4-amino-3-acenaphthyl)guanidine; N,N'-bis(4-amino-5-acenaphthyl)guanidine; N,N'-bis(4-nitro-3-acenaphthyl)guanidine; N,N'-bis(4-nitro-5-acenaphthyl)guanidine; N,N'-bis(1-bromo-3-acenaphthyl)guanidine; N,N'-bis(1-bromo-5-acenaphthyl)guanidine; N,N'-bis(2-bromo-3-acenaphthyl)guanidine; N,N'-bis(2-bromo-5-acenaphthyl)guanidine; N,N'-bis(1-hydroxy-3-acenaphthyl)guanidine; N,N'-bis(1-hydroxy-5-acenaphthyl)guanidine; N,N'-bis(2-hydroxy-3-acenaphthyl)guanidine; N,N'-bis(2-hydroxy-5-acenaphthyl)guanidine; N,N'-bis(1-oxo-3-acenaphthyl)guanidine; N,N'-bis(1-oxo-5-acenaphthyl)guanidine; N,N'-bis(2-oxo-3-acephthyl)guanidine; N,N'-bis(2-oxo-5-acenaphthyl)guanidine; N,N'-bis(3-acenaphthylenyl)guanidine; N,N'-bis(4-azido-5-acenaphthyl)guanidine; N,N'-bis(4-sulfonyl-5-acenaphthyl)guanidine; N,N'-bis(5-acenaphthylenyl)guanidine; N-(5-acenaphthyl)-N'-(2,3,4-trichlorophenyl)guanidine; N-(5-acenaphthyl)-N'-(2,3,4-trichlorophenyl)-N-methylguanidine; N-(5-acenaphthyl)-N'-(2,3,4-trichlorophenyl)-N'-methylguanidine; N-(5-acenaphthyl)-N'-(2,3,4-trichlorophenyl)-N,N'-bis-methylguanidine; N,N'-bis(5-acenaphthyl)-N-methylguanidine; N,N'-bis(5-acenaphthyl)-N,N'-bis-methylguanidine; N-(5-acenaphthyl)-N'-(1-anthracenyl)guanidine; N-(5-acenaphthyl)-N'-(1-anthracenyl)-N-methylguanidine; N-(5-acenaphthyl)-N'-(1-anthracenyl)-N'-methylguanidine; N-(5-acenaphthyl)-N'-(1-anthracenyl)-N,N'-bis-methylguanidine; N-(5-acenaphthyl)-N'-(4-tert-butylphenyl)guanidine; N-(5-acenaphthyl)-N'-(4-tert-butylphenyl)-N-methylguanidine; N-(5-acenaphthyl)-N'-(4-tert-butylphenyl)-N'-methylguanidine; N-(5-acenaphthyl)-N'-(4-tert-butylphenyl)-N,N'-bis-methylguanidine; N-(5-acenaphthyl)-N'-(4-cyclohexylphenyl)guanidine; N-(5-acenaphthyl)-N'-(4-cyclohexylphenyl)-N-methylguanidine; N-(5-acenaphthyl)-N'-(4-cyclohexylphenyl)-N'-methylguanidine; N-(5-acenaphthyl)-N'-(4-cyclohexylphenyl)-N,N'-bis-methylguanidine; N-(5-acenaphthyl)-N'-(4-sec-butylphenyl)guanidine; N-(5-acenaphthyl)-N'-(4-sec-butylphenyl)-N-methylguanidine; N-(5-acenaphthyl)-N'-(4-sec-butylphenyl)-N'-methylguanidine; N-(5-acenaphthyl)-N'-(4-sec-butylphenyl)-N,N'-bis-methylguanidine; N-(5-acenaphthyl)-N'-(4-methoxyphenyl)guanidine; N-(5-acenaphthyl)-N'-(4-methoxyphenyl)-N-methylguanidine; N-(5-acenaphthyl)-N'-(4-methoxyphenyl)-N'-methylguanidine; N-(5-acenaphthyl)-N'-(4-methoxyphenyl)-N,N'-bis-methylguanidine; N-(5-acenaphthyl)-N'-(2,3-dichlorophenyl)guanidine; N-(5-acenaphthyl)-N'-(2,3-dichlorophenyl)-N-methylguanidine; N-(5-acenaphthyl)-N'-(2,3-dichlorophenyl)-N'-methylguanidine; N-(5-acenaphthyl)-N'-(2,3-dichlorophenyl)-N,N'-bis-methylguanidine; N-(5-acenaphthyl)-N'-(4-methoxy-2-naphthyl)guanidine; N-(5-acenaphthyl)-N'-(4-methoxy-2-naphthyl)-N-methylguanidine; N-(5-acenaphthyl)-N'-(4-methoxy-2-naphthyl)-N'-methylguanidine; N-(5-acenaphthyl)-N'-(4-methoxy-2-naphthyl)-N,N'-bis-methylguanidine; N-(5-acenaphthyl)-N'-(3,4-dichlorophenyl)guanidine; N-(5-acenaphthyl)-N'-(3,4-dichlorophenyl)-N-methylguanidine; N-(5-acenaphthyl)-N'-(3,4-dichlorophenyl)-N'-methylguanidine; N-(5-acenaphthyl)-N'-(3,4-dichlorophenyl)-N,N'-bis-methylguanidine; N-(5-acenaphthyl)-N'-(4-chlorophenyl)guanidine; N-(5-acenaphthyl)-N'-(4-chlorophenyl)-N-methylguanidine; N-(5-acenaphthyl)-N'-(4-chlorophenyl)-N'-methylguanidine; N-(5-acenaphthyl)-N'-(4-chlorophenyl)-N,N'-bis-methylguanidine; N-(5-acenaphthyl)-N'-(2-naphthyl)guanidine; N-(5-acenaphthyl)-N'-(2-naphthyl)-N-methylguanidine; N-(5-acenaphthyl)-N'-(2-naphthyl)-N'-methylguanidine; N-(5-acenaphthyl)-N'-(2-naphthyl)-N,N'-bis-methylguanidine; N-(5-acenaphthyl)-N'-(6-quinolinyl)guanidine; N-(5-acenaphthyl)-N'-(6-quinolinyl)-N-methylguanidine; N-(5-acenaphthyl)-N'-(6-quinolinyl)-N'-methylguanidine; N-(5-acenaphthyl)-N'-(6-quinolinyl)-N,N'-bis-methylguanidine; N-(5-acenaphthyl)-N'-(4-nitrophenyl)guanidine; N-(5-acenaphthyl)-N'-(4-nitrophenyl)-N-methylguanidine; N-(5-acenaphthyl)-N'-(4-nitrophenyl)-N'-methylguanidine; N-(5-acenaphthyl)-N'-(4-nitrophenyl)-N,N'-bis-methylguanidine; N-(5-acenaphthyl-N'-(3-bi-phenyl)guanidine; N-(5-acenaphthyl-N'-(3-bi-phenyl)-N-methylguanidine; N-(5-acenaphthyl-N'-(3-bi-phenyl)-N'-methylguanidine; N-(5-acenaphthyl-N'-(3-bi-phenyl)-N,N'-bis-methylguanidine; N-(5-acenaphthyl)-N'-(2,3-dimethylphenyl)guanidine; N-(5-acenaphthyl)-N'-(2,3-dimethylphenyl)-N-methylguanidine; N-(5-acenaphthyl)-N'-(2,3-dimethylphenyl)-N'-methylguanidine; N-(5-acenaphthyl)-N'-(2,3-dimethylphenyl)-N,N'-bis-methylguanidine; N-(5-acenaphthyl)-N'-(2-bi-phenyl)guanidine; N-(5-acenaphthyl)-N'-(2-bi-phenyl)-N-methylguanidine; N-(5-acenaphthyl)-N'-(2-bi-phenyl)-N'-methylguanidine; N-(5-acenaphthyl)-N'-(2-bi-phenyl)-N,N'-bis-methylguanidine; N-(5-acenaphthyl)-N'-(2,5-dibromophenyl)guanidine; N-(5-acenaphthyl)-N'-(2,5-dibromophenyl)-N-methylguanidine; N-(5-acenaphthyl)-N'-(2,5-dibromophenyl)-N'-methylguanidine; N-(5-acenaphthyl)-N'-(2,5-dibromophenyl)-N,N'-bis-methylguanidine; N-(5-acenaphthyl)-N'-(3,4-dimethoxyphenyl)guanidine; N-(5-acenaphthyl)-N'-(3,4-dimethoxyphenyl)-N-methylguanidine; N-(5-acenaphthyl)-N'-(3,4-dimethoxyphenyl)-N'-methylguanidine; N-(5-acenaphthyl)-N'-(3,4-dimethoxyphenyl)-N,N'-bis-methylguanidine; N-(5-acenaphthyl)-N'-(4-methoxy-1-naphthyl)-N-methylguanidine; N-(5-acenaphthyl)-N'-(4-methoxy-1-naphthyl)-N'-methylguanidine; N-(5-acenaphthyl)-N'-(4-methoxy-1-naphthyl)-N,N'-dimethylguanidine; N-(5-acenaphthyl)-N'-(4-chloro-1-naphthyl)guanidine; N-(5-acenaphthyl)-N'-(4-chloro-1-naphthyl)-N-methylguanidine; N-(5-acenaphthyl)-N'-(4-chloro-1-naphthyl)-N'-methylguanidine; N-(5-acenaphthyl)-N'-(4-chloro-1-naphthyl)-N,N'-bis-methylguanidine; N-(5-acenaphthyl)-N'-(3,4,5-trichlorophenyl)guanidine; N-(5-acenaphthyl)-N'-(3,4,5-trichlorophenyl)-N-methylguanidine; N-(5-acenaphthyl)-N'-(3,4,5-trichlorophenyl)-N'-methylguanidine; N-(5-acenaphthyl)-N'-(3,4,5-trichlorophenyl)-N,N'-bis-methylguanidine; N-(5-acenaphthyl)-N'-(4-bi-phenyl)guanidine; N-(5-acenaphthyl)-N'-(4-bi-phenyl)-N-methylguanidine; N-(5-acenaphthyl)-N'-(4-bi-phenyl)-N'-methylguanidine; N-(5-acenaphthyl)-N'-(4-bi-phenyl)-N,N'-bis-methylguanidine; N-(5-acenaphthyl)-N'-(2,3,4,5-tetrachlorophenyl)guanidine; N-(5-acenaphthyl)-N'-(2,3,4,5-tetrachlorophenyl)-N-methylguanidine; N-(5-acenaphthyl)-N'-(2,3,4,5-tetrachlorophenyl)-N'-methylguanidine; N-(5-acenaphthyl)-N'-(2,3,4,5-tetrachlorophenyl)-N,N'-bis-methylguanidine; N-(5-acenaphthyl)-N'-(3-isopropylphenyl)guanidine; N-(5-acenaphthyl)-N'-(3-isopropylphenyl)-N-methylguanidine; N-(5-acenaphthyl)-N'-(3-isopropylphenyl)-N'-methylguanidine; N-(5-acenaphthyl)-N'-(3-isopropylphenyl)-N,N'-bis-methylguanidine; N-(5-acenaphthyl)-N'-(3-tert-butylphenyl)guanidine; N-(5- acenaphthyl)-N'-(3-tert-butylphenyl)-N-methylguanidine; N-(5-acenaphthyl)-N'-(3-tert-butylphenyl)-N'-methylguanidine; N-(5-acenaphthyl)-N'-(3-tert-butylphenyl)-N,N'-bis-methylguanidine; N-(5-acenaphthyl)-N'-(2,3,5,6-tetrachlorophenyl)guanidine; N-(5-acenaphthyl)-N'-(2,3,5,6-tetrachlorophenyl)-N-methylguanidine; N-(5-acenaphthyl)-N'-(2,3,5,6-tetrachlorophenyl)-N'-methylguanidine; N-(5-acenaphthyl)-N'-(2,3,5,6-tetrachlorophenyl)-N,N'-bis-methylguanidine; N-(5-acenaphthyl)-N'-(3-iodophenyl)guanidine; N-(5-acenaphthyl)-N'-(3-iodophenyl)-N-methylguanidine; N-(5-acenaphthyl)-N'-(3-iodophenyl)-N'-methylguanidine; N-(5-acenaphthyl)-N'-(3-iodophenyl)-N,N'-bis-methylguanidine; N-(5-acenaphthyl)-N'-(3-nitrophenyl)guanidine; N-(5-acenaphthyl)-N'-(3-nitrophenyl)-N-methylguanidine; N-(5-acenaphthyl)-N'-(3-nitrophenyl)-N'-methylguanidine; N-(5-acenaphthyl)-N'-(3-nitrophenyl)-N,N'-bis-methylguanidine; N-(5-acenaphthyl)-N'-(5-indolinyl)guanidine; N-(5-acenaphthyl)-N'-(5-indolinyl)-N-methylguanidine; N-(5-acenaphthyl)-N'-(5-indolinyl)-N'-methylguanidine; N-(5-acenaphthyl)-N'-(5-indolinyl)-N,N'-bis-methylguanidine; N-(5-acenaphthyl)-N'-(3-acenaphthyl)guanidine; N-(5-acenaphthyl)-N'-(3-acenaphthyl)-N-methylguanidine; N-(5-acenaphthyl)-N'-(3-acenaphthyl)-N'-methylguanidine; N-(5-acenaphthyl)-N'-(3-acenaphthyl)-N,N'-bis-methylguanidine; N-(5-acenaphthyl)-N'-(2-fluorenyl)guanidine; N-(5-acenaphthyl)-N'-(2-fluorenyl)-N-methylguanidine; N-(5-acenaphthyl)-N'-(2-fluorenyl)-N'-methylguanidine; N-(5-acenaphthyl)-N'-(2-fluorenyl)-N,N'-bis-methylguanidine; N-(5-acenaphthyl)-N'-(4-n-butoxyphenyl)guanidine; N-(5-acenaphthyl)-N'-(4-n-butoxyphenyl)-N-methylguanidine; N-(5-acenaphthyl)-N'-(4-n-butoxyphenyl)-N'-methylguanidine; N-(5-acenaphthyl)-N'-(4-n-butoxyphenyl)-N,N'-bis-methylguanidine; N-(5-acenaphthyl)-N'-(3-(2-methoxy)dibenzofuranyl)guanidine; N-(5-acenaphthyl)-N'-(3-(2-methoxy)dibenzofuranyl)-N-methylguanidine; N-(5-acenaphthyl)-N'-(3-(2-methoxy)dibenzofuranyl)-N'-methylguanidine; N-(5-acenaphthyl)-N'-(3-(2-methoxy)dibenzofuranyl)-N,N'-bis-methylguanidine; N-(5-acenaphthyl)-N'-(9-hydroxy-2-fluorenyl)guanidine; N-(5-acenaphthyl)-N'-(9-hydroxy-2-fluorenyl)-N-methylguanidine; N-(5-acenaphthyl)-N'-(9-hydroxy-2-fluorenyl)-N'-methylguanidine; N-(5-acenaphthyl)-N'-(9-hydroxy-2-fluorenyl)-N,N'-bis-methylguanidine; N-(5-acenaphthyl)-N'-(4-trifluoromethylphenyl)guanidine; N-(5-acenaphthyl)-N'-(4-trifluoromethylphenyl)-N-methylguanidine; N-(5-acenaphthyl)-N'-(4-trifluoromethylphenyl)-N'-methylguanidine; N-(5-acenaphthyl)-N'-(4-trifluoromethylphenyl)-N,N'-bis-methylguanidine; N-(5-acenaphthyl)-N'-(4-methylthiophenyl)guanidine; N-(5-acenaphthyl)-N'-(4-methylthiophenyl)-N-methylguanidine; N-(5-acenaphthyl)-N'-(4-methylthiophenyl)-N'-methylguanidine; N-(5-acenaphthyl)-N'-(4-methylthiophenyl)-N,N'-bis-methylguanidine; N-(5-acenaphthyl)-N'-(3-sec-butylphenyl)guanidine; N-(5-acenaphthyl)-N'-(3-sec-butylphenyl)-N-methylguanidine; N-(5-acenaphthyl)-N'-(3-sec-butylphenyl)-N'-methylguanidine; N-(5-acenaphthyl)-N'-(3-sec-butylphenyl)-N,N'-bis-methylguanidine; N-(3-acenaphthyl)-N'-(2,3,4-trichlorophenyl)guanidine; N-(3-acenaphthyl)-N'-(2,3,4-trichlorophenyl)-N-methylguanidine; N-(3-acenaphthyl)-N'-(2,3,4-trichlorophenyl)-N'-methylguanidine; N-(3-acenaphthyl)-N'-(2,3,4-trichlorophenyl)-N,N'-bis-methylguanidine; N,N'-bis(3-acenaphthyl)-N-methylguanidine; N,N'-bis(3-acenaphthyl)-N,N'-bis-methylguanidine; N-(3-acenaphthyl)-N'-(1-anthracenyl)guanidine; N-(3-acenaphthyl)-N'-(1-anthracenyl)-N-methylguanidine; N-(3-acenaphthyl)-N'-(1-anthracenyl)-N'-methylguanidine; N-(3-acenaphthyl)-N'-(1-anthracenyl)-N,N'-bis-methylguanidine; N-(3-acenaphthyl)-N'-(4tert-butylphenyl)guanidine; N-(3-acenaphthyl)-N'-(4-tert-butylphenyl)-N-methylguanidine; N-(3-acenaphthyl)-N'-(4-tert-butylphenyl)-N'-methylguanidine; N-(3-acenaphthyl)-N'-(4-tert-butylphenyl)-N,N'-bis-methylguanidine; N-(3-acenaphthyl)-N'-(4-cyclohexylphenyl)guanidine; N-(3-acenaphthyl)-N'-(4-cyclohexylphenyl)-N-methylguanidine; N-(3-acenaphthyl)-N'-(4-cyclohexylphenyl)-N'-methylguanidine; N-(3-acenaphthyl)-N'-(4-cyclohexylphenyl)-N,N'-bis-methylguanidine; N-(3-acenaphthyl)-N'-(4-sec-butylphenyl)guanidine; N-(3-acenaphthyl)-N'-(4-sec-butylphenyl)-N-methylguanidine; N-(3-acenaphthyl)-N'-(4-sec-butylphenyl)-N'-methylguanidine; N-(3-acenaphthyl)-N'-(4-sec-butylphenyl)-N,N'-bis-methylguanidine; N-(3-acenaphthyl)-N'-(4-methoxyphenyl)guanidine; N-(3-acenaphthyl)-N'-(4-methoxyphenyl)-N-methylguanidine; N-(3-acenaphthyl)-N'-(4-methoxyphenyl)-N'-methylguanidine; N-(3-acenaphthyl)-N'-(4-methoxyphenyl)-N,N'-bis-methylguanidine; N-(3-acenaphthyl)-N'-(2,3-dichlorophenyl)guanidine; N-(3-acenaphthyl)-N'-(2,3-dichlorophenyl)-N-methylguanidine; N-(3-acenaphthyl)-N'-(2,3-dichlorophenyl)-N'-methylguanidine; N-(3-acenaphthyl)-N'-(2,3-dichlorophenyl)-N,N'-bis-methylguanidine; N-(3-acenaphthyl)-N'-(4-methoxy-2-naphthyl)guanidine; N-(3-acenaphthyl)-N'-(4-methoxy-2-naphthyl)-N-methylguanidine; N-(3-acenaphthyl)-N'-(4-methoxy-2-naphthyl)-N'-methylguanidine; N-(3-acenaphthyl)-N'-(4-methoxy-2-naphthyl)-N,N'-bis-methylguanidine; N-(3-acenaphthyl)-N'-(3,4-dichlorophenyl)guanidine; N-(3-acenaphthyl)-N'-(3,4-dichlorophenyl)-N-methylguanidine; N-(3-acenaphthyl)-N'-(3,4-dichlorophenyl)-N'-methylguanidine; N-(3-acenaphthyl)-N'-(3,4-dichlorophenyl)-N,N'-bis-methylguanidine; N-(3-acenaphthyl)-N'-(4-chlorophenyl)guanidine; N-(3-acenaphthyl)-N'-(4-chlorophenyl)-N-methylguanidine; N-(3-acenaphthyl)-N'-(4-chlorophenyl)-N'-methylguanidine; N-(3-acenaphthyl)-N'-(4-chlorophenyl)-N,N'-bis-methylguanidine; N-(3-acenaphthyl)-N'-(2-naphthyl)guanidine; N-(3-acenaphthyl)-N'-(2-naphthyl)-N-methylguanidine; N-(3-acenaphthyl)-N'-(2-naphthyl)-N'-methylguanidine; N-(3-acenaphthyl)-N'-(2-naphthyl)-N,N'-bis-methylguanidine; N-(3-acenaphthyl)-N'-(6-quinolinyl)guanidine; N-(3-acenaphthyl)-N'-(6-quinolinyl)-N-methylguanidine; N-(3-acenaphthyl)-N'-(6-quinolinyl)-N'-methylguanidine; N-(3-acenaphthyl)-N'-(6-quinolinyl)-N,N'-bis-methylguanidine; N-(3-acenaphthyl)-N'-(4-nitrophenyl)guanidine; N-(3-acenaphthyl)-N'-(4-nitrophenyl)-N-methylguanidine; N-(3-acenaphthyl)-N'-(4-nitrophenyl)-N'-methylguanidine; N-(3-acenaphthyl)-N'-(4-nitrophenyl)-N,N'-bis-methylguanidine; N-(3-acenaphthyl-N'-(3-bi-phenyl)guanidine; N-(3-acenaphthyl-N'-(3-bi-phenyl)-N-methylguanidine; N-(3-acenaphthyl-N'-(3-bi-phenyl)-N'-methylguanidine; N-(3-acenaphthyl-N'-(3-bi-phenyl)-N,N'-bis-methylguanidine; N-(3-acenaphthyl)-N'-(2,3-dimethylphenyl)guanidine; N-(3-acenaphthyl)-N'-(2,3-dimethylphenyl)-N-methylguanidine; N-(3-acenaphthyl)-N'-(2,3-dimethylphenyl)-N'-methylguanidine; N-(3-acenaphthyl)-N'-(2,3-dimethylphenyl)-N,N'-bis-methylguanidine; N-(3-acenaphthyl)-N'-(2-bi-phenyl)guanidine; N-(3-acenaphthyl)-N'-(2-bi-phenyl)-N-methylguanidine; N-(3-acenaphthyl)-N'-(2-bi-phenyl)-N'- methylguanidine; N-(3-acenaphthyl)-N'-(2-bi-phenyl)-N,N'-bis-methylguanidine; N-(3-acenaphthyl)-N'-(2,5-dibromophenyl)guanidine; N-(3-acenaphthyl)-N'-(2,5-dibromophenyl)-N-methylguanidine; N-(3-acenaphthyl)-N'-(2,5-dibromophenyl)-N'-methylguanidine; N-(3-acenaphthyl)-N'-(2,5-dibromophenyl)-N,N'-bis-methylguanidine; N-(3-acenaphthyl)-N'-(3,4-dimethoxyphenyl)guanidine; N-(3-acenaphthyl)-N'-(3,4-dimethoxyphenyl)-N-methylguanidine; N-(3-acenaphthyl)-N'-(3,4-dimethoxyphenyl)-N'-methylguanidine; N-(3-acenaphthyl)-N'-(3,4-dimethoxyphenyl)-N,N'-bis-methylguanidine; N-(3-acenaphthyl)-N'-(4-methoxy-1-naphthyl)-N-methylguanidine; N-(3-acenaphthyl)-N'-(4-methoxy-1-naphthyl)-N'-methylguanidine; N-(3-acenaphthyl)-N'-(4-methoxy-1-naphthyl)-N,N'-dimethylguanidine; N-(3-acenaphthyl)-N'-(4-chloro-1-naphthyl)guanidine; N-(3-acenaphthyl)-N'-(4-chloro-1-naphthyl)-N-methylguanidine; N-(3-acenaphthyl)-N'-(4-chloro-1-naphthyl)-N'-methylguanidine; N-(3-acenaphthyl)-N'-(4-chloro-1-naphthyl)-N,N'-bis-methylguanidine; N-(3-acenaphthyl)-N'-(3,4,5-trichlorophenyl)guanidine; N-(3-acenaphthyl)-N'-(3,4,5-trichlorophenyl)-N-methylguanidine; N-(3-acenaphthyl)-N'-(3,4,5-trichlorophenyl)-N'-methylguanidine; N-(3-acenaphthyl)-N'-(3,4,5-trichlorophenyl)-N,N'-bis-methylguanidine; N-(3-acenaphthyl)-N'-(4-bi-phenyl)guanidine; N-(3-acenaphthyl)-N'-(4-bi-phenyl)-N-methylguanidine; N-(3-acenaphthyl)-N'-(4-bi-phenyl)-N'-methylguanidine; N-(3-acenaphthyl)-N'-(4-bi-phenyl)-N,N'-bis-methylguanidine; N-(3-acenaphthyl)-N'-(2,3,4,5-tetrachlorophenyl)guanidine; N-(3-acenaphthyl)-N'-(2,3,4,5-tetrachlorophenyl)-N-methylguanidine; N-(3-acenaphthyl)-N'-(2,3,4,5-tetrachlorophenyl)-N'-methylguanidine; N-(3-acenaphthyl)-N'-(2,3,4,5-tetrachlorophenyl)-N,N'-bis-methylguanidine; N-(3-acenaphthyl)-N'-(3-isopropylphenyl)guanidine; N-(3-acenaphthyl)-N'-(3-isopropylphenyl)-N-methylguanidine; N-(3-acenaphthyl)-N'-(3-isopropylphenyl)-N'-methylguanidine; N-(3-acenaphthyl)-N'-(3-isopropylphenyl)-N,N'-bis-methylguanidine; N-(3-acenaphthyl)-N'-(3-tert-butylphenyl)guanidine; N-(3-acenaphthyl)-N'-(3-tert-butylphenyl)-N-methylguanidine; N-(3-acenaphthyl)-N'-(3-tert-butylphenyl)-N'-methylguanidine; N-(3-acenaphthyl)-N'-(3-tert-butylphenyl)-N,N'-bis-methylguanidine; N-(3-acenaphthyl)-N'-(2,3,5,6-tetrachlorophenyl)guanidine; N-(3-acenaphthyl)-N'-(2,3,5,6-tetrachlorophenyl)-N-methylguanidine; N-(3-acenaphthyl)-N'-(2,3,5,6-tetrachlorophenyl)-N'-methylguanidine; N-(3-acenaphthyl)-N'-(2,3,5,6-tetrachlorophenyl)-N,N'-bis-methylguanidine; N-(3-acenaphthyl)-N'-(3-iodophenyl)guanidine; N-(3-acenaphthyl)-N'-(3-iodophenyl)-N-methylguanidine; N-(3-acenaphthyl)-N'-(3-iodophenyl)-N'-methylguanidine; N-(3-acenaphthyl)-N'-( 3-iodophenyl)-N,N'-bis-methylguanidine; N-(3-acenaphthyl)-N'-(3-nitrophenyl)guanidine; N-(3-acenaphthyl)-N'-(3-nitrophenyl)-N-methylguanidine; N-(3-acenaphthyl)-N'-(3-nitrophenyl)-N'-methylguanidine; N-(3-acenaphthyl)-N'-(3-nitrophenyl)-N,N'-bis-methylguanidine; N-(3-acenaphthyl)-N'-(5-indolinyl)guanidine; N-(3-acenaphthyl)-N'-(5-indolinyl)-N-methylguanidine; N-(3-acenaphthyl)-N'-(5-indolinyl)-N'-methylguanidine; N-(3-acenaphthyl)-N'-(5-indolinyl)-N,N'-bis-methylguanidine; N-(3-acenaphthyl)-N'-(2-fluorenyl)guanidine; N-(3-acenaphthyl)-N'-(2-fluorenyl)-N-methylguanidine; N-(3-acenaphthyl)-N'-(2-fluorenyl)-N'-methylguanidine; N-(3-acenaphthyl)-N'-(2-fluorenyl)-N,N'-bis-methylguanidine; N-(3-acenaphthyl)-N'-(4-n-butoxyphenyl)guanidine; N-(3-acenaphthyl)-N'-(4-n-butoxyphenyl)-N-methylguanidine; N-(3-acenaphthyl)-N'-(4-n-butoxyphenyl)-N'-methylguanidine; N-(3-acenaphthyl)-N'-(4-n-butoxyphenyl)-N,N'-bis-methylguanidine; N-(3-acenaphthyl)-N'-(3-(2-methoxy)dibenzofuranyl)guanidine; N-(3-acenaphthyl)-N'-(3-(2-methoxy)dibenzofuranyl)-N-methylguanidine; N-(3-acenaphthyl)-N'-(3-(2-methoxy)dibenzofuranyl)-N'-methylguanidine; N-(3-acenaphthyl)-N'-(3-(2-methoxy)dibenzofuranyl)-N,N'-bis-methylguanidine; N-(3-acenaphthyl)-N'-(9-hydroxy-2-fluorenyl)guanidine; N-(3-acenaphthyl)-N'-(9-hydroxy-2-fluorenyl)-N-methylguanidine; N-(3-acenaphthyl)-N'-(9-hydroxy-2-fluorenyl)-N'-methylguanidine; N-(3-acenaphthyl)-N'-(9-hydroxy-2-fluorenyl)-N,N'-bis-methylguanidine; N-(3-acenaphthyl)-N'-(4-trifluoromethylphenyl)guanidine; N-(3-acenaphthyl)-N'-(4-trifluoromethylphenyl)-N-methylguanidine; N-(3-acenaphthyl)-N'-(4-trifluoromethylphenyl)-N'-methylguanidine; N-(3-acenaphthyl)-N'-(4-trifluoromethylphenyl)-N,N'-bis-methylguanidine; N-(3-acenaphthyl)-N'-(4-methylthiophenyl)guanidine; N-(3-acenaphthyl)-N'-(4-methylthiophenyl)-N-methylguanidine; N-(3-acenaphthyl)-N'-(4-methylthiophenyl)-N'-methylguanidine; N-(3-acenaphthyl)-N'-(4-methylthiophenyl)-N,N'-bis-methylguanidine; N-(3-acenaphthyl)-N'-(3-sec-butylphenyl)guanidine; N-(3-acenaphthyl)-N'-(3-sec-butylphenyl)-N-methylguanidine; N-(3-acenaphthyl)-N'-(3-sec-butylphenyl)-N'-methylguanidine; N-(3-acenaphthyl); N'-(3-sec-butylphenyl)-N,N'-bis-methylguanidine; N-(5-acenaphthyl)-N'-(4-benzyloxyphenyl)guanidine; N-(5-acenaphthyl)-N'-(3-benzyloxyphenyl)guanidine; N-(5-acenaphthyl)-N'-( 3-sec-butylphenyl)guanidine; N-(5-acenaphthyl)-N'-(2-anthracenyl)guanidine; N-(5-acenaphthyl)-N'-(3-phenethylphenyl)guanidine; N-(5-acenaphthyl)-N'-(4-adamantylphenyl)guanidine; N-(5-acenaphthyl)-N'-(3-benzyloxyphenyl)-N'-methylguanidine; N-(5-acenaphthyl)-N'-(4-benzyloxyphenyl)-N'-methylguanidine; N-(5-acenaphthyl)-N'-(3-biphenyl)-N'-methylguanidine; N-(5-acenaphthyl)-N'-(3-(1'-methyl-2'-phenylethyl)phenyl)guanidine; N-(5-acenaphthyl)-N'-(3,4-tetralinylphenyl)guanidine; N-(5-acenaphthyl)-N'-(7-benzyltetralinylphenyl)guanidine; N-(5-acenaphthyl)-N'-(3,4-dibenzyloxyphenyl)guanidine; N-(5-acenaphthyl)-N'-(3-1-(4-ethoxy)phenyl)propanyl)phenyl)guanidine; N-(5-acenaphthyl)-N'-(3-(N",N"-dibenzyl)aminophenyl)guanidine; N-(5-acenaphthyl)-N'-(3-(1'-benzylbutyl)phenyl)guanidine; N-(5-acenaphthyl)-N'-3-(4-tert-butylbenzoxymethyl)phenylguanidine; N-(5-acenaphthyl)-N'-(2-(2-indolyl)phenyl)guanidine; N-(5-acenaphthyl-N'-(3-bromophenyl)guanidine; N-(5-acenaphthyl)-N'-(2,3,4-trichlorophenyl)-N,N'-dimethylguanidine; N-(5-acenaphthyl)-N'-(2,3,4-trichloro-phenyl)-N'-methylguanidine; N-(5-acenaphthyl)-N'-(4-(2'-benzothiazole-6'-methyl)phenyl)guanidine; N-(3-acenaphthyl)-N'-(4-benzoyloxyphenyl)guanidine; N-(3-acenaphthyl)-N'-(3-benzoyloxyphenyl)guanidine; N-(3-acenaphthyl)-N'-(3-sec-butylphenyl)guanidine; N-(3-acenaphthyl)-N'-(2-anthracenyl)guanidine; N-(3-acenaphthyl)-N'-(3-phenethylphenyl)guanidine; N-(3-acenaphthyl)-N'-(4-adamantylphenyl)guanidine; N-(3-acenaphthyl)-N'-(3-benzyloxyphenyl)-N'-methylguanidine; N-(3-acenaphthyl)-N'-(4-benzyloxyphenyl)-N'-methylguanidine; N-(3-acenaphthyl)-N'-(3-biphenyl)-N'-methylguanidine; N-(3-acenaphthyl)-N'-(3-(1'-methyl-2'-phenylethyl)phenyl)guanidine; N-(3-acenaphthyl)-N'-(3,4-tetralinylphenyl)guanidine; N-(3-acenaphthyl)-N'-(7- benzyltetranylphenyl)guanidine; N-(3-acenaphthyl)-N'-(3-1-(4-ethoxy)phenyl)propanyl)phenyl)guanidine; N-(3-acenaphthyl)-N'-(3-(N",N"-dibenzyl)aminophenyl) guanidine; N-(3-acenaphthyl)-N'-(3-(1'-benzylbutyl)phenyl) guanidine; N-(3-acenaphthyl)-N'-3-(4-tert-butylbenzoxymethyl)phenylguanidine; N-(3-acenaphthyl)-N'-(2-(2-indolyl)phenyl)guanidine; N-(3-acenaphthyl-N'-(3-bromophenyl)guanidine; N-(3-acenaphthyl)-N'-(3,4-dibenzyloxyphenyl)guanidine; N-(3-acenaphthyl)-N'-(2,3,4-trichlorophenyl)-N,N'-dimethylguanidine; N-(3-acenaphthyl)-N'-(2,3,4-trichlorophenyl)-N'-methylguanidine; N-(3-acenaphthyl)-N'-(4-(2'-benzothiazole-6'-methylphenyl)guanidine; and pharmaceutically acceptable salts of said compounds.

Another preferred group of compounds for use in the methods of the invention are diadamantylguanidine compounds of the following Formula VI:

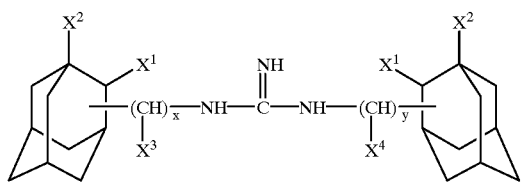

wherein $X^1$, $X^2$, $X^3$, and $X^4$ are the same or different and are selected from the group consisting of hydrogen, hydroxy, acetate, oxo, amino, lower $C_{1-6}$ alkyl, lower $C_{1-6}$ alkyl amino, alkoxy of 1–6 carbon atoms, lower $C_{1-6}$ alkyl amino, alkoxy of 1–6 carbon atoms, di-lower $C_{2-12}$ alkyl amino, nitro, azido, sulfhydryl, cyano, isocynato, halogen, amido, sulfonato or carbamido; wherein at least one of $X^1$, $X^2$, $X^3$, and $X^4$ is other than hydrogen; x and y are the same or different and are 0, 1, 2, 3 or 4.

Specifically preferred diadamantyl guanidines for use in the present methods include di-(3-nitroadamantan-1-yl) guanidine; N,N'-di-(3-hydroxyadamantan-1-yl)guanidine, N,N'-di-(3-amino-adamantan-1-yl)guanidine; N,N'-di-(3-nitro-adamantan-2-yl)guanidine; N,N'-di-(3-hydroxyadamantan-2-yl)guanidine; N,N'-di-(3-aminoadamantan-2-yl)guanidine; N,N'-di-(5-nitroadamantan-2-yl)guanidine; N,N'-di-(5-hydroxy-adamantan-2-yl)guanidine; N,N'-di-(5-aminoadamantan-2-yl)guanidine; N,N'-di-(methylene-adamantan-1-yl) guanidine; N,N'-di-(methylene-adamantan-2-yl)guanidine; N-(adamantan-1-yl)-N'-(methyleneadamantan-1-yl) guanidine; N-(adamantan-2-yl)-N'-(methyleneadamantan-2-yl)guanidine; N-(adamantan-1-yl)-N'-(methyleneadamantan-2-yl)guanidine; N-(adamantan-2-yl)-N'-(methyleneadamantan-1-yl)guanidine; N,N'-di-(methylene-(3-aminoadamantan-1-yl))guanidine; N,N'-di-(methylene-(3-aminoadamantan-2-yl))guanidine; N,N'-di-(methylene-(3-hydroxyadamantan-1-yl))guanidine; N,N'-di-(methylene-(3-hydroxyadamantan-2-yl))guanidine; N,N'-di-(methylene-(3-mercaptoadamantan-1-yl)) guanidine; N,N'-di-(methylene-(3-mercapto-adamantan-2-yl))guanidine; N,N'-di-(methylene-(3-mercaptoadamantan-1-yl))guanidine; N,N'-di-(methylene-(3-mercaptoadamantan-2-yl))guanidine; N,N'-di-(methylene-(3-cyanoadamantan-1-yl))guanidine; N,N'-di-(methylene-(3-cyanoadamantan-2-yl))guanidine; N,N'-di-(methylene-(3-cyanoadamantan-1-yl))guanidine; and N,N'-di-(methylene-(3-cyanoadamantan-2-yl))guanidine; and pharmaceutically acceptable salts thereof.

A further preferred group of compounds for use in the present methods are hydrazinedicarboximidamide compounds of the following Formula VII:

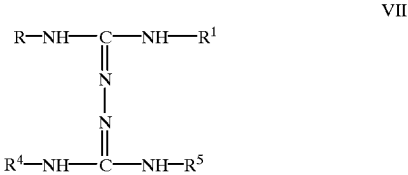

or a tautomer thereof, wherein R, $R^1$, $R^4$ and $R^5$ are the same or different and are cycloalkyl of 3 to 12 carbon atoms, e.g., cyclopropyl, cyclopentyl, cyclohexyl, cyclohexenyl, cycloheptyl, 1,4-methylenecyclohexyl, 1- or 2-adamantyl, exo or endo 2-norbornyl, exo or endo 2-isobornyl, menthyl, cyclopentyl-methyl, cyclohexylmethyl, 1- or 2-cyclohexylethyl and 1-, 2- or 3-cyclohexylpropyl; carbocyclic aryl, alkaryl, aralkyl or heterocyclic, e.g., of 6 to 18 carbon atoms and containing 1–3 separate or fused rings, and 0–5 O, N and/or S ring atoms in an aryl, alicyclic or mixed ring system, e.g., phenyl, benzyl, 1- and 2-phenylethyl, 1-, 2-, or 3-phenylpropyl; o-, m-, or p-tolyl, m,m'-dimethylphenyl, o-, m-, or p-ethylphenyl, m,m'-diethylphenyl, m-methyl-m'-ethylphenyl and o-propylphenyl, 1-naphthyl, 2-naphthyl, biphenyl; indanyl, for example, 4-indanyl; indenyl, for example, 1- or 4-indenyl; 3-acenaphthyl, 5-acenaphthyl; 3-acenaphthylene, 5-acenaphthylene; indolyl, for example, 7-indolyl; benzthiazole, quinolinyl, isoquinolinyl, pyridyl, pyrimidinyl, pyrazinyl, furanyl, thienyl, pyrrolyl, thiazolyl, oxazolyl, coumarinyl; or imidazolyl;

wherein R, $R^1$, $R^4$ or $R^5$ is optionally substituted hydroxy, acetate, oxo, amino, lower $C_{1-6}$ alkyl, lower $C_{1-6}$ alkyl amino, alkoxy of 1–6 carbon atoms, di-lower $C_{2-12}$ alkyl amino, nitro, azido, sulfhydryl, cyano, isocyanato, halogen, amido, sulfonato or carbamido.

Specifically preferred compounds of Formula VII for use in the present methods include N,N',N",N"'-tetracyclohexylhydrazinedicarboximidamide; N,N',N",N"'-tetraphenylhydrazinedicarboximidamide; N,N'-di-(adamantan-1-yl)-N",N"'-dicyclohexylhydrazinedicarboximidamide; N,N',N",N"'-tetra-(adamantan-1-yl)hydrazinedicarboximidamide; N,N',N",N"'-tetra-(adamantan-2-yl)-hydrazinedicarboximidamide; N,N'-di-(adamantan-1-yl)-N",N"'-di-(adamantan-2-yl)-hydrazinedicarboximidamide; N,N'-di-(2-norbornyl)-N",N"'-dicyclohexylhydrazinedicarboximide; N,N'-di-(2-isobornyl)-N",N"'-dicyclohexylhydrazinedicarboximidamide; N,N'-di-(2-isobornyl)-N",N"'-di-(adamantan-1-yl) hydrazinedicarboximidamide; N,N'-di-(2-isobornyl)-N", N"'-di-(adamantan-2-yl)hydrazinedicarboximidamide; N,N',N",N"'-tetra-(acenaphth-5-yl) hydrazinedicarboximidamide; N,N',N",N"'-tetra-(acenaphthylen-5-yl)-hydrazinedicarboximidamide; N,N'-di-(acenaphth-5-yl)-N",N"'-di-(acenaphthylen-5-yl)-hydrazinedicarboximidamide; N,N'-di-(2-norbornyl)-N", N"'-di-(acenaphth-5-yl)hydrazinedicarboximidamide; N,N'-di-(2-norbornyl)-N",N"'-di-(acenaphthylen-5-yl) hydrazinedicarboximidamide; N,N'-di-(2-isobornyl)-N", N"'-di-(acenaphth-5-yl)hydrazinedicarboximidamide; N,N'-di-(2-isobornyl)-N",N"'-di-(acenaphthylen-5-yl) hydrazinedicarboximidamide; N,N'-dicyclohexyl-N",N"'-di-(acenaphth-5-yl)hydrazinedicarboximidamide; and N,N'-dicyclohexyl-N",N"'-di-(acenaphthylen-5-yl) hydrazinedicarboximidamide.

Also preferred for use in the present methods are hydrazinecarboximidamides of the following Formula VIII:

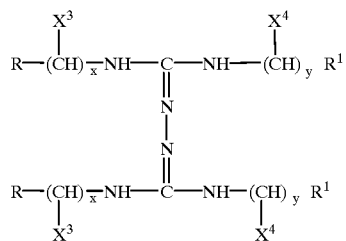

VIII or a tautomer thereof;

wherein R and $R^1$ are the same or different and are cycloalkyl of 3 to 12 carbon atoms, e.g., cyclopropyl, cyclopentyl, cyclohexyl, cyclohexenyl, cycloheptyl, 1,4-methylenecyclohexyl, 1- or 2-adamantyl, exo or endo 2-norbornyl, exo or endo 2-isobornyl, menthyl, cyclopentylmethyl, cyclohexylmethyl, 1- or 2-cyclohexylethyl and 1-, 2- or 3-cyclohexylpropyl; carbocyclic aryl, alkaryl, aralkyl or heterocyclic, e.g., of 6 to 18 carbon atoms and containing 1–3 separate or fused rings, and 0–5 O, N and/or S ring atoms in an aryl, alicyclic or mixed ring system, e.g., phenyl, benzyl, 1- and 2-phenylethyl, 1-, 2-, or 3-phenylpropyl; o-, m-, or p-tolyl, m,m'-dimethylphenyl, o-, m-, or p-ethylphenyl, m,m'-diethylphenyl, m-methyl-m'-ethylphenyl and o-propylphenyl, 1-naphthyl, 2-naphthyl, biphenyl; indanyl, for example, 4-indanyl; 3-acenaphthyl, 5-acenaphthyl; 3-acenaphthylene, 5-acenaphthylene; indenyl, for example, 1- or 4-indenyl; indolyl, for example, 7-indolyl; benzthiazole, quinolinyl, isoquinolinyl, pyridyl, pyrimidinyl, pyrazinyl, furanyl, thienyl, pyrrolyl, thiazolyl, oxazolyl, coumarinyl, or imidazolyl;

$X^3$ and $X^4$ are the same or different and are selected from the group consisting of hydrogen, hydroxy, acetate, oxo, amino, lower $C_{1-6}$ alkyl, lower $C_{1-6}$ alkyl amino, alkoxy of 1–6 carbon atoms, di-lower $C_{2-12}$ allyl amino, nitro, azido, sulfhydryl, cyano, isocyanato, halogen, amido, sulfonato or carbamido;

wherein R and $R^1$ are optionally substituted by hydroxy, acetate, oxo, amino, lower $C_{1-6}$ alkyl, lower $C_{1-6}$ alkyl amino, alkoxy of 1–6 carbon atoms, di-lower $C_{2-12}$ alkyl amino, nitro, azido, sulfhydryl, cyano, isocyanato, halogen, amido, sulfonato or carbamido; x and y are the same or different and are 0, 1, 2, 3 or 4.

Also preferred for use in the present methods are aminoguanidines, including compounds of the following Formula IX:

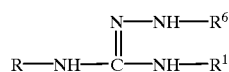

IX or a tautomer thereof, wherein R and $R^1$ are the same or different and are cycloalkyl of 3 to 12 carbon atoms, e.g., cyclopropyl, cyclopentyl, cyclohexyl, cyclohexenyl, cycloheptyl, 1,4-methylenecyclohexyl, 1- or 2-adamantyl, exo or endo 2-norbornyl, exo or endo 2-isobornyl menthyl, cyclopentylmethyl, cyclohexylmethyl, 1- or 2-cyclohexylethyl and 1-, 2- or 3-cyclohexylpropyl; carbocyclic aryl, alkaryl, aralkyl or heterocyclic, e.g., of 6 to 18 carbon atoms and containing 1–3 separate or fused rings, and 0–5 O, N and/or S ring atoms in an aryl, alicyclic or mixed ring system, e.g., phenyl, benzyl, 1- and 2-phenylethyl, 1-, 2-, or 3-phenylpropyl; o-, m-, or p-tolyl, m,m'-dimethylphenyl, o-, m-, or p-ethylphenyl, m,m'-diethylphenyl, m-methyl-m'-ethylphenyl and o-propylphenyl, 1-naphthyl, 2-naphthyl, biphenyl; indanyl, for example, 4-indanyl; indenyl, for example, 1- or 4-indenyl; 3-acenaphthyl, 5-acenaphthyl; 3-acenaphthylene, 5-acenaphthylene; indolyl, for example, 7-indolyl; benzthiazole, quinolinyl, isoquinolinyl, pyridyl, pyrimidinyl, pyrazinyl, furanyl, thienyl, pyrrolyl, thiazolyl, oxazolyl, coumarinyl, or imidazolyl;

wherein R and $R^1$ are optionally substituted by hydroxy, acetate, oxo, amino, lower $C_{1-6}$ alkyl, lower $C_{1-6}$ alkyl amino, alkoxy of 1–6 carbon atoms, di-lower $C_{2-12}$ alkyl amino, nitro, azido, sulfhydryl, cyano, isocyanato, halogen, amido, sulfonato or carbamido;

$R^6$ is hydrogen, $C_1-C_6$ alkyl, $C_3-C_{12}$ cycloalkyl, carbocyclic aryl, nitrile, $C_1-C_6$ alkoxycarbonyl, $C_1-C_6$ acyl or benzoyl.

Further preferred aminoguanidines for use in the present methods are compounds of the following Formula X:

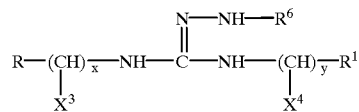

X or a tautomer thereof, wherein R and $R^1$ are the same or different and are cycloalkyl of 3 to 12 carbon atoms, e.g., cyclopropyl, cyclopentyl, cyclohexyl, cyclohexenyl, cycloheptyl, 1,4-methylenecyclohexyl, 1- or 2-adamantyl, exo or endo 2-norbornyl, exo or endo 2-isobornyl, menthyl, cyclopentylmethyl, cyclohexylmethyl, 1- or 2-cyclohexylethyl and 1-, 2- or 3-cyclohexylpropyl; carbocyclic aryl, alkaryl, aralkyl or heterocyclic, e.g., of 6 to 18 carbon atoms and containing 1–3 separate or fused rings, and 0–5 O, N and/or S ring atoms in an aryl, alicyclic or mixed ring system, e.g., phenyl, benzyl, 1- and 2-phenylethyl, 1-, 2-, or 3-phenylpropyl; o-, m-, or p-tolyl, m,m'-dimethylphenyl, o-, m-, or p-ethylphenyl, m,m'-diethylphenyl, m-methyl-m'-ethylphenyl and o-propylphenyl, 1-naphthyl, 2-naphthyl, biphenyl; indanyl, for example, 4-indanyl; indenyl, for example, 1- or 4-indenyl; 3-acenaphthyl, 5-acenaphthyl; 3-acenaphthylene, 5-acenaphthylene; indolyl, for example, 7-indolyl; benzthiazole, quinolinyl, isoquinolinyl, pyridyl, pyrimidinyl, pyrazinyl, furanyl, thienyl, pyrrolyl, thiazolyl, oxazolyl, coumarinyl, or imidazolyl;

$X^3$ and $X^4$ are the same or different and selected from the group consisting of hydrogen, hydroxy, acetate, oxo, amino, lower $C_{1-6}$ alkyl, lower $C_{1-6}$ alkyl amino, alkoxy of 1–6 carbon atoms, di-lower $C_{2-12}$ alkyl amino, nitro, azido, sulfhydryl, cyano, isocyanato, halogen, amido, sulfonato or carbamido;

wherein R and $R^1$ are optionally substituted by hydroxy, acetate, oxo, amino, lower $C_{1-6}$ alkyl, lower $C_{1-6}$ alkyl amino, alkoxy of 1–6 carbon atoms, di-lower $C_{2-12}$ alkyl amino, nitro, azido, sulfhydryl, cyano, isocyanato, halogen, amido, sulfonato or carbamido;

x and y are the same or different and are 0, 1, 2, 3 or 4;

$R^6$ is hydrogen, $C_1-C_6$ alkyl, $C_3-C_{12}$ cycloalkyl, carbocyclic aryl, nitrile, $C_1-C_6$ alkoxycarbonyl, $C_1-C_6$ acyl or benzoyl. Specifically preferred compounds of Formula X include N,N'-dicyclohexyl-N"-aminoguanidine, N,N'-di-(adamantan-1-yl)-N"-aminoguanidine, N,N'-di-(adamantan-2-yl)-N"-aminoguanidine, N,N'-di-(2-norbornyl)-N"-aminoguanidine, and N,N'-di-(2-isobornyl)-N"-aminoguanidine.

Also preferred for use in the present methods are compounds of the following Formula XI:

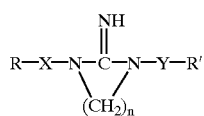

wherein n is 2, 3, 4 or 5;

X and Y are independently a single bond, a branched or straight chain $C_1$–$C_{12}$ alkylene or a branched or straight chain alkenylene;

R and R' are independently hydrogen, substituted or unsubstituted a cycloalkyl group of at least 3 carbons, a substituted or unsubstituted carbocyclic group of at least 6 carbon atoms, particularly substituted or unsubstituted phenyl; substituted or unsubstituted aralkyl of at least 6 carbon atoms and containing 1–3 separate or fused rings, or a substituted or unsubstituted heterocyclic or heteroaromatic group having from 1 to 3 rings, 3 to 8 ring members in each ring and 1 to 3 heteroatoms, and wherein each of R and R' may be substituted; or wherein R and R' together with the guanidine nitrogen to which they are attached form a saturated or unsaturated cyclic ring containing at least 2 carbon atoms exclusive of the guanidine carbon atom, and wherein said cyclic ring may be substituted with one or more alkyl groups of 1–6 carbon atoms, carbocyclic aryl or at least 6 carbon atoms, cycloalkyl groups of 3–12 carbon atoms, or 1–2 fused aromatic rings; and pharmaceutically acceptable salts thereof. Specifically preferred compounds of Formula XI include N,N'-di(m-ethylphenyl)-2-iminodazolidine; N,N'-bis-(4-tert-butylphenyl)-2-iminopyrimidazolidine; N,N'-bis-(4-pentylphenyl)-2-iminopyrimidazolidine; N,N'-bis-(4-hexylphenyl)-2-iminopyrimidazolidine; N,N'-bis-(naphthyl)-2-iminopyrimidazolidine; N,N'-bis-(5-acenaphthyl)-2-iminopyrimidazolidine; N,N'-bis-(tetralinyl)-2-iminopyrimidazolidine.

A further group of compounds preferred for use in methods of the invention are compounds of the following Formula XII:

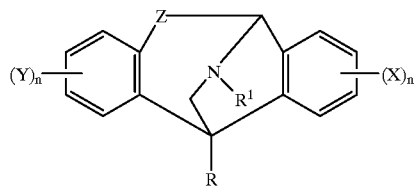

wherein:

R is hydrogen, $C_2$–$C_6$ acyl, $C_1$–$C_6$ alkyl, aryl, $C_1$–$C_6$ alkoxycarbonyl, $C_7$–$C_{10}$ aralkyl, $C_2$–$C_6$ alkenyl, $C_3$–$C_{15}$ dialkylaminoalkyl, $C_1$–$C_6$ hydroxyalkyl, $C_2$–$C_6$ alkynyl, $C_3$–$C_{15}$ trialkylsilyl, $C_4$–$C_{10}$ alkylcycloalkyl, or $C_3$–$C_6$ cycloalkyl;

$R^1$ hydrogen, $C_1$–$C_6$ alkyl, $C_2$–$C_6$ alkenyl, $C_7$–$C_{10}$ aralkyl, $C_1$–$C_6$ alkoxy, $C_1$–$C_6$ alkylamino, or $C_3$–$C_{15}$ dialkylaminoalkyl;

X and Y are independently selected from the group consisting of a halogen such as chloro, fluoro, bromo, iodo, $C_1$–$C_6$ alkoxy, $C_2$–$C_6$ dialkoxymethyl, $C_1$–$C_6$ alkyl, cyano, $C_3$–$C_{15}$ dialkylaminoalkyl, carboxy, carboxamido, $C_1$–$C_6$ haloalkyl, e.g. trifluoromethyl; $C_1$–$C_6$ haloalkylthio, allyl, aralkyl, $C_3$–$C_6$ cycloalkyl, aroyl, aralkoxy, $C_2$–$C_6$ acyl, aryl, substituted aryl, heteroaryl, substituted heteroaryl, $C_3$–$C_6$ heterocycloalkyl, $C_1$–$C_6$ alkylthio, $C_1$–$C_6$ alkylsulfonyl, $C_1$–$C_6$ haloalkylsulfonyl, $C_1$–$C_6$ alkylsulfinyl, $C_1$–$C_6$ haloalkylsulfinyl, arylthio, $C_1$–$C_6$ haloalkoxy, amino, $C_1$–$C_6$ alkylamino, $C_2$–$C_{15}$ dialkylamino, hydroxy, carbamoyl, $C_1$–$C_6$ N-alkylcarbamoyl, $C_2$–$C_{15}$ N,N-dialkylcarbamoyl, nitro and $C_2$–$C_{15}$ dialkylsulfamoyl;

Z represents a group selected from

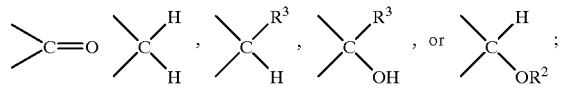

wherein $R^2$ is hydrogen, $C_1$–$C_6$ alkyl, $C_2$–$C_6$ alkenyl, aralkyl, $C_4$–$C_{15}$ dialkylaminoalkyl, heterocycloalkyl, $C_2$–$C_6$ acyl, aroyl, or aralkanoyl, and $R^3$ is $C_1$–$C_6$ alkyl, $C_2$–$C_6$ alkenyl, phenyl, aralkyl or $C_3$–$C_{15}$ dialkylaminoalkyl; and n is an integer selected from 0 (X or Y is hydrogen, respectively), 1, 2, 3 or 4, or a pharmaceutically acceptable salt thereof. The compounds having Formula (XII) above may exist in racemic form or in the optically active stereoisomeric form. With respect to Formula XII, typical $C_1$–$C_6$ alkyl groups include methyl, ethyl, n-propyl, i-propyl, n-butyl t-butyl, i-butyl, pentyl, i-pentyl and hexyl groups; typical $C_2$–$C_6$ acyl groups include acetyl, propanoyl, i-propanoyl, butanoyl, s-butanoyl, pentanoyl and hexanoyl; typical aryl groups include phenyl, naphthyl, phenanthryl and anthracyl; typical $C_1$–$C_6$ alkoxycarbonyl groups include carbonyl substituted by methoxy, ethoxy, propanoxy, i-propanoxy, n-butanoxy, t-butanoxy, i-butanoxy, petanoxy and hexanoxy; typical aralkyl groups include the above-listed $C_1$–$C_6$ alkyl groups substituted by phenyl, naphthyl, phenanthryl and anthracyl groups, e.g. benzyl, phenethyl, phenylpropyl, phenylisopropyl and phenylbutyl; typical $C_2$–$C_6$ alkenyl groups include vinyl, allyl, 2-butenyl, 2-pentenyl and 2-hexenyl groups; typical $C_2$–$C_6$ alkynyl groups include ethynyl and proparyl groups; typical halo include fluoro, chloro, bromo and iodo; typical aroyl include carbonyl substituted by phenyl, naphthyl, phenanthryl and anthracyl; typical aralkanoyl groups include carbonyl substituted by the above-listed aralkyl groups; typical aralkoxy groups include the above-listed $C_1$–$C_6$ alkoxy groups substituted by phenyl, naphthyl, phenanthyl and anthracyl groups; typical substituted aryl groups include the above-listed aryl groups substituted by halo, hydroxy, amino and the like; typical heteroaryl groups include furyl, thienyl, pyrrolyl, thiazolyl, pyridyl, pyrimidinyl, pyrizinyl and oxazolyl; typical substituted heteroaryl groups include the above-listed heteroaryl groups substituted by halo, $C_1$–$C_6$ alkyl and the like; typical $C_5$–$C_6$ heterocycloalkyl groups include tetrahydrofuranyl, tetrahydropyranyl, piperidinyl and pyrrolidinyl; typical $C_3$–$C_{15}$-dialkylaminoalkyl groups include N,N-dimethylaminomethyl, N,N-dimethylaminoethyl, N,N-dimethylaminopropyl and N,N-dimethylaminobutyl.

Specifically preferred compounds of Formula XII for use in the present methods are disclosed in PCT/US92/03554 and include (+) and/or (−) 10,5-(iminomethano)-10,11-dihydro-5H-dibenzo[a,d]cycloheptene; (+) and/or (−) 5-methyl-10,5-(iminomethano)-10,11-dihydro-5H-dibenzo[a,d]cycloheptene; (+) and/or (−) N-methyl-10,5-(iminomethano)-10,11-dihydro-5H-dibenzo[a,d]cycloheptene; (+) and/or (−) 5-methyl-N-methyl-10,5-(iminomethano)-10,11-dihydro-5H-dibenzo[a,d]cycloheptene; (−)-3-chloro-5-(iminomethano)-10,11- dihydro-5H-dibenzo-[a,d]cycloheptene; (+) 3-chloro-5-(iminomethano)-10,11-dihydro-5H-dibenzo-[a,d]cycloheptene; (−)-N-methyl-3-chloro-5-(iminomethano)-10,11-dihydro-5H-dibenzo-[a,d]cycloheptene; (+)-N-methyl-3-chloro-5-(iminomethano)-10,11-dihydro-5H-dibenzo-[a,d]cycloheptene; 3-iodo-5-(iminomethano)-10,11-dihydro-5H-dibenzo-[a,d]cycloheptene; N-methyl-3-iodo-5-(iminomethano)-10,11-dihydro-5H-dibenzo-[a,d]cycloheptene; 7-methoxy-5-(iminomethano)-10,11-dihydro-5H-dibenzo-[a,d]cycloheptene; 3-bromo-5-(iminomethano)-10,11-dihydro-5H-dibenzo-[a,d]cycloheptene; 3-chloro-7-methoxy-5-(iminomethano)-10,11-dihydro-5H-dibenzo-[a,d]cycloheptene; 3-bromo-7-methoxy-5-(iminomethano)-10,11-dihydro-5H-dibenzo-[a,d]cycloheptene; 7-chloro-5-(iminomethano)-10,11-dihydro-5H-dibenzo-[a,d]cycloheptene; 3-amino-5-(iminomethano)-10,11-dihydro-5H-dibenzo-[a,d]cycloheptene; 3-bromo-N-methyl-5-(iminomethano)-10,11-dihydro-5H-dibenzo-[a,d]cycloheptene; 3-bromo-7-methoxy-N-methyl-5-(iminomethano)-10,11-dihydro-5H-dibenzo-[a,d]cycloheptene; (−)-3-fluoro-5-(iminomethano)-10,11-dihydro-5H-dibenzo-[a,d]cycloheptene; (+)-3-fluoro-5-(iminomethano)-10,11-dihydro-5H-dibenzo-[a,d]cycloheptene; (−)-N-methyl-3-fluoro-5-(iminomethano)-10,11-dihydro-5H-dibenzo-[a,d]cycloheptene; (+)-N-methyl-3-fluoro-5-(iminomethano)-10,11-dihydro-5H-dibenzo-[a,d]cycloheptene; 3-methoxy-5-(iminomethano)-10,11-dihydro-5H-dibenzo-[a,d]cycloheptene; 3-nitro-5-(iminomethano)-10,11-dihydro-5H-dibenzo-[a,d]cycloheptene; 3-azido-5-(iminomethano)-10,11-dihydro-5H-dibenzo-[a,d]cycloheptene; 3-trifluoromethyl-5-(iminomethano)-10,11-dihydro-5H-dibenzo-[a,d]cycloheptene; N-methyl-3-trifluoromethyl-5-(iminomethano)-10,11-dihydro-5H-dibenzo-[a,d]cycloheptene; 3,7-difluoro-5-(iminomethano)-10,11-dihydro-5H-dibenzo-[a,d]cycloheptene; 3-phenyl-5-(iminomethano)-10,11-dihydro-5H-dibenzo-[a,d]cycloheptene; 3-amino-5-(iminomethano)-10,11-dihydro-5H-dibenzo-[a,d]cycloheptene; 8-hydroxy-5-(iminomethano)-10,11-dihydro-5H-dibenzo-[a,d]cycloheptene; 3-hydroxy-5-(iminomethano)-10,11-dihydro-5H-dibenzo-[a,d]cycloheptene; 8-methoxy-5-(iminomethano)-10,11-dihydro-5H-dibenzo-[a,d]cycloheptene; 3-cyano-5-(iminomethano)-10,11-dihydro-5H-dibenzo-[a,d]cycloheptene; and 3-methylthio-5-(iminomethano)-10,11-dihydro-5H-dibenzo-[a,d]cycloheptene; and pharmaceutically acceptable salts thereof. Racemic mixtures and optically active isomers of the above compounds are also preferred.

N,N-disubstituted guanidines are also preferred for use in methods of the invention, including compounds of the following Formula XIII:

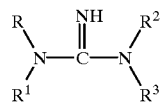

XIII wherein:

R and $R^1$ are each independently substituted or unsubstituted alkyl having from 1 to about 20 carbon atoms, substituted or unsubstituted alkenyl having from 2 to about 20 carbon atoms, substituted or unsubstituted alkynyl having from 2 to about 20 carbon atoms, substituted or unsubstituted alkoxy having from 1 to about 20 carbon atoms, substituted or unsubstituted aminoalkyl having 1 to about 20 carbon atoms, substituted or unsubstituted alkylthio having from 1 to about 20 carbon atoms, substituted or unsubstituted alkylsulfinyl having from 1 to about 20 carbon atoms, substituted or unsubstituted carbocyclic aryl having at least about 5 ring atoms, substituted or unsubstituted aralkyl having at least about 5 ring atoms, or a substituted or unsubstituted heteroaromatic or heteroalicyclic group having from 1 to 3 rings, 3 to 8 ring members in each ring and from 1 to 3 heteroatoms, with at least one of R and $R^1$ being carbocyclic aryl, aralkyl, a heteroaromatic group or a heterocyclic group;

$R^2$ and $R^3$ each being independently selected from the group consisting of hydrogen, substituted and unsubstituted alkyl having from 1 to about 20 carbon atoms, substituted and unsubstituted alkoxy having from 1 to about 20 carbon atoms, substituted and unsubstituted alkylthio having from 1 to about 20 carbon atoms, substituted and unsubstituted alkylsulfinyl having from 1 to about 20 carbon atoms, substituted and unsubstituted alkylsulfonyl having from 1 to about 20 carbon atoms, and substituted and unsubstituted aminoalkyl; and pharmaceutically acceptable salts thereof. A preferred group of compounds of Formula XIII are those wherein at least one and more preferably both of $R^2$ and $R^3$ are hydrogen, i.e. compounds of the formula $R(R^1)NC(=NH)NH_2$ where R and $R^1$ are as defined above for Formula XIII. Also preferred is where at least one, or more preferably both, of R and $R^1$ is substituted or unsubstituted carbocyclic aryl or substituted or unsubstituted aralkyl or substituted or unsubstituted alkaryl. Preferred compounds of Formula XIII also include those compounds having substituents with 1 to about 6 carbon atoms, particularly $R^2$ and/or $R^3$ groups that have 1 to 6 carbon atoms (where $R^2$ and/or $R^3$ are other than hydrogen). Particularly preferred $R^2$ and $R^3$ substituents of compounds of Formula XIII include unsubstituted alkyl and heteroalkyl such as alkoxy, alkylthio, alkylsulfinyl, alkylsulfonyl and aminoalkyl. Preferred R and $R^1$ groups include substituted and unsubstituted acenaphthyl, phenyl, biphenyl, naphthyl, fluorenyl and benzyl, particularly alkyl-substituted and alkoxy-substituted phenyl and benzyl. Particularly preferred R and $R^1$ groups include straight and branched chain $C_{1-8}$-alkyl substituted phenyl and benzyl such as tert-butylphenyl, tert-butylbenzyl, sec-butylphenyl, sec-butylbenzyl, n-butylphenyl, n-butylbenzyl, iso-butylphenyl, iso-butylbenzyl, pentylphenyl, pentylbenzyl, hexylphenyl, hexylbenzyl and the like; straight and branched chain $C_{1-8}$-alkoxy (including haloalkoxy, i.e. alkoxy substituted by F, Cl, Br and/or I) substituted phenyl and benzyl such as butoxyphenyl, butoxybenzyl, pentoxyphenyl, pentoxybenzyl, hexoxyphenyl, hexoxybenzyl, trifluoromethoxyphenyl, trifluorobenzyl, fluoro and the like; alkaryl (including alkoxyaryl) substituted phenyl and benzyl, particularly substituted and unsubstituted benzyl and benzyloxy (especially —$OCH_2C_6H_5$). Cycloalkyl and aryl (particularly carbocyclic aryl) such as substituted phenyl, benzyl and naphthyl are also preferred R and $R^1$ groups such as biphenyl, phenylbenzyl (i.e. —$CH_2C_6H_4C_6H_5$), cyclohexylphenyl, cyclohexylbenzyl and the like. Halo (i.e., F, Cl, Br and/or I) substituted R and $R^1$ groups are also preferred including halo-substituted phenyl, naphthyl and benzyl. Specifically preferred compounds of Formula XIII above include N-(4-sec-butylphenyl)-N-benzylguanidine; N-(5-acenaphthyl)-N-benzylguanidine; N-(3-acenaphthyl)-N-benzylguanidine; N-(5-acenaphthyl)-N-(4-isopropylbenzyl)guanidine; N-(3-acenaphthyl)-N-(4-isopropylbenzyl)guanidine; N-(4-cyclohexylphenyl)-N-(4-isopropylbenzyl)guanidine; N-(4-cyclohexylphenyl)-N-(4-tert-butylbenzyl)guanidine; N-(2-fluorenyl)-N-(4-tertbutylbenzyl)guanidine; N-(4-sec-butylphenyl)-N-(cinnamylmethylene)guanidine; N-(4-n-butoxyphenyl)-N-(4-tert-butylbenzyl)guanidine; N-(3-biphenyl)-N-(4-tert-butylbenzyl)guanidine; N-(5-indanyl)-N-(4-tert-butylbenzyl)guanidine; N-(3-trifluoromethoxyphenyl)-N-(4-tert-butylbenzyl)guanidine; N-(4-sec-butylphenyl)-N-(4-tert-butylbenzyl)guanidine; N-(5-acenaphthyl)-N-(4-tert-butylbenzyl)guanidine; N-(3-acenaphthyl)-N-(4-tert-butylbenzyl)guanidine; N-(methoxy-1-naphthyl)-N-(4-tert-butylbenzyl)guanidine; N-(1-naphthyl)-N-(4-tert-butylbenzyl)guanidine; N-(3-iodophenyl)-N-(4-tert-butylbenzyl)guanidine; N-(4-chloro-1-naphthyl)-N-(4-tert-benzyl)guanidine; N-(4-tert-butylphenyl)-N-(4-tert-butylbenzyl)guanidine; N-(4-iodophenyl)-N-(4-tert-butylbenzyl)guanidine; N-(1-naphthylmethyl)-N-(4-tert-butylbenzyl)guanidine; N-(5-acenaphthyl)-N-(3-phenoxybenzyl)guanidine; N-(3-trifluoromethylphenyl)-N-(4-tert-butylbenzyl)guanidine; N-(3-methylthiophenyl)-N-(4-tert-butylbenzyl)guanidine; N-(5-acenaphthyl)-N-(3-2-iodobenzyl)guanidine; N-(5-acenaphthyl)-N-(cinnamyl) guanidine; N-(5-acenaphthyl)-N-(4-iodobenzyl)guanidine; N-(5-acenaphthyl)-N-(4-trifluoromethoxybenzyl)guanidine; and pharmaceutically acceptable salts thereof. Such compounds are disclosed in International Application PCT/US95/01536, incorporated herein by reference.

A still further group of preferred compounds for use in the present methods are guanidines having a substituent of substituted or unsubstituted fluorenyl, phenanthracenyl, anthracenyl and fluoranthenyl, including compounds of the Formulae I, II or III above and having at least one guanidine substituent of substituted or unsubstituted fluorenyl, substituted or unsubstituted phenanthracenyl, substituted or unsubstituted anthracenyl and substituted or unsubstituted fluoranthenyl. Specifically preferred compounds include N,N'-bis(2-fluorenyl)guanidine; N,N'-bis(2-fluorenyl)-N-methylguanidine; N,N'-bis(2-fluorenyl)-N,N'-dimethylguanidine; N,N'-bis(anthracenyl)guanidine; N,N'-bis(anthracenyl)-N-methylguanidine; N,N'-bis(anthracenyl)-N,N'-dimethylguanidine; N,N'-bis(phenanthracenyl)guanidine; N,N'-bis(phenanthracenyl)-N-methylguanidine; N,N'-bis(phenanthracenyl)-N,N'-dimethylguanidine; N,N'-bis(fluoranthenyl)guanidine; N,N'-bis(fluoroanthenyl)-N-methylguanidine; N,N'-bis(fluoroanthenyl)-N,N'-dimethylguanidine; N-(anthracenyl)-N'-(1-adamantyl)guanidine; N-(anthracenyl)-N'-(1-adamantyl)-N-methylguanidine; N-(anthracenyl)-N'-(1-adamantyl)-N'-methylguanidine; N-(anthracenyl)-N'-(1-adamantyl)-N,N'-dimethylguanidine; N-(anthracenyl)-N'-(2-adamantyl)guanidine; N-(anthracenyl)-N'-(2-adamantyl)-N-methylguanidine; N-(anthracenyl)-N'-(2-adamantyl)-N'-methylguanidine; N-(anthracenyl)-N'-(2-adamantyl)-N,N'-dimethylguanidine; N-(phenanthracenyl)-N'-(1-adamantyl)guanidine; N-(phenanthracenyl)-N'-(1-adamantyl)-N-methylguanidine; N-(phenanthracenyl)-N'-(1-adamantyl)-N'-methylguanidine; N-(phenanthracenyl)-N'-(1-adamantyl)-N,N'-dimethylguanidine; N-(phenanthracenyl)-N'-(2-adamantyl)guanidine; N-(phenanthracenyl)-N'-(2-adamantyl)-N-methylguanidine; N-(phenanthracenyl)-N'-(2-adamantyl)-N'-methylguanidine; N-(phenanthracenyl)-N'-(2-adamantyl)-N,N'-dimethylguanidine; N-(fluorenyl)-N'-(1-adamantyl) guanidine; N-(fluorenyl)-N'-(1-adamantyl)-N-methylguanidine; N-(fluorenyl)-N'-(1-adamantyl)-N'-methylguanidine; N-(fluorenyl)-N'-(1-adamantyl)-N,N'-dimethylguanidine; N-(fluorenyl)-N'-(2-adamantyl) guanidine; N-(fluorenyl)-N'-(2-adamantyl)guanidine; N-(fluorenyl)-N'-(2-adamantyl)-N'-methylguanidine; N-(fluorenyl)-N'-(2-adamantyl)-N-methylguanidine; N-(fluorenyl)-N'-(1-adamantyl)-N'-methylguanidine; N-(fluorenyl)-N'-(2-adamantyl)-N,N'-dimethylguanidine; N-(fluorenyl)-N'-(methoxynaphthyl)guanidine; N-(fluorenyl)-N'-(methoxynaphthyl)-N-methylguanidine; N-(fluorenyl)-N'-(methoxynaphthyl)-N'-methylguanidine; N-(fluorenyl)-N'-(methoxynaphthyl)-N,N'-dimethylguanidine; and pharmaceutically acceptable salts thereof. Such compounds are disclosed in International Application PCT/US95/01536, incorporated herein by reference.

Further preferred compounds for use in the methods of the invention include compounds of the following Formula XIV:

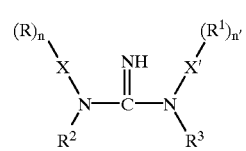

wherein R and $R^1$ are each independently substituted or unsubstituted alkyl having from 1 to about 20 carbon atoms, substituted or unsubstituted alkenyl having from 2 to about 20 carbon atoms, substituted or unsubstituted alkynyl having from 2 to about 20 carbon atoms, substituted or unsubstituted alkoxy having from 1 to about 20 carbon atoms, substituted or unsubstituted aryloxy having from 6 to about 20 carbon atoms, substituted or unsubstituted aralkoxy having from 6 to about 20 carbon atoms, substituted or unsubstituted aminoalkyl having 1 to about 20 carbon atoms, substituted or unsubstituted alkylthio having from 1 to about 20 carbon atoms, substituted or unsubstituted alkylsulfinyl having from 1 to about 20 carbon atoms, substituted or unsubstituted alkylsulfonyl having 1 to about 20 carbon atoms, substituted or unsubstituted carbocyclic aryl having at least 5 ring atoms, substituted or unsubstituted aralkyl having at least 5 ring atoms, or a substituted or unsubstituted heteroaromatic or heteroalicyclic group having 1 to 3 rings, 3 to 8 ring members in each ring and 1 to 3 heteroatoms;

$R^2$ and $R^3$ are each independently hydrogen or a group as defined for R and $R^1$ above, and preferably are each substituted or unsubstituted alkyl, alkenyl, alkynyl, alkoxy, aminoalkyl, alkylthio or alkylsulfinyl; or $R^1$ and $R^3$ together form a ring having 5 or more ring members;

n and n' independently are each equal to 1, 2, or 3;

X and X' are each independently a chemical bond (i.e., a bond between the guanidine nitrogen and R or $R^1$), substituted or unsubstituted alkylene having from 1 to about 8 carbon atoms, substituted or unsubstituted alkenylene having from 2 to about 8 carbon atoms, or substituted or unsubstituted alkynylene having from 2 to about 8 carbon atoms, substituted or unsubstituted heteroalkylene having from 1 to about 8 carbon atoms, substituted or unsubstituted heteroalkenylene having 2 to about 8 carbon atoms, and substituted or unsubstituted heteroalkynylene having from 2 to about 8 carbon atoms, with at least one X and X' being other than a bond; and pharmaceutically acceptable salts thereof. Preferred compounds of Formula XIV include those where X is substituted or unsubstituted alkylene or alkenylene having 1 to about 3 carbon atoms. Specifically preferred compounds of Formula XIV include N-5-acenaphthyl-N'-benzhydrylguanidine; N-5-acenaphthyl-N'-benzhydryl-N-methylguanidne; N-5-acenaphthyl-N'-benzhydryl-N'-methylguanidine; N-5-acenaphthyl-N'-benzhydryl-N,N'-dimethylguanidine; N-3-acenaphthyl-N'- benzhydrylguanidine; N-3-acenaphthyl-N'-benzhydryl-N-methylguanidine; N-3-acenaphthyl-N'-benzhydryl-N'-methylguanidine; N-3-acenaphthyl-N'-benzhydryl-N,N'-dimethylguanidine; N-(5-acenaphthyl)-N'-[(1-naphthyl)-methyl]guanidine; N-(5-acenaphthyl)-N'-[(1-naphthyl)-methyl]-N-methylguanidine; N-(5-acenaphthyl)-N'-[(1-naphthyl)-methyl]-N'-methylguanidine; N-(5-acenaphthyl)-N'-[(1-naphthyl)-methyl]-N,N'-dimethylguanidine; N-(5-acenaphthyl)-N'-(1-methyl-2-phenoxyethyl)guanidine; N-(5-acenaphthyl)-N'-(1-methyl-2-phenoxyethyl)-N-methylguanidine; N-(5-acenaphthyl)-N'-(1-methyl-2-phenoxyethyl)-N'-methylguanidine; N-(5-acenaphthyl)-N'-(1-methyl-2-phenoxyethyl)-N,N'-dimethylguanidine; N-(5-acenaphthyl)-N'-(1-methyl-2-(4-chlorophenyl)ethyl)guanidine; N-(5-acenaphthyl)-N'-(1-methyl-2-(4-chlorophenyl)ethyl)-N-methylguanidine; N-(5-acenaphthyl)-N'-(1-methyl-2-(4-chlorophenyl)ethyl)-N'-methylguanidine; N-(5-acenaphthyl)-N'-(1-methyl-2-(4-chlorophenyl)ethyl)-N,N'-dimethylguanidine; N-(5-acenaphthyl)-N'-(1,2-diphenylethyl)guanidine; N-(5-acenaphthyl)-N'-(1,2-diphenylethyl)-N-methylguanidine; N-(5-acenaphthyl)-N'-(1,2-diphenylethyl)-N'-methylguanidine; N-(5-acenaphthyl)-N'-(1,2-diphenylethyl)-N,N'-dimethylguanidine; N-(5-acenaphthyl)-N'-(3-phenylpropyl)guanidine; N-(5-acenaphthyl)-N'-(3-phenylpropyl)-N-methylguanidine; N-(5-acenaphthyl)-N'-(2-methyl-2-phenylethyl)-N'-methylguanidine; N,N'-(sec-butylphenyl)-N'-(2-phenoxyethyl)guanidine; N,N'-(sec-butylphenyl)-N'-(2-phenoxyethyl)-N-methylguanidine; N,N'-(sec-butylphenyl)-N'-(2-phenoxyethyl)-N'-methylguanidine; N,N'-(sec-butylphenyl)-N'-(2-phenoxyethyl)-N,N'-dimethylguanidine; N-(5-acenaphthyl)-N'-((4-tert-butylphenyl)-(4-sec-butylphenyl)-methyl)guanidine; N-(5-acenaphthyl)-N'-((4-tert-butylphenyl)-(4-sec-butylphenyl)-methyl)-N-methylguanidine; N-(5-acenaphthyl)-N'-((4-tert-butylphenyl)-(4-sec-butylphenyl)-methyl)-N'-methylguanidine; N-(5-acenaphthyl)-N'-((4-tert-butylphenyl)-(4-sec-butylphenyl)-methyl)-N,N'-dimethylguanidine; N-(4-butoxyphenyl)-N,N'-bis(4-tert-butylbenzyl)guanidine; N-(4-butoxyphenyl)-N,N'-bis(4-tert-butylbenzyl)-N-methylguanidine; N-(4-butoxyphenyl)-N,N'-bis(4-tert-butylbenzyl)-N'-methylguanidine; N-(4-butoxyphenyl)-N,N'-bis(4-tert-butylbenzyl)-N,N'-dimethylguanidine; and pharmaceutically acceptable salts of said compounds. Such compounds are disclosed in International Application PCT/US95/01536, incorporated herein by reference.

Further preferred compounds for use in the present methods are substituted guanidines (including compounds of Formulae I, II and III above) that have a phenyl substituent that is ring substituted by one or more branched groups such as branched alkyl e.g. sec-butyl or tert-butyl, and/or one or more substituted or unsubstituted aralkoxy substituents, particularly substituted or unsubstituted benzyloxy. Preferably the phenyl substituent is ring substituted by such branched or aryloxy groups at 1, 2 or 3 ring positions. Para-substitution and meta-substitution of the phenyl substituent is preferred. Specifically preferred compounds include N,N'-di-(4-sec-butylphenyl)guanidine; N,N'-di-(4-sec-butylphenyl)-N-methylguanidine; N,N'-di-(4-sec-butylphenyl)-N,N'-dimethylguanidine; N-(2-naphthyl)-N'-(4-isopropylphenyl)guanidine; N-(2-naphthyl)-N'-(4-isopropylphenyl)-N-methylguanidine; N-(2-naphthyl)-N'-(4-isopropylphenyl)-N'-methylguanidine; N-(2-naphthyl)-N'-(4-isopropylphenyl)-N,N'-dimethylguanidine; N,N'-bis(4-tert-butylphenyl)guanidine; N,N'-bis(4-tert-butylphenyl)-N-methylguanidine; N,N'-bis(4-tert-butylphenyl)-N'-methylguanidine; N,N'-bis(4-tert-butylphenyl)-N,N'-dimethylguanidine; N-(4-sec-butylphenyl)-N'-(2,3,4-trichlorophenyl)guanidine; N-(4-sec-butylphenyl)-N'-(2,3,4-trichlorophenyl)-N-methylguanidine; N-(4-sec-butylphenyl)-N'-(2,3,4-trichlorophenyl)-N'-methylguanidine; N-(4-sec-butylphenyl)-N'-(2,3,4-trichlorophenyl)-N,N'-dimethylguanidine; N-(4-methoxy-1-naphthyl)-N'-(2,3,4-trichlorophenyl)guanidine; N-(4-methoxy-1-naphthyl)-N'-(2,3,4-trichlorophenyl)-N-methylguanidine; N-(4-methoxy-1-naphthyl)-N'-(2,3,4-trichlorophenyl)-N'-methylguanidine; N-(4-methoxy-1-naphthyl)-N'-(2,3,4-trichlorophenyl)-N,N'-dimethylguanidine; N,N'-bis-(4-sec-butylphenyl)-2-iminopyrimidazolidine; N,N'-bis(3-biphenyl)guanidine; N,N'-bis(3-biphenyl)-N-methylguanidine; N,N'-bis(3-biphenyl)-N'-methylguanidine; N,N'-bis(3-biphenyl)-N,N'-dimethylguanidine; N,N'-di-(3-tert-butylphenyl)guanidine; N,N'-di-(3-tert-butylphenyl)-N-methylguanidine; N,N'-di-(3-tert-butylphenyl)-N'-methylguanidine; N,N'-di-(3-tert-butylphenyl)-N,N'-dimethylguanidine; N,N'-bis-(4-methoxy-1-naphthyl)guanidine; N,N'-bis-(4-methoxy-1-naphthyl)-N-methylguanidine; N,N'-bis-(4-methoxy-1-naphthyl)-N'-methylguanidine; N,N'-bis-(4-methoxy-1-naphthyl)-N,N'-dimethylguanidine; N,N'-bis-(3-sec-butylphenyl)guanidine; N,N'-bis-(3-sec-butylphenyl)-N-methylguanidine; N,N'-bis-(3-sec-butylphenyl)-N'-methylguanidine; N,N'-bis-(3-sec-butylphenyl)-N,N'-methylguanidine; N,N'-bis(4-n-butylphenyl)guanidine; N,N'-bis(4-n-butylphenyl)-N-methylguanidine; N,N'-bis(4-n-butylphenyl)-N'-methylguanidine; N,N'-bis(4-n-butylphenyl)-N,N'-dimethylguanidine; N,N'-(sec-butylphenyl)-N'-(n-pentyl)guanidine; N,N'-bis(3-benzyloxyphenyl)guanidine; N,N'-bis(3-benzyloxyphenyl)-N-methylguanidine; N,N'-bis(3-benzyloxyphenyl)-N,N'-dimethylguanidine; N,N'-bis(4-benzyloxyphenyl)guanidine; N,N'-bis(4-benzyloxyphenyl)-N-methylguanidine; N,N'-bis(4-benzyloxyphenyl)-N,N'-dimethylguanidine; N-(3-benzyloxyphenyl)-N'-(4-benzyloxyphenyl)guanidine; N-(3-benzyloxyphenyl)-N'-(4-benzyloxyphenyl)-N-methylguanidine; N-(3-benzyloxyphenyl)-N'-(4benzyloxyphenyl)-N'-methylguanidine; N-(3-benzyloxyphenyl)-N'-(4-benzyloxyphenyl)-N,N'-dimethylguanidine; and pharmaceutically acceptable salts of said compounds. Such compounds are disclosed in International Application PCT/US95/01536, incorporated herein by reference.

With respect to the above compounds for use in the present methods, in addition to the above-discussed suitable and preferred substituent groups, it is further noted that suitable halogen groups of compounds for use in the present methods include F, Cl, Br and I; preferred alkyl groups include those having 1 to about 12 carbon atoms, more preferably 1 to about 10 carbon atoms such as methyl, ethyl, n-propyl, iso-propyl, n-butyl, t-butyl, iso-butyl, sec-butyl, pentyl, hexyl, heptyl, etc.; and preferred alkenyl and alkynyl groups include those groups having one or more unsaturated linkages, preferably one or two unsaturated linkages and from 2 to about 12 carbon atoms, more preferably 2 to about 8 carbon atoms. Each of the terms alkyl, alkenyl and alkynyl as used herein may refer to both cyclic and noncyclic groups, unless otherwise specified. Preferred alkoxy groups of compounds for use in the present methods include groups having one or more oxygen linkages and from 1 to about 12 carbon atoms, more preferably 1 to about 8 carbon atoms, still more preferably 1 to about 6 carbons. Straight and branched chain butoxy, pentoxy, and hexoxy may be particularly preferred for some compounds. Methoxy, ethoxy and propoxy also may be preferred. Preferred aryloxy groups of compounds for use in the present methods have 6 to about 20 carbon atoms or from 6 to about 12 carbon atoms and include an oxygen atom. Substituted or unsubstituted phenoxy and naphthoxy are preferred aryloxy groups. Preferred aralkoxy groups of compounds for use in methods of the invention from 6 to about 20 carbon atoms and include an alkoxy group as specified above that contains one or more aryl substituents, particularly one or more carbocyclic aryl substituents. Typically an oxygen will be the terminal group of the substituent. Substituted or unsubstituted benzyloxy (i.e., $C_6H_5CH_2O$—) are preferred aralkoxy groups. Preferred alkylthio groups of compounds for use in the present methods include groups having one or more thioether linkages and from 1 to about 12 carbon atoms, more preferably 1 to about 8 carbon atoms, still more preferably 1 to about 6 carbons. Preferred aminoalkyl groups of compounds for use in the present methods include those groups having one or more primary, secondary and/or tertiary amine groups, and from 1 to about 12 carbon atoms, more preferably 1 to about 8 carbon atoms, still more preferably 1 to about 6 carbons. Secondary and tertiary amine groups are generally more preferred than primary amine moieties. Preferred alkylsulfinyl groups of compounds for use in the present methods have one or more sulfinyl (SO) groups, more typically one sulfinyl group, and from 1 to about 12 carbon atoms, more preferably 1 to about 6 carbons, and even more preferably 1–3 carbon atoms. Preferred alkylsulfonyl groups of compounds for use in the present methods have one or more sulfono ($SO_2$) groups, more typically one sulfono group, and from 1 to about 12 carbon atoms, more preferably 1 to about 6 carbons, and even more preferably 1–3 carbon atoms. Preferred alkenylene and alkynylene groups of compounds for use in the present methods have one or two carbon-carbon multiple bonds. Preferred heteroalkylene, heteroalkenylene and heteroalkynylene groups of compounds for use in the present methods contain 1 to about 3 heteroatoms consisting of N, O and/or S atoms. In general, heteroatoms of substituent groups will be N, O or S. Suitable heteroaromatic and heteroalicyclic groups of compounds for use in methods of the invention contain one or more N, O or S atoms and include, e.g., quinolinyl including 8-quinolinyl, indolinyl including 5-indolinyl, furyl, thienyl, pyrrolyl, thiazolyl, pyridyl, pyrimidinyl, pyridazinyl, oxazolyl and phthalimido groups all of which may be optionally independently substituted at one or more available positions and/or fused to a benzene ring; and substituted or unsubstituted tetrahydrofuranyl, tetrahydropyranyl, piperidinyl, piperazinyl, morpholino, pyrrolidinyl groups, pyrazinyl, coumarinyl, tetrahydroquinolinyl, tetrahydroisoquinolinyl, benzothiazolyl, benzotriazolyl, and bezimidazolyl. Preferred carbocyclic aryl groups include those having about 6 to about 20 carbons, more preferably about 1 to 3 separate or fused rings and from 6 to about 18 carbon atoms such as phenyl, naphthyl, acenaphthyl, phenanthryl, anthracyl and fluorene groups. Suitable aralkyl groups contain 1 to 3 separate of fused rings and from 6 to about 18 carbon atoms such as benzyl and methylenenaphthyl (—$CH_2$-naphthyl).

Said substituted moieties or substituents of compounds for use in the present methods (e.g. groups designated as "substituted" rather than "unsubstituted" in Formulae IV, XI, XIII, XIV etc.) may be substituted at one or more available positions by one or more suitable groups such as, e.g., halogen such as F, Cl, Br, or I; cyano; hydroxyl; nitro; azido; carboxy; carbocyclic aryl; alkyl groups including alkyl groups having from 1 to about 12 carbon atoms or from 1 to about 6 carbon atoms; alkenyl and alkynyl groups including groups having one or more unsaturated linkages and from 2 to about 12 carbon atoms or from 2 to about 6 carbon atoms; alkoxy groups such as those groups having one or more oxygen linkages and from 1 to about 12 carbon atoms or from 1 to about 6 carbon atoms; alkylthio groups such as those groups having one or more thioether linkages and from 1 to about 12 carbon atoms or from 1 to about 6 carbon atoms; aminoalkyl groups such as groups having one or more N atoms and from 1 to about 12 or 1 to about 6 carbon atoms; alkylsulfinyl such as those groups having one or more sulfinyl groups and from 1 to about 12 carbon atoms or from 1 to about 6 carbon atoms; alkylsulfonyl such as those groups having one or more sulfono groups and from 1 to about 12 carbon atoms or from 1 to about 6 carbon atoms.

Specifically preferred substituted groups include carboxylic acyl groups, preferably having from 1 to about 12 or 1 to about 6 carbon atoms such as acetyl, propanoyl, isopropanoyl, butanoyl, sec-butanoyl, pentanoyl and hexanoyl groups. Also preferred substituted moieties are alkaryl groups which include single and multiple ring compounds, including multiple ring compounds that contain separate and/or fused aryl groups, e.g., above-mentioned aryl groups substituted by one or more $C_1$–$C_{10}$ alkyl groups such as phenylmethyl, phenylethyl, phenylpropyl, phenylbutyl, phenylpentyl and phenylhexyl groups as well as the branched chain isomers thereof such as tert-butylphenyl, sec-butylphenyl, etc. Haloalkyl and haloalkoxy are also preferred, particularly fluoroalkyl and fluoroalkoxy such as trifluoromethyl and trifluoroalkoxy. Aroyl groups are also preferred substituted groups such as carbonyl substituted by phenyl, naphthyl, acenaphthyl, phenanthryl, and anthracyl groups and carboxylic acyl groups substituted by one or more aryl groups, e.g., diphenylacetoxy and fluorenecarboxy groups. Aralkanoyl groups are also preferred and include carbonyl substituted by the aralkyl groups described above. Aralkoxy groups are also preferred substituted groups and include alkoxy groups substituted by phenyl, naphthyl, acenaphthyl, phenanthryl, and anthracyl groups. Preferred substituted aryl groups include the above described aryl groups substituted by halo, hydroxy, alkyl, alkenyl, alkynyl, alkoxy, amino, aminoalkyl, thioalkyl and the like.

Other compounds suitable for use in the present methods include N-(5-acenaphthyl)-N'-(1,2,3,4-tetrahydroquinolinyl)guanidine; N-(5-acenaphthyl)-N'-(1,2,3,4-tetrahydroquinolinyl)-N-methylguanidine; N-(5-acenaphthyl)-N'-(1,2,3,4-tetrahydroquinolinyl)-N'-methylguanidine; N-(5-acenaphthyl)-N'-(1,2,3,4-tetrahydroquinolinyl)-N,N'-dimethylguanidine; N-(3-acenaphthyl)-N'-(indolinyl)guanidine; N-(3-acenaphthyl)-N'-(indolinyl)-N-methylguanidine; N-(3-acenaphthyl)-N'-(indolinyl)-N'-methylguanidine; N-(3-acenaphthyl)-N'-(indolinyl)-N,N'-methylguanidine; N-(5-acenaphthyl)-N'-(piperonyl)guanidine; N-(5-acenaphthyl)-N'-(piperonyl)-N-methylguanidine; N-(5-acenaphthyl)-N'-(piperonyl)-N'-methylguanidine; N-(5-acenaphthyl)-N'-(piperonyl)-N,N'-dimethylguanidine; N-(2-naphthyl)-N'-(2-adamantyl) guanidine; N-(2-naphthyl)-N'-(2-adamantyl)-N-methylguanidine; N-(2-naphthyl)-N'-(2-adamantyl)-N'-methylguanidine; N-(2-naphthyl)-N'-(2-adamantyl)-N,N'-dimethylguanidine; N,N'-bis-(5-indanyl)-guanidine; N,N'-bis(6-benz[cd]indolinyl-2[1H]-one)guanidine; N-(3-sec-butylphenyl)-N-(4-tert-butylbenzyl)guanidine; N-(3-tert-butylphenyl)-N-(4-tert-butylbenzyl)guanidine; N-(3-pentoxyphenyl)-N-(4-tert-butylbenzyl)guanidine; N-(5-acenaphthyl)-N-(4-benzyloxybenzyl)guanidine; N-(4-secbutylphenyl)-N-(4-benzyloxybenzyl)guanidine; N-(4-benzyloxyphenyl)-N-(4-benzyloxybenzyl)guanidine; N-(5-acenaphthyl)-N-(3-benzyloxybenzyl)guanidine; N-(4-isopropylphenyl)-N-(4-tert-butylbenzyl)guanidine; N-(4-benzyloxyphenyl)-N-(4-tert-butylbenzyl)guanidine; N-(4-hexylphenyl)-N-(4-tert-hexylbenzyl)guanidine; N-(4-sec-butylphenyl)-N-(4-t-butylbenzyl)-N'-pyrrolidinylguanidine; N-(4-sec-butylphenyl)-N-(4-t-butylbenzyl)-N'-(4-thiomorpholinyl)guanidine; N-(4-sec-butylphenyl)-N-(4-tert-butylbenzyl)-N'-piperidinylguanidine; N-(4-sec-butylphenyl)-N-(4-tert-butylbenzyl)-N'-(4-morpholinyl)guanidine; N-(4-sec-butylphenyl)-N-(4-tert-butylbenzyl)-N'-(4-propylpiperidinyl)guanidine; N-(4-butoxyphenyl)-N-(4-tert-butylbenzyl)-N'-(4-piperidinyl)guanidine; N-(4-sec-butylphenyl)-N-(4-tert-butylbenzyl)-N'-(4-benzylpiperidinyl)guanidine; N-(4-benzyloxyphenyl)-N-(4-tert-butylbenzyl)-N'-(4-morpholinyl)guanidine; N-(4-sec-butylphenyl)-N-(4-tert-butylbenzyl)-N'-(1,2,3,4-tetrahydroisoquinolinyl)guanidine; N-(3-butoxy-4-methoxyphenyl)-N-(4-tert-butylbenzyl)-N'-(4-morpholinyl)guanidine; N-(4-sec-butylphenyl)-N-(4-tert-butylbenzyl)-N'-(3,5-dimethyl-4-morpholinyl)guanidine; N-(4-tert-butylphenyl)-N-(4-tert-butylbenzyl)-N'-(4-sec-butylphenyl)-N'-(methyl)guanidine; N-(4-sec-butylphenyl)-N-(4-tert-butylbenzyl)-N'-(4-sec-butylphenyl)-N'-(methyl)guanidine; N-(4- sec-butylphenyl)-N-(4-tert-butylbenzyl)-N'-(phenyl)guanidine; N-(4-sec-butylphenyl)-N-(4-tert-butylbenzyl)-N'-(4-chlorophenyl)guanidine; N-(4-butoxylphenyl)-N-(4-tert-butylbenzyl)-N'-(phenyl)guanidine; N-(4-sec-butylphenyl)-N-(4-tert-butylbenzyl)-N'-(phenyl)-N'-methylguanidine; N-(4-sec-butylphenyl)-N-(4-tert-butylbenzyl)-N'-(3,4-dichlorophenyl)guanidine; N-(4-hexylphenyl)-N-(4-tert-hexylbenzyl)-N'-phenylguanidine; N-(4-sec-butylphenyl)-N-(4-tert-butylbenzyl)-N'-(4-benzyloxyphenyl)guanidine; N,N'-bis-(4-tert-butylphenyl)-N,N'-dimethylguanidine; N-(4-benzyloxyphenyl)-N'-(4-tert-butylphenyl)guanidine; N,N'-bis-(3-(1'-methyl-2'-phenyl)ethyl)guanidine; N-methyl-N-4-benzyloxyphenyl-N'-(4-tert-butylphenyl)guanidine; N,N'-bis-(4-hexylphenyl)guanidine; N-(3-(1-(4'-ethoxy)benzyl)phenethyl)-N'-(4-tert-butylphenyl)guanidine; N-(4-benzyloxyphenyl)-N'-methyl-N-(4-tert-butylphenyl)guanidine; N-(3-(4-tert-butylbenzyloxy)phenyl)-N'-(4-tert-butylphenyl)guanidine; N-(3-(1'-benzylbutyl)phenyl)-N'-(4-tert-butylphenyl)guanidine; N,N'-bis-(4-butylphenyl)-N-methylguanidine; N,N'-bis-(4-tert-butylphenyl)-N,N'-dimethylguanidine; N-(3-naphthaloxyphenyl)-N'-(4-tertbutylphenyl)guanidine; N-(4-benzyloxyphenyl)-N'-(4-butylphenyl)guanidine; N,N'-bis-(4-butylphenyl)-N-butylguanidine; N-3-(benzyloxymethyl)phenyl-N'-(4-tert-butylphenyl)guanidine; N-(3,4-bis-butyloxyphenyl)-N'-(4-tert-butylphenyl)guanidine; N-(3-benzyloxy)phenyl-N'-(4-tert-butylphenyl)guanidine; N,N'-bis-(3-butoxy-4-methoxy)phenylguanidine; N-(4-benzyloxyphenyl)-N-methyl-N'-(4-butylphenyl)guanidine; N-(4-benzyloxyphenyl)-N'-methyl-N'-(4-butylphenyl)guanidine; N,N'-bis-(6-tetralinyl)guanidine; N-(6-tetralinyl)-N'-(4-tert-butylphenyl)guanidine; N-(5-acenaphthyl)-N'-(6-benzothiozolyl)guanidine; N-(5-acenaphthyl)-N'-(6-N-benzylindolinyl)guanidine; N-(5-acenaphthyl)-N'-(4-benzo-2,1,3-thiadizaole)guanidine; N-(5-acenaphthyl)-N'-[4-(6-methyl-benzothiazole)phenylguanidine; N-(5-acenaphthyl)-N'-(1-benz[cd]indolinyl)guanidine; N-(5-acenaphthyl)-N'-(6-benz[cd]indo-2[1H]-one)guanidine; N-(4-butoxyphenyl)-N'-(4-chlorophenylethyl)guanidine; N-(4-benzyloxyphenyl)-N,N'-diphenylguanidine; N-(4-benzyloxyphenyl)-N'-benzyl-N'-phenylguanidine; N-(3-benzyloxyphenyl)-N'-(4-thiobenzylphenyl)guanidine; N,N'-bis(4-(phenylthio)phenyl)guanidine; N,N'-bis(3-(phenylthio)phenyl)guanidine; N-(5-acenaphthyl)-N'-(2-phenylethyl)guanidine; N-(5-acenaphthyl)-N'-(3-butoxypropyl)guanidine; N,N'-bis(2,2-diphenylethyl)guanidine; N-(4-butoxyphenyl)-N'-(4-chlorophenylethyl)guanidine; N-(4-butoxyphenyl)-N-(4-chlorobenzhydryl)guanidine; (5-acenaphthyl)-N'-(phenethyl)-N'-benzylguanidine; N-(4-benzyloxyphenyl)-N'-(3-benzyloxyphenyl)-N'-(4-chlorobenzyl)guanidine; N,N'-bis(4-benzyloxyphenyl)-N'-methylguanidine; N-(4-benzyloxyphenyl)-N'-(3-benzyloxyphenyl)-N'-(4-chlorobenzyl)guanidine; N-(3-benzyloxyphenyl)-N'-(4-benzyloxyphenyl)-N'-phenylguanidine; N-(4-sec-butylphenyl)-N'-(4-isopropoxyphenyl)-N'-phenylguanidine; N-(4-benzyloxyphenyl)-N'-(4-benzyloxyphenyl)-N'-phenylguanidine; N,N'-bis(3-octyloxyphenyl)guanidine; N,N'-bis(4-butoxyphenyl)guanidine; N,N'-bis(4-phenoxyphenyl)guanidine; N-(3-benzyloxyphenyl)-N'-(4-phenoxyphenyl)guanidine; N-(3-benzyloxyphenyl)-N'-(4-phenylazophenyl)guanidine; N,N'-bis(3-benzyloxyphenyl)-N'-methylguanidine; N-(4-benzyloxphenyl)-N'-(4-benzyloxyphenyl)-N'-methylguanidine; N-(4-butoxyphenyl)-N'-(4-isopropoxyphenyl)guanidine; N-N'-bis(4-(1-hydroxybutyl)phenyl)guanidine; N-(4-butoxyphenyl)-N'-(3-methoxyphenyl)-N'-phenylguanidine; N-(4-secbutylphenyl)-N'-phenyl-N'-(4-(2-isopropoxy)phenyl)guanidine; and N-(4-n-butoxyphenyl)-N'-(2-(4-chlorophenyl)ethyl)guanidine; and pharmaceutically acceptable salts of thereof.

Compounds for use in methods of the invention can be prepared in accordance with disclosed procedures. For preferred synthetic protocols, see the above-discussed U.S. Pat. Nos. 4,906,779; 5,011,834; 5,190,976; 5,262,568; 5,403,861; and International Applications PCT/US91/03594; PCT/US92/01050; PCT/US92/03354; PCT/US94/06008; PCT/US94/13245; PCT/US94/13541; and PCT/US95/01536, which are each incorporated herein by reference. See also U.S. Pat. No. 5,298,657 to Durant et al., incorporated herein by reference.

Thus, for example, guanidine compounds useful in methods of the invention can be readily prepared by the reaction of an amine, typically an amine salt such as an amine hydrochloride, with a preformed alkyl or aryl cyanamide (see S. R. Safer, et al., *J. Org. Chem.*, 13:924 (1948)) or the corresponding N-substituted alkyl or aryl cyanamide. This is a particularly suitable method for producing N,N'-diaryl-N'-alkyl in which the substituents are not identical. For a synthesis of asymmetrical guanidines, see G. J. Durant et al., *J. Med. Chem.*, 28:1414 (1985), and C. A. Maryanoff et al., *J. Org. Chem.*, 51:1882 (1986).

More particularly, substituted guanidines useful in methods of the invention can be prepared suitably by reaction of an appropriate amine salt such as an amine hydrochloride with a slight molar excess (e.g., ca. 1.1 molar equivalent) of a substituted cyanamide in a suitable solvent such as toluene or chlorobenzene under an inert atmosphere such as argon or nitrogen. The reaction is then heated, e.g. from about 110 to 120° C. for 2 to about 16 hours until reaction completion, e.g. as indicated by thin layer chromatography. The reaction solution is then cooled to room temperature, and suitably diluted with a solvent such as absolute alcohol. The solvent is then removed under reduced pressure to provide the desired substituted guanidine. The crude product then can be purified e.g. by recrystallization and/or chromatography. The cyanamide and amine reagents with appropriate substituents are commercially available or can be readily prepared by known procedures. For example, the cyanamide starting material can be synthesized from the correspondingly substituted amine by treatment with cyanogen bromide (BrCN) in suitable solvent such as dry ethyl ether. The amine hydrochloride can be obtained by treatment of an appropriate amine with an excess of HCl. An alkylsulfinyl-substituted or alkylsulfonyl-substituted reagent, that can provide correspondingly substituted guanidines as described above, can be provided by oxidation (e.g., $H_2O_2$) of alkylthio-substituted reagents.

As discussed above, methods are provided for treatment of reduced flow of blood or other nutrients to retinal tissue and/or optic nerve. In particular, methods are provided for treatment of retinal trauma and ischemic degeneration, optic nerve injury and associated disorders comprising the administration of an effective amount of one or more of the above-described compounds to a subject, particularly a mammal such as a human, in need of such treatment.

For example, methods are provided for treating and/or prophylaxis of disorders associated with ischemic retinal diseases such as diabetic retinopathy, atherosclerosis, venous capillary insufficiency, obstructive arterial or venous retinopathies, senile macular degeneration, cystoid macular edema and glaucoma.

Further provided are methods for treatment and/or prophylaxis of a mammal that suffers from or is susceptible to retinal ischemia as a result of a tumor, e.g. such that blood flow or other nutrient supply to retinal tissue is decreased, or as a result of injury or other occurrence such as stroke, heart attack, extra-corporal circulation or the like where blood flow or nutrient supply to retinal tissue can be reduced.

Methods are also provided for treating trauma or injury to retinal tissue or optic nerve, comprising the administration of an effective amount of one or more of the above-described compounds to a subject, particularly a mammal such as a human, in need of such treatment.

Methods are further provided for treatment of a subject undergoing laser retinal reattachment, comprising administering an effective amount of an or more of the above-described compounds to the subject such as a human in conjunction with the reattachment procedure.

In the present methods, the above disclosed compounds may be administered to a subject by a variety of routes including oral, rectal, nasal, topical (including eye drops, buccal, sublingual), vaginal or parenteral (including subcutaneous, intramuscular and intradermal) administration. Topical will be a frequently preferred route of administration, particularly by eye drops. Intraviteal injection of a compound also may be a preferred administration route to provide more direct treatment to an ischemic retina.

Compounds for use in the present methods are suitably administered to a subject in the protonated and water-soluble form, e.g., as a pharmaceutically acceptable salt of an organic or inorganic acid, e.g., hydrochloride, sulfate, hemi-sulfate, phosphate, nitrate, acetate, oxalate, citrate, maleate, mesylate, etc.

It also should be appreciated that compounds for use in the present methods may exist as any one of a number tautomeric forms. Each of such tautomeric forms are within the scope of the invention, including as defined by the above formulae.

Compounds for use in the present methods can be employed, either alone or in combination with one or more other therapeutic agents, as a pharmaceutical composition in mixture with conventional excipient, i.e., pharmaceutically acceptable organic or inorganic carrier substances suitable for a desired route of administration which do not deleteriously react with the active compounds and are not deleterious to the recipient thereof. Suitable pharmaceutically acceptable carriers include but are not limited to water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethyl-cellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously react with the active compounds.

For parenteral application, particularly suitable are solutions, preferably oily or aqueous solutions as well as suspensions, emulsions, or implants, including suppositories. Ampules are convenient unit dosages.

For enteral application, particularly suitable are tablets, dragees or capsules having talc and/or carbohydrate carrier binder or the like, the carrier preferably being lactose and/or corn starch and/or potato starch. A syrup, elixir or the like can be used wherein a sweetened vehicle is employed. Sustained release compositions can be formulated including those wherein the active component is protected with differentially degradable coatings, e.g., by microencapsulation, multiple coatings, etc.

It will be appreciated that the actual preferred amounts of active compounds used in a given therapy will vary according to the specific compound being utilized, the particular compositions formulated, the mode of application, the particular site of administration, etc. Optimal administration rates for a given protocol of administration can be readily ascertained by those skilled in the art using conventional dosage determination tests conducted with regard to the foregoing guidelines. In general, a suitable effective dose of one or more the above-described compounds, particularly when using the more potent compound(s), will be in the range of from 0.01 to 100 milligrams per kilogram of bodyweight of recipient per day, preferably in the range of from 0.01 to 20 milligrams per kilogram bodyweight of recipient per day, more preferably in the range of 0.05 to 4 milligrams per kilogram bodyweight of recipient per day. The desired dose is suitably administered once daily, or several sub-doses, e.g. 2 to 4 sub-doses, are administered at appropriate intervals through the day, or other appropriate schedule. Such sub-doses may be administered as unit dosage forms, e.g., containing from 0.05 to 10 milligrams of the above-described compound(s), per unit dosage, preferably from 0.2 to 2 milligrams per unit dosage.

The entire text of all documents cited herein are incorporated by reference herein.

This invention has been described in detail with reference to preferred embodiments thereof. However, it will be appreciated that those skilled in the art, upon consideration of this disclosure, may make modifications and improvements within the spirit and scope of the invention.

What is claimed is:

1. A method for treating decreased blood flow or nutrient supply to retinal tissue or optic nerve, or retinal ischemia or trauma, or optic nerve injury, comprising administering to a mammal in need of such treatment an effective amount of a compound of the following Formula I:

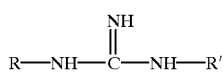

wherein R and R' each are a substituted or unsubstituted alkyl group of at least 4 carbon atoms, substituted or unsubstituted carbocyclic aryl groups of at least 6 carbon atoms, or a substituted or unsubstituted heterocyclic aromatic ring.

2. The method of claim 1 wherein the compounds is N'-di-m-tolylguanidine; N,N'-di-o-iodophenylguanidine; N,N'-di-o-ethylphenylguanidine; N,N'-di-m-ethylphenylguanidine; N,N'-bis(2-iodophenyl)guanidine; N,N'-bis(3-tolyl)guanidine; N,N'-bis(3-ethylphenyl)guanidine; N,N'-bis(2-isopropylphenyl)guanidine; N,N'-bis(3-isopropylphenyl)guanidine; N,N'-bis(1-naphthyl)guanidine; N,N'-bis(3-methoxyphenyl)guanidine; N,N'-bis(3-trifluoromethylphenyl)guanidine; N,N'-bis(4-fluoro-3-ethylphenyl)guanidine; N,N'-bis(3,5-diethylphenyl)guanidine; N,N'-bis(3-nitrophenyl)guanidine; N,N'-bis(4-fluoro-3-nitrophenyl)guanidine; N,N'-bis(3-nitro-5-ethylphenyl)guanidine; N,N'-bis(3-azidophenyl)guanidine; N,N'-bis(quinolin-8-yl)guanidine; N,N'-bis(coumarin-8-yl)guanidine; N,N'-dibutylguanidine; N'N'-diphenylguanidine; N,N'-di-o-tolylguanidine; N,N'-di-(2-methyl-4-bromophenyl)guanidine; N,N'-di-(2-methyl-4-iodophenyl)guanidine; N,N'-di(cyclohexyl)guanidine; N,N'-di-(m-propylphenyl)guanidine; N,N'-di-(1-tetralinyl)guanidine; N,N'-di(±-endo-2-norbornyl)guanidine; N,N'-di-(exo-2-norbornyl)guanidine; N,N-di-(4-indanyl)guanidine; N,N'-diadamantylguanidine; N,N'-dibenzylguanidine; N-(1-naphthyl)-N'-(o-ethylphenyl)guanidine; N-(1-naphthyl)-N'-(m-isopropylphenyl)guanidine; N-(1-naphthyl)-N'-(m-methoxyphenyl)guanidine; N-(1 -naphthyl)-N'-(4-indanyl)guanidine; N-(1-naphthyl)-N'-(m-ethylphenyl)guanidine; N-(m-ethylphenyl)'N'-(m-tolyl)guanidine; N-(m-ethylphenyl)-N'-(o-iodophenyl)guanidine; N-(m-ethylphenyl)-N'-(o-ethylphenyl)guanidine; N-(m-ethylphenyl)-N'-(o-isopropylphenyl)guanidine; N-(m-ethylphenyl)-N'-(m-isopropylphenyl)guanidine; N-(m-methylphenyl)-N'-(m-methoxyphenyl)guanidine; N-(m-ethylphenyl)-N'-(4-indanyl)guanidine; N-(m-ethylphenyl)-N'-(o-ethylphenyl)guanidine; N-(o-ethylphenyl)-N'-(m-tolyl)guanidine; N-(o-ethylphenyl)-N'-(o-iodophenyl)guanidine; N-(o-ethylphenyl)-N'-(o-isopropylphenyl)guanidine; N-(o-ethylphenyl)-N'-(m-isopropylphenyl)guanidine; N-(o-ethylphenyl)-N'-(m-methoxyphenyl)guanidine; N-(o-ethylphenyl)-N'-(4-indanyl)guanidine; N-(o-ethylphenyl)-N'-(m-ethylphenyl)guanidine; N-(o-iodophenyl)-N'-(m-tolyl)guanidine; N-(o-iodophenyl)-N'-(o-isopropylphenyl)guanidine; N-(o-iodophenyl)-N'-(m-isopropylphenylguanidine; N-(o-iodophenyl)-N'-(m-methoxyphenyl)guanidine; N-(o-iodophenyl)-N'-(4-indanyl)guanidine; N-(o-iodophenyl)-N'-(o-ethylphenyl)guanidine; N-(o-iodophenyl)-N'-(m-ethylphenyl)guanidine; N-(o-isopropylphenyl)-N'-(m-tolyl)guanidine; N-(o-isopropylphenyl)-N'-(m-isopropylphenyl)guanidine; N-(o-isopropylphenyl)-N'-(m-methoxyphenyl)guanidine; N-(o-isopropylphenyl)-N'-(4-indanyl)guanidine; N-(o-isopropylphenyl)-N'-(o-ethylphenyl)guanidine; N-(o-isopropylphenyl)-N'-(m-ethylphenyl)guanidine; N-(m-isopropylphenyl)-N'-(m-tolyl)guanidine; N-(m-isopropylphenyl)-N'-(m-methoxyphenyl)guanidine; N-(m-isopropylphenyl)-N'-(4-indanyl)guanidine; N-(m-isopropylphenyl)-N'-(o-ethylphenyl)guanidine; N-(m-isopropylphenyl)-N'-(m-ethylphenyl)guanidine; N-(m-methoxyphenyl)-N'-(m-tolyl)guanidine; N-(m-methoxyphenyl)-N'-(m-tolyl)guanidine; N-(2-4-di-iodo-5-hydroxyphenyl)-N'-(2-tolyl)guanidine; N-(1-naphthyl)-N'-(2-iodophenyl)guanidine; N-(1-naphthyl)-N'-(3-ethylphenyl)guanidine; N-(1-naphthyl)-N'-(2-isopropylphenyl)guanidine; N-(1-naphthyl)-N'-(3-tolyl)guanidine; N-(1-naphthyl)-N-(4-bromo-3-ethylphenyl)guanidine; N-(1-naphthyl)-N'-(6-methoxy-3-ethylphenyl)guanidine; N-(1-naphthyl)-N'-(4-nitro-3-ethylphenyl)guanidine; N-(1-naphthyl)-N'-[3-(1-hydroxyethyl)phenyl]guanidine; N-(4-fluoronaphthyl)-N'-(3-ethylphenyl)guanidine; N-(1-naphthyl)-N'-(4-fluoro-3-tolyl)guanidine; N-(1-naphthyl)-N'-(4-bromo-3-tolyl)guanidine; N-(1-naphthyl)-N'-(3-trifluoromethylphenyl)guanidine; N-(m-trifluoromethylphenyl)-N'-(m-tolyl)guanidine; N-(m-trifluoromethylphenyl)-N'-(o-isopropylphenyl)guanidine; N-(m-trifluoromethylphenyl)-N'-(m-isopropylphenyl)guanidine; N-(m-trifluoromethylphenyl)-N'-(m-methoxyphenyl)guanidine; N-(m-trifluoromethylphenyl)-N'-(4-indanyl)guanidine; N-(m-trifluoromethylphenyl)-N'-(o-ethylphenyl)guanidine; N-(m-trifluoromethylphenyl)-N'-(m-ethylphenyl)guanidine; N-(m-trifluoromethylphenyl)-N'-(o-iodophenyl)guanidine; N-(1-naphthyl)N'-(4-fluoro-3-trifluoromethylphenyl)guanidine; N-(1-naphthyl)-N'-(4-fluoro-3-ethylphenyl)guanidine; N-(7-fluoronaphthyl)-N'-(3-ethylphenyl)guanidine; N-(4-fluoronaphthyl)-N'-(4-fluoro-3-ethylphenyl)guanidine; N-(4-fluoronaphthyl)-N'-(2-isopropylphenyl)guanidine; N-(7-fluoronaphthyl)-N'-(2-isopropylphenyl)guanidine; N-(1-naphthyl)-N'-(4-fluoro-2-isopropylphenyl)guanidine; N-(4-fluoronaphthyl)-N'-(4-fluoro-2-isopropylphenyl)guanidine; N-(4-fluoronaphthyl)-N'-(6-methoxy-3-ethylphenyl)guanidine; N-(7-fluoronaphthyl)-N'-(6-methoxy-3-ethylphenyl)guanidine; N-(4-fluoronaphthyl)-N'-(6-methoxy-4-fluoro-3-ethyl)guanidine; N-(4-fluoronaphthyl)-N'-(4-fluoro-3-tolyl)guanidine; N-(7-fluoronaphthyl)-N'-(4-fluoro-3-tolyl)guanidine; N-(4-fluoronaphthyl)-N'-(4-fluoro-3-trifluoromethylphenyl)guanidine; N-(1-naphthyl)-N'-(4-fluoro-3-trifluoromethylphenyl)guanidine; N-(7-fluoronaphthyl)-N'-(4-fluoro-3-trifluoromethylphenyl)guanidine; N-(coumarin-8-yl)-N-(3-ethylphenyl)guanidine; N-(coumarin-8-yl)-N'-(3-tolyl)guanidine; N-(quinolin-8-yl)-N'-(3-ethylphenyl)guanidine; N-(quinolin-8-yl)-N'-(3-tolyl)guanidine; N-(cyclohexyl)-N'-(4-bromo-2-methylphenyl)guanidine; N-(1-naphthyl)-N'-(o-iodophenyl)guanidine; N-(1-naphthyl)-N'-(m-ethylphenyl)guanidine; N-(1-naphthyl)-N'-(o-isopropylphenyl)guanidine; N-(1-naphthyl)-N'-(m-tolylphenyl)guanidine; N-(1-naphthyl)-N'-(o-ethylphenyl)guanidine; N-(1-naphthyl)-N'-(m-isopropylphenyl)guanidine; N-(1-naphthyl)-N'-(m-methoxyphenyl)guanidine; N-(1-naphthyl)-N'-(4-indanylphenyl)guanidine; N-(m-ethylphenyl)-N'-(o-iodophenyl)guanidine; N-(m-ethylphenyl)-N'-(m-ethylphenyl)guanidine; N-(m-ethylphenyl)-N'-(o-isopropylphenyl)guanidine; N-(m-ethylphenyl)-N'-(m- tolylphenyl)guanidine; N-(m-ethylphenyl)-N'-(o-ethylphenyl)guanidine; N-(m-ethylphenyl)-N'-(m-isopropylphenyl)guanidine; N-(m-ethylphenyl)-N'-(m-methoxyphenyl)guanidine; N-(m-ethylphenyl)-N'-(4-indanylphenyl)guanidine; N-(o-ethylphenyl)-N'-(m-tolyl) guanidine; N-(o-ethylphenyl)-N'-(o-iodophenyl)guanidine; N-(o-ethylphenyl)-N'-(o-isopropylphenyl)guanidine; N-(o-ethylphenyl)-N'-(m-isopropylphenyl)guanidine; N-(o-ethylphenyl)-N'-(m-methoxyphenyl)guanidine; N-(o-ethylphenyl)-N'-(4-indanyl)guanidine; N-(o-iodophenyl)-N'-(m-tolyl)guanidine; N-(o-iodophenyl)-N'-(o-isopropylphenyl)guanidine; N-(o-iodophenyl)-N'-(m-isopropylphenyl)guanidine; N-(o-iodophenyl)-N'-(m-isopropylphenyl)guanidine; N-(o-iodophenyl)-N'-(m-methoxyphenyl)guanidine; N-(o-iodophenyl)-N'-(4-indanyl)guanidine; N-(o-isopropylphenyl)-N'-(m-tolyl)guanidine; N-(o-isopropylphenyl)-N'-(m-isopropylphenyl)guanidine; N-(o-isopropylphenyl)-N'-(m-methoxyphenyl)guanidine; N-(o-isopropylphenyl)-N'-(4-indanyl)guanidine; N-(m-isopropylphenyl)-N'-(m-tolyl)guanidine; N-(m-isopropylphenyl)-N'-(m-methoxyphenyl)guanidine; N-(m-isopropylphenyl)-N'-(4-indanyl)guanidine; N-(m-methoxyphenyl)-N'-(m-tolyl)guanidine; N-(m-methoxyphenyl)-N'-(4-indanyl)guanidine; N-(4-indanyl)-N'-(m-tolyl)guanidine; N-(2-methylazidophenyl)-N'-(2-methylphenyl)guanidine; N-adamantyl-N'-(2-methylphenyl)guanidine; N-(iodophenyl)-N'-(2-methylphenyl)guanidine; N-(2-methyl-4-nitrophenyl)-N'-(2-methylphenyl)guanidine; N-(2-iodophenyl)-N'-(adamantyl)guanidine; N-(2-methylphenyl)-N'-(cyclohexyl) guanidine; N-adamantyl-N'-phenylguanidine; N-(3,5-dimethyl-1-adamantyl)-N'-(o-tolyl)guanidine; N-(3,5-dimethyl-1-adamantyl)-N'-(o-iodophenyl)guanidine; N-(1-adamantyl)-N'-(o-nitrophenyl)guanidine; N-(exo-2-isobornyl)-N'-(o-iodophenyl)guanidine; N-(exo-2-isobornyl)-N'-(o-tolyl)guanidine; N-(o-iodophenyl)-N'-(t-butyl)guanidine; N-(adamant-1-yl)-N'-(o-isopropylphenyl) guanidine; N-(adamant-1-yl)-N'-(p-bromo-o-tolyl) guanidine; N-(cyclohexyl)-N'-(p-bromo-o-tolyl)guanidine; N-(adamant-2-yl)-N'-(p-iodophenyl)guanidine; N-(adamantan-1-yl)-N'-(2-trifluoromethylphenyl) guanidine; N-(adamantan-1-yl)-N'-(2-methylphenyl)-N'-methylguanidine; N-(adamantan-1-yl)-N'-(6-coumarinyl) guanidine; N-(adamantan-1-yl)-N'-(8-coumarinyl) guanidine; N-(adamantan-1-yl)-N'-(2,4-difluorophenyl) guanidine; and N-(adamantan-1-yl)-N'-(2-trifluoromethyl-4-fluorophenyl)guanidine; and pharmaceutically acceptable salts of said compounds.

3. A method for treating decreased blood flow or nutrient supply to retinal tissue or optic nerve, or retinal ischemia or trauma, or optic nerve injury, comprising administering to a mammal in need of such treatment an effective amount of a compound of the following Formula III:

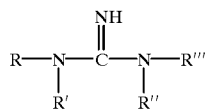

III wherein R, R', R" and R'" are independently a $C_1$–$C_8$ alkyl group, a $C_2$–$C_8$ alkenyl group, $C_2$–$C_6$ alkynyl group, cycloalkyl group, cycloalkyl group substituted by one or more substituents, cycloalkenyl group, cycloalkenyl group substituted with one or more substituents, carbocyclic aryl group, carbocyclic aryl group substituted by one or more substituents, alkaryl group, alkaryl group substituted by one or more substituents, heterocyclic group, heterocyclic group substituted by one or more substituents, heteroaryl group, or a heteroaryl group substituted by one or more substituents;

or a physiologically acceptable salt thereof;

wherein said substituent is chloro, fluoro, bromo, iodo, $C_1$–$C_8$ alkyl, $C_1$–$C_8$ alkoxy, cyano, $C_3$–$C_{15}$ dialkylaminoalkyl, carboxy, carboxamido, $C_1$–$C_8$ alkylthio, allyl, aralkyl, alkaryl, $C_3$–$C_6$ cycloalkyl, aroyl, aralkoxy, $C_2$–$C_8$ acyl, aryl, heteroaryl, an aryl fused to a benzene ring, a heteroaryl fused to a benzene ring, $C_3$–$C_6$ heterocycloalkyl, a $C_3$–$C_6$ heterocycloalkyl ring fused to a benzene ring, $C_1$–$C_8$ alkylsulfonyl, arylthio, amino, $C_1$–$C_8$ alkylamino, $C_2$–$C_{15}$ dialkylamino, hydroxy, hydroxyalkyl, carbamoyl, $C_1$–$C_8$ N-alkylcarbamoyl, $C_2$–$C_{15}$ N,N'-dialkylcarbamoyl, nitro, azido or a $C_2$–$C_{15}$ dialkylsulfamoyl.

4. The method of claim 3 wherein the compound is N,N'-diethyl-N,N'-di-(m-ethylphenyl)guanidine; N,N'-diethyl-N,N'-di-(1-naphthyl)guanidine; N,N'-diethyl-N-(m-ethylphenyl)-N'-(4-indanyl)guanidine; N,N'-diethyl-N-(m-ethylphenyl)-N'-(4-indenyl)guanidine; N,N'-diethyl-N-(m-ethylphenyl)-N'-(o-iodophenyl)guanidine; N,N'-diethyl-N-(m-ethylphenyl)-N'-(o-isopropylphenyl)guanidine; N,N'-diethyl-N-(m-ethylphenyl)-N'-(1-naphthyl)guanidine; N,N'-diethyl-N-(1-naphthyl)-N'-(m-ethylphenyl)guanidine; N,N'-diethyl-N-(m-methylphenyl)-N'-(m-ethylphenyl)guanidine; N,N'-diisopropyl-N,N'-di-(m-ethylphenyl)guanidine; N,N'-diisopropyl-N-(m-ethylphenyl)-N'-(4-indanyl)guanidine; N,N'-diisopropyl-N-(m-ethylphenyl)-N'-(4-indenyl) guanidine; N,N'-diisopropyl-N-(m-ethylphenyl)-N'-(o-iodophenyl)guanidine; N,N'-diisopropyl-N-(m-ethylphenyl)-N'-(o-isopropylphenyl)guanidine; N,N'-diisopropyl-N-(m-ethylphenyl)-N'-(1-naphthyl)guanidine; N,N'-diisopropyl-N-(m-ethylphenyl)-N'-(m-methylphenyl) guanidine; N,N'-dimethyl-N,N'-di-(m-ethylphenyl) guanidine; N,N'-dimethyl-N-(m-ethylphenyl)-N'-(4-indanyl)guanidine; N,N'-dimethyl-N-(m-ethylphenyl)-N'-(4-indenyl)guanidine; N,N'-dimethyl-N-(m-ethylphenyl)-N'-(o-iodophenyl)guanidine; N,N'-dimethyl-N-(m-ethylphenyl)-N'-(o-isopropylphenyl)guanidine; N,N'-dimethyl-N-(m-ethylphenyl)-N'-(1-naphthyl)guanidine; N,N'-dimethyl-N-(m-ethylphenyl)-N'-(m-methylphenyl) guanidine; N-ethyl-N'-isopropyl-N,N'-di-(m-ethylphenyl) guanidine; N-ethyl-N-(m-ethylphenyl)-N'-(4-indanyl)-N'-isopropylguanidine; N-ethyl-N-(m-ethylphenyl)-N'-(4-indenyl)-N'-isopropylguanidine; N-ethyl-N-(m-ethylphenyl)-N'-(o-iodophenyl)-N'-isopropylguanidine; N-ethyl-N-(m-ethylphenyl)-N'-(o-isopropylphenyl)-N'-isopropylguanidine; N-ethyl-N-(m-ethylphenyl)-N'-(1-naphthyl)-N'-isopropylguanidine; N-ethyl-N-(m-ethylphenyl)-N'-(m-methylphenyl)-N'-isopropylguanidine; N-ethyl-N-(4-indanyl)-N'-(m-ethylphenyl)-N'-isopropylguanidine; N-ethyl-N-(4-indenyl)-N'-(m-ethylphenyl)-N'-isopropylguanidine; N-ethyl-N-(o-iodophenyl)-N'-(m-ethylphenyl)-N'-isopropylguanidine; N-ethyl-N-(o-isopropylphenyl)-N'-(m-ethylphenyl)-N'-isopropylguanidine; N-ethyl-N-(1-naphthyl)-N'-(m-ethylphenyl)-N'-isopropylguanidine; N-ethyl-N-(m-methylphenyl)-N'-(m-ethylphenyl)-N'-isopropylguanidine; N,N'-diisopropyl-N,N'-di-(m-ethylphenyl)guanidine; N,N'- diisopropyl-N-(m-ethylphenyl)-N'-(4-indanyl)guanidine; N,N'-diisopropyl-N-(m-ethylphenyl)-N'-(4-indenyl) guanidine; N,N'-diisopropyl-N-(m-ethylphenyl)-N'-(o-iodophenyl)guanidine; N,N'-diisopropyl-N-(m-ethylphenyl)-N'-(o-isopropylphenyl)guanidine; N,N'-diisopropyl-N-(m-ethylphenyl)-N'-(1-naphthyl)guanidine; N,N'-diisopropyl-N-(m-ethylphenyl)-N'-(m-methylphenyl) guanidine; N,N'-diisopropyl-N-(4-indanyl)-N'-(m-ethylphenyl)guanidine; N,N'-diisopropyl-N-(4-indenyl)-N'-(m-ethylphenyl)guanidine; N,N'-diisopropyl-N-(o-iodophenyl)-N'-(m-ethylphenyl)guanidine; N,N'-diisopropyl-N-(o-isopropylphenyl)-N'-(m-ethylphenyl) guanidine; N,N'-diisopropyl-N-(1-naphthyl)-N'-(m-ethylphenyl)guanidine; N,N'-diisopropyl-N-(m-methylphenyl)-N'-(m-ethylphenyl)guanidine; N-methyl-N,N'-di-(m-ethylphenyl)-N'-isopropylguanidine; N-methyl-N-(m-ethylphenyl)-N'-(4-indanyl)-N'-isopropylguanidine; N-methyl-N-(m-ethylphenyl)-N'-(4-indenyl)-N'-isopropylguanidine; N-methyl-N-(m-ethylphenyl)-N'-(o-iodophenyl)-N'-isopropylguanidine; N-methyl-N-(m-ethylphenyl)-N'-(o-isopropylphenyl)-N'-isopropylguanidine; N-methyl-N-(m-ethylphenyl)-N'-(1-naphthyl)-N'-isopropylguanidine; N-methyl-N-(m-ethylphenyl)-N'-(m-methylphenyl)-N'-isopropylguanidine; N-methyl-N-(4-indanyl)-N'-(m-ethylphenyl)-N'-isopropylguanidine; N-methyl-N-(4-indenyl)-N'-(m-ethylphenyl)-N'-isopropylguanidine; N-methyl-N-(o-iodophenyl)-N'-(m-ethylphenyl)-N'-isopropylguanidine; N-methyl-N-(o-isopropylphenyl)-N'-(m-ethylphenyl)-N'-isopropylguanidine; N-methyl-N-(1-naphthyl)-N'-(m-ethylphenyl)-N'-isopropylguanidine; N-methyl-N-(m-methylphenyl)-N'-(m-ethylphenyl)-N'-isopropylguanidine; N-ethyl-N,N'-di-(m-ethylphenyl)-N'-methylguanidine; N-ethyl-N-(m-ethylphenyl)-N'-(4-indanyl)-N'-methylguanidine; N-ethyl-N-(m-ethylphenyl)-N'-(4-indenyl)-N'-methylguanidine; N-ethyl-N-(m-ethylphenyl)-N'-(o-iodophenyl)-N'-methylguanidine; N-ethyl-N-(m-ethylphenyl)-N'-(o-isopropylphenyl)-N'-methylguanidine; N-ethyl-N-(m-ethylphenyl)-N'-(1-naphthyl)-N'-methylguanidine; N-ethyl-N-(m-ethylphenyl)-N'-(m-methylphenyl)-N'-methylguanidine; N,N'-di(1-naphthyl)-N,N'-dimethylguanidine; N-(8-coumarinyl)-N'-(3-ethylphenyl)-N,N'-dimethylguanidine; N,N'-di(8-coumarinyl)-N,N'-dimethylguanidine; N,N'-di(8-coumarinyl)-N-methyl-N'-ethylguanidine; N-(1-naphthyl)-N'-(3-nitrophenyl)-N,N'-dimethylguanidine; N-(1-naphthyl)-N'-(3-azidophenyl)-N,N'-dimethylguanidine; N-(8-coumarinyl)-N'-(3-nitrophenyl)-N,N'-dimethylguanidine; N-(8-coumarinyl)-N'-(3-azidophenyl)-N,N'-dimethylguanidine; N-(7-fluoro-1-naphthyl)-N'-(3-ethylphenyl)-N,N'-dimethylphenylguanidine; N-(4-fluoro-1-naphthyl)-N'-(3-ethylphenyl)-N,N'-dimethylguanidine; N-(1-naphthyl)-N'-(4-fluoro-3-ethylphenyl-N,N'-dimethylguanidine; N-(1-naphthyl)-N'-(3-methylphenyl)-N,N'-dimethylguanidine; N-(8-coumarinyl)-N-(3-methylphenyl)-N,N'-dimethylguanidine; N-(1-naphthyl)-N'-(3-nitrophenyl)-N,N'-diethylguanidine; N-(1-naphthyl)-N'-(3-azidophenyl)-N,N'-diethylguanidine; N-(8-coumarinyl)-N'-(3-nitrophenyl)-N,N'-diethylguanidine; N-(8-coumarinyl)-N'-(3-azidophenyl)-N,N'-diethylguanidine; N-(7-fluoro-1-naphthyl)-N'-(3-ethylphenyl)-N,N'-diethylphenylguanidine; N-(4-fluoro-1-naphthyl)-N'-(3-ethylphenyl)-N,N'-diethylguanidine; N-(1-naphthyl)-N'-(4-fluoro-3-ethylphenyl)-N,N'-diethylguanidine; N-(1-naphthyl)-N'-(3-methylphenyl)-N,N'-diethylguanidine; and N-(8-coumarinyl)-N-(3-methylphenyl)-N,N'-diethylguanidine.

5. A method for treating decreased blood flow or nutrient supply to retinal tissue or optic nerve, or retinal ischemia or trauma, or optic nerve injury, comprising administering to a mammal in need of such treatment an effective amount of a compound of the following Formula IV:

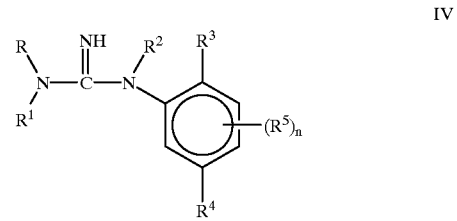

IV wherein R, $R^1$ and $R^2$ are each independently hydrogen, substituted or unsubstituted alkyl, substituted or unsubstituted alkenyl, substituted or unsubstituted alkynyl, substituted or unsubstituted alkoxy, substituted or unsubstituted alkylthio, substituted or unsubstituted alkylsulfinyl, substituted or unsubstituted alkylsulfonyl, substituted or unsubstituted aminoalkyl, substituted or unsubstituted carbocyclic aryl, substituted or unsubstituted aralkyl, or a substituted or unsubstituted heteroaromatic or heteroalicyclic group having 1 to 3 rings, 3 to 8 ring members in each ring and 1 to 3 heteroatoms;

$R^3$, $R^4$, and each $R^5$ substituent are each independently halogen, hydroxyl, azido, substituted or unsubstituted alkyl, substituted or unsubstituted alkenyl, substituted or unsubstituted alkynyl, substituted or unsubstituted alkoxy, substituted or unsubstituted alkylthio, substituted or unsubstituted alkylsulfinyl, substituted or unsubstituted alkylsulfonyl, substituted or unsubstituted aminoalkyl, substituted or unsubstituted carbocyclic aryl, substituted or unsubstituted aralkyl, nitro, cyano, substituted or unsubstituted alkanoyl, or substituted or unsubstituted carboxy; n is an integer of from 0 to 3; or a pharmaceutically acceptable salt thereof.

6. The method of claim 5 wherein the compound is N-(3-ethylphenyl)-N,N'-dimethyl-N'-(2,5-dichlorophenyl) guanidine; N-(3-ethylphenyl)-N-methyl-N'-(2,5-dichlorophenyl)guanidine; N-(3-ethylphenyl)-N'-(2,5-dichlorophenyl)-N'-methylguanidine; N-(3-ethylphenyl)-N'-(2,5-dichlorophenyl)guanidine; N-(3-ethylphenyl)-N-methyl-N'-(2,5-dibromophenyl)guanidine; N-(3-ethylphenyl)-N'-(2,5-dibromophenyl)-N'-methylguanidine; N-(3-ethylphenyl)-N'-(2,5-dibromophenyl)guanidine; N-(3-ethylphenyl)-N-methyl-N'-(2-chloro-5-trifluromethylphenyl)guanidine; N-(3-ethylphenyl)-N'-(2-chloro-5-trifluoromethylphenyl)guanidine; N-(3-ethylphenyl)-N,N'-dimethyl-N'-(2-bromo-5-trifluoromethyl)guanidine; N-(3-ethylphenyl)-N-methyl-N'-(2-bromo-5-trifluromethylphenyl)guanidine; N-(3-ethylphenyl)-N'-(2-bromo-5-trifluoromethylphenyl) guanidine; N-(3-ethylphenyl)-N-methyl-N'-(2-fluoro-5-trifluromethylphenyl)guanidine; N-(3-ethylphenyl)-N'-(2-fluoro-5-trifluoromethylphenyl)guanidine; N-(3-ethylphenyl)-N,N'-dimethyl-N'-(2-chloro-5-ethylphenyl) guanidine; N-(3-ethylphenyl)-N-methyl-N'-(2-chloro-5-ethylphenyl)guanidine; N-(3-ethylphenyl)-N'-(2-chloro-5-ethylphenyl)guanidine; N-(3-ethylphenyl)-N,N'-dimethyl-N'-(2-bromo-5-ethylphenyl)guanidine; N-(3-ethylphenyl)-N-methyl-N'-(2-bromo-5-ethylphenyl)guanidine; N-(3-ethylphenyl)-N'-(2-bromo-5-ethylphenyl)guanidine; N-(3-ethylphenyl)-N,N'-dimethyl-N'-(2-fluoro-5-ethylphenyl) guanidine; N-(3-ethylphenyl)-N-methyl-N'-(2-fluoro-5-ethylphenyl)guanidine; N-(3-ethylphenyl)-N'-(2-fluoro-5- ethylphenyl)guanidine; N-(3-ethylphenyl)-N,N'-dimethyl-N'-(2-chloro-5-methylphenyl); N-(3-ethylphenyl)-N-methyl-N'-(2-chloro-5-methylphenyl)guanidine; N-(3-ethylphenyl)-N'-(2-chloro-5-ethylphenyl)guanidine; N-(3-ethylphenyl)-N'-(2-chloro-5-methylphenyl)guanidine; N-(3-ethylphenyl)-N-methyl-N'-(2-chloro-5-methylthio)guanidine; N-(3-ethylphenyl)-N'-(2-chloro-5-methylthio)guanidine; N-(1-naphthyl)-N'-(2-bromo-5-ethylphenyl)guanidine; N-(1-naphthyl-N'-(2-fluoro-5-ethylphenyl)guanidine; N-(1-naphthyl)-N'-(2,5-dichlorophenyl)guanidine; N-(1-naphthyl)-N'-(2-fluoro-5-methylphenyl)guanidine; N-(3-ethylphenyl)-N-methyl-N'-(2,4,5-trichlorophenyl)guanidine; N-(3-ethylphenyl)-N'-(2,4,5-trichlorophenyl)guanidine; N-(3-ethylphenyl)-N-methyl-N'-(2,3,5-trichlorophenyl)guanidine; N-(3-ethylphenyl)-N'-(2,3,5-trichlorophenyl)guanidine; N-(1-naphthyl)-N'-(2,4,5-trichlorophenyl)guanidine; N-(1-naphthyl)-N'-(2,3,5-trichlorophenyl)guanidine; N-(1-naphthyl)-N'-(2,5-dichlorophenyl)-N'-methylguanidine; N-(1-naphthyl)-N'-(2-chloro-5-methylphenyl)guanidine; N-(1-naphthyl)-N'-(2,5-dimethylphenyl)guanidine; N-(1-naphthyl)-N'-(2,5-dibromophenyl)guanidine; N-(1-naphthyl)-N'-(2-chloro-5-methylphenyl)-N'-methylguanidine; N-(1-naphthyl)-N'-(2-5-dimethylphenyl)-N'-methylguanidine; N-(1-naphthyl)-N'-(2,5-dibromophenyl)-N-methylguanidine; N-(1-naphthyl)-N'-(2,5-dibromophenyl)-N'-methylguanidine; N-(1-naphthyl)-N'-(2-chloro-5-thiomethylphenyl)guanidine; N-(1-naphthyl)-N'-(2-fluoro-5-trifluoromethylphenyl)guanidine; N-(1-naphthyl)-N'-(2-chloro-5-trifluoromethylphenyl)guanidine; N-(1-naphthyl)-N'-(2-bromo-5-trifluoromethylphenyl)guanidine; N-(1-naphthyl)-N'-(2-thiomethyl-5-trifluoromethylphenyl)guanidine; N-(1-naphthyl)-N'-(2-methoxy-5-methylphenyl)guanidine; N-(1-naphthyl)-N'-(2-chloro-5-ethylphenyl)guanidine; N-(1-naphthyl)-N'-(2-chloro-5-ethylphenyl)-N'-methylguanidine; N-(1-naphthyl)-N'-methyl-N'-(2-chloro-5-thiomethylphenyl)guanidine; N-(8-quinolinyl)-N'-(2-chloro-5-methylphenyl)guanidine; N-(8-quinolinyl)-N'-(2-chloro-5-ethylphenyl)guanidine; N-(8-quinolinyl)-N'-methyl-(2-chloro-5-ethylphenyl)guanidine; N-(3-methylthiophenyl)-N-methyl-N'-(2-chloro-5-methylthiophenyl)guanidine; N-(3-methylthiophenyl)-N'-methyl-N'-(2-chloro-5-methylthiophenyl)guanidine; N-(3-methylthiophenyl)-N'-(2-chloro-5-methylthiophenyl)guanidine; N-(3-methylthiophenyl)-N-methyl-N'-(2-chloro-5-ethylphenyl)guanidine; N-(3-methylthiophenyl)-N'-methyl-N'-(2-chloro-5-ethylphenyl)guanidine; N-(3-methylthiophenyl)-N'-(2-chloro-5-ethylphenyl)guanidine; N-(3-methylthiophenyl)-N-methyl-N'-(2-bromo-5-ethylphenyl)guanidine; N-(3-methylthiophenyl)-N'-methyl-N'-(2-bromo-5-ethylphenyl)guanidine; N-(3-methylthiophenyl)-N'-(2-bromo-5-ethylphenyl)guanidine; N-(3-methylthiophenyl-N-methyl-N'-(2,5-dichlorophenyl)guanidine; N-(3-methylthiophenyl-N'-methyl-N'-(2,5-dichlorophenyl)guanidine; N-(3-methylthiophenyl)-N'-(2,5-dichlorophenyl)guanidine; N-(3-methylthiophenyl)-N-methyl-N'-(2,5-dibromophenyl)guanidine; N-(3-methylthiophenyl)-N'-methyl-N'-(2,5-dibromophenyl)guanidine; N-(3-methylthiophenyl)-N'-(2,5-dibromophenyl)guanidine; N-(3-trifluoromethylphenyl)-N-methyl-N'-(2-chloro-5-methylthiophenyl)guanidine; N-(3-trifluoromethylphenyl)-N'-methyl-N'-(2-chloro-5-methylthiophenyl)guanidine; N-(3-trifluoromethylphenyl)-N'-(2-chloro-5-methylthiophenyl)guanidine; N-(3-trifluoromethylphenyl)-N-methyl-N'-(2-chloro-5-ethylphenyl)guanidine; N-(3-trifluoromethylphenyl)-N'-methyl-N'-(2-chloro-5-ethylphenyl)guanidine; N-(3-trifluoromethylphenyl)-N'-(2-chloro-5-ethylphenyl)guanidine; N-(3-trifluoromethylphenyl)-N-methyl-N'-(2-bromo-5-ethylphenyl)guanidine; N-(3-trifluoromethylphenyl)-N'-methyl-N'-(2-bromo-5- ethylphenyl)guanidine; N-(3-trifluoromethylphenyl)-N'-(2-bromo-5-ethylphenyl)guanidine; N-(3-trifluoromethylphenyl)-N-methyl-N'-(2,5-dichlorophenyl)guanidine; N-(3-trifluoromethylphenyl)-N'-methyl-N'-(2,5-dichlorophenyl)guanidine; N-(3-trifluoromethylphenyl)-N'-(2,5-dichlorophenyl)guanidine; N-(3-trifluoromethylphenyl)-N-methyl-N'-(2,5-dibromophenyl)guanidine; N-(3-trifluoromethylphenyl)-N'-methyl-N'-(2,5-dibromophenyl)guanidine; N-(3-trifluoromethylphenyl)-N'-(2,5-dibromophenyl)guanidine; N-(3-ethylphenyl)-N-methyl-N'-(2-bromo-5-methylthiophenyl)guanidine; N-(3-ethylphenyl)-N'-methyl-N'-(2-bromo-5-methylthiophenyl)guanidine; N-(3-ethylphenyl)-N'-(2-bromo-5-methylthiophenyl)guanidine; N-(3-methylthiophenyl)-N-methyl-N'-(2-bromo-5-methylthiophenyl)guanidine; N-(3-methylthiophenyl)-N'-methyl-N'-(2-bromo-5-methylthiophenyl)guanidine; N-(3-methylthiophenyl)-N'-(2-bromo-5-methylthiophenyl)guanidine; N-(3-methylthiophenyl)-N-methyl-N'-(2-bromo-5-ethylphenyl)guanidine; N-(3-methylthiophenyl)-N'-methyl-N'-(2-bromo-5-ethylphenyl)guanidine; N-(3-methylthiophenyl)-N'-(2-bromo-5-ethylphenyl)guanidine; N-(3-trifluoromethylphenyl)-N-methyl-N'-(2-bromo-5-methylthiophenyl)guanidine; N-(3-trifluoromethylphenyl)-N'-methyl-N'-(2-bromo-5-methylthiophenyl)guanidine; N-(3-trifluoromethylphenyl)-N'-(2-bromo-5-methylthiophenyl)guanidine; N-(3-bromophenyl)-N-methyl-N'-(2-chloro-5-methylthiophenyl)guanidine; N-(3-bromophenyl)-N'-methyl-N'-(2-chloro-5-methylthiophenyl)guanidine; N-(3-bromophenyl)-N'-(2-chloro-5-methylthiophenyl)guanidine; N-(3-trifluoromethoxyphenyl)-N-methyl-N'-(2,5-dibromophenyl)guanidine; N-(3-trifluoromethoxyphenyl)-N'-methyl-N'-(2,5-dibromophenyl)guanidine; N-(3-trifluoromethoxyphenyl)-N'-(2,5-dibromophenyl)guanidine; N-(3-trifluoromethoxyphenyl)-N-methyl-N'-(2-bromo-5-ethylphenyl)guanidine; N-(3-trifluoromethoxyphenyl)-N'-methyl-N'-(2-bromo-5-ethylphenyl)guanidine; N-(3-trifluoromethoxyphenyl)-N'-(2-bromo-5-ethylphenyl)guanidine; N-(3-iodophenyl)-N-methyl-N'-(2-chloro-5-methylthiophenyl)guanidine; N-(3-iodophenyl)-N'-methyl-N'-(2-chloro-5-methylthiophenyl)guanidine; N-(3-iodophenyl)-N'-(2-chloro-5-methylthiophenyl)guanidine; N-(3-iodophenyl)-N-methyl-N'-(2-chloro-5-ethylphenyl)guanidine; N-(3-iodophenyl)-N'-methyl-N'-(2-chloro-5-ethylphenyl)guanidine; N-(3-iodophenyl)-N'-(2-chloro-5-ethylphenyl)guanidine; N-(3-ethylphenyl)-N'-(2-chloro-5-ethylthiophenyl)guanidine; N-(3-ethylphenyl)-N-methyl-N'-(2-chloro-5-ethylthiophenyl)guanidine; N-(3-ethylphenyl)-N'-methyl-N'-(2-chloro-5 -ethylthiophenyl)guanidine; N-(3-ethylphenyl)-N,N'-dimethyl-N'-(2-chloro-5-ethylthiophenyl)guanidine; N-(3-ethylphenyl)-N'-(2-bromo-5-ethylthiophenyl)guanidine; N-(3-ethylphenyl)-N-methyl-N'-(2-bromo-5-ethylthiophenyl)guanidine; N-(3-ethylphenyl)-N'-methyl-N'-(2-bromo-5-ethylthiophenyl)guanidine; N-(3-ethylphenyl)-N,N'-dimethyl-N'-(2-bromo-5-ethylthiophenyl)guanidine; N-(3-methylthiophenyl)-N'-(2-chloro-5-ethylthiophenyl)guanidine; N-(3-methylthiophenyl)-N-methyl-N'-(2-chloro-5-ethylthiophenyl)guanidine; N-(3-methylthiophenyl)-N'-methyl-N'-(2-chloro-5-ethylthiophenyl)guanidine; N-(3-methylthiophenyl)-N,N'-dimethyl-N'-(2-chloro-5-ethylthiophenyl)guanidine; N-(3-methylthiophenyl)-N'-(2-bromo-5-ethylthiophenyl)guanidine; N-(3-methylthiophenyl)-N-methyl-N'-(2-bromo-5-ethylthiophenyl)guanidine; N-(3-methylthiophenyl)-N'-methyl-N'-(2-bromo-5-ethylthiophenyl)guanidine; N-(3-methylthiophenyl)-N,N'-dimethyl-N'-(2-bromo-5-ethylthiophenyl)guanidine; N-(3-trifluoromethylphenyl)-N'-(2-chloro-5-ethylthiophenyl)guanidine; N-(3-trifluoromethylphenyl)-N-methyl-N'-(2-chloro-5- ethylthiophenyl)guanidine; N-(3-trifluoromethylphenyl)-N'-methyl-N'-(2-chloro-5-ethylthiophenyl)guanidine; N-(3-trifluoromethylphenyl)-N,N'-dimethyl-N'-(2-chloro-5-ethylthiophenyl)guanidine; N-(3-trifluoromethylphenyl)-N'-(2-bromo-5-ethylthiophenyl)guanidine; N-(3-trifluoromethylphenyl)-N-methyl-N'-(2-bromo-5-ethylthiophenyl)guanidine; N-(3-trifluoromethylphenyl)-N'-methyl-N'-(2-bromo-5-ethylthiophenyl)guanidine; N-(3-trifluoromethylphenyl)-N,N'-dimethyl-N'-(2-bromo-5-ethylthiophenyl)guanidine; N-(3-ethylphenyl)-N'-(2-chloro-5-trifluoromethylthiophenyl)guanidine; N-(3-ethylphenyl)-N-methyl-N'-(2-chloro-5-trifluoromethylthiophenyl)guanidine; N-(3-ethylphenyl)-N'-methyl-N'-(2-chloro-5-trifluoromethylthiophenyl)guanidine; N-(3-ethylphenyl)-N,N'-dimethyl-N'-(2-chloro-5-trifluoromethylthiophenyl)guanidine; N-(3-ethylphenyl)-N'-(2-bromo-5-trifluoromethylthiophenyl)guanidine; N-(3-ethylphenyl)-N-methyl-N'-(2-bromo-5-trifluoromethylthiophenyl)guanidine; N-(3-ethylphenyl)-N'-methyl-N'-(2-bromo-5-trifluoromethyl thiophenyl)guanidine; N-(3-ethylphenyl)-N,N'-dimethyl-N'-(2-bromo-5-trifluoromethyl thiophenyl)guanidine; N-(3-methylthiophenyl)-N'-(2-chloro-5-trifluoromethylthiophenyl)guanidine; N-(3-methylthiophenyl)-N-methyl-N'-(2-chloro-5-trifluoromethylthiophenyl)guanidine; N-(3-methylthiophenyl)-N'-methyl-N'-(2-chloro-5-trifluoromethylthiophenyl)guanidine; N-(3-methylthiophenyl)-N,N'-dimethyl-N'-(2-chloro-5-trifluoromethylthiophenyl)guanidine; N-(3-methylthiophenyl)-N'-(2-bromo-5-trifluoromethylthiophenyl)guanidine; N-(3-methylthiophenyl)-N-methyl-N'-(2-bromo-5-trifluoromethylthiophenyl)guanidine; N-(3-methylthiophenyl)-N'-methyl-N'-(2-bromo-5-trifluoromethylthiophenyl)guanidine; N-(3-methylthiophenyl)-N,N'-dimethyl-N'-(2-bromo-5-trifluoromethylthiophenyl)guanidine; N-(3-trifluoromethylphenyl)-N'-(2-chloro-5-trifluoromethylthiophenyl)guanidine; N-(3-trifluoromethylphenyl)-N-methyl-N'-(2-chloro-5-trifluoromethylthiophenyl)guanidine; N-(3-trifluoromethylphenyl)-N'-methyl-N'-(2-chloro-5-trifluoromethylthiophenyl)guanidine; N-(3-trifluoromethylphenyl)-N,N'-dimethyl-N'-(2-chloro-5-trifluoromethylthiophenyl)guanidine; N-(3-trifluoromethylphenyl)-N'-(2-bromo-5-trifluoromethylthiophenyl)guanidine; N-(3-trifluoromethylphenyl)-N-methyl-N'-(2-bromo-5-trifluoromethylthiophenyl)guanidine; N-(3-trifluoromethylphenyl)-N'-methyl-N'-(2-bromo-5-trifluoromethylthiophenyl)guanidine; N-(3-trifluoromethylphenyl)-N,N'-dimethyl-N'-(2-bromo-5-trifluoromethylthiophenyl)guanidine; N-(1-naphthyl)-N'-(2-chloro-5-methylthiophenyl)guanidine; N-(1-naphthyl)-N'-(2-iodo-5-methylthiophenyl)guanidine; N-(1-naphthyl)-N'-(2-bromo-5-methylthiophenyl)guanidine; N-(3-methylsulfonylphenyl)-N-methyl-N'-(2,5-dibromophenyl)guanidine; N-(3-methylsulfonylphenyl)-N'-(2,5-dibromophenyl)guanidine; N-(3-methylsulfinylphenyl)-N-methyl-N'-(2,5-dibromophenyl)guanidine; N-(3-methylsulfinylphenyl)-N'-(2,5-dibromophenyl)guanidine; or a pharmaceutically acceptable salt thereof.

7. A method for treating decreased blood flow or nutrient supply to retinal tissue, or retinal ischemia or trauma, or optic nerve injury, comprising administering to a mammal in need of such treatment an effective amount of a compound of claim 1, 3, or 5 that has a substituent of carbocyclic aryl substituted at one or more ring positions by haloalkyl, substituted or unsubstituted thioalkyl having from 1 to about 3 carbon atoms, substituted or unsubstituted alkylsulfinyl or substituted or unsubstituted alkylsulfonyl.

8. The method of claim 7 wherein the compound is N-(1-naphthyl)-N'-(3-methylthiophenyl)-N'-methylguanidine; N-(1-naphthyl)-N-methyl-N'-(3-methylthiophenyl)guanidine; N-(1-naphthyl)-N,N'-dimethyl-N'-(3-methylthiophenyl)guanidine; N-(1-naphthyl)-N'-(3-methylthiophenyl)guanidine; N-(1-naphthyl)-N'-(3-methylsulfinylphenyl)-N'-methylguanidine; N-(1-naphthyl)-N-methyl-N'-(3-methylsulfinylphenyl)guanidine; N-(1-naphthyl)-N,N'-dimethyl-N'-(3-methylsulfinylphenyl)guanidine; N-(1-naphthyl)-N'-(3-methylsulfinylphenyl)guanidine; N-(1-naphthyl)-N'-(3-methylsulfonylphenyl)-N'-methylguanidine; N-(1-naphthyl)-N-methyl-N'-(3-methylsulfonylphenyl)guanidine; N-(1-naphthyl)-N,N'-dimethyl-N'-(3-methylsulfonylphenyl)guanidine; N-(1-naphthyl)-N'-(3-methylsulfonylphenyl)guanidine; N-(1-naphthyl)-N'-(3-trifluoromethylthiophenyl)-N'-methylguanidine; N-(1-naphthyl)-N-methyl-N'-(3-trifluoromethylthiophenyl)guanidine; N-(1-naphthyl)-N,N'-dimethyl-N'-(3-trifluoromethylthiophenyl)guanidine; N-(1-naphthyl)-N'-(3-trifluoromethylthiophenyl)guanidine; N-(1-naphthyl)-N'-(3-pentafluoroethylphenyl)-N'-methylguanidine; N-(1-naphthyl)-N-methyl-N'-(3-pentafluoroethylphenyl)guanidine; N-(1-naphthyl)-N,N'-dimethyl-N'-(3-pentafluoroethylphenyl)guanidine; N-(1-naphthyl)-N'-(3-pentafluoroethylphenyl)guanidine; N-(1-naphthyl)-N'-(3-trifluoromethoxyphenyl)-N'-methylguanidine; N-(1-naphthyl)-N-methyl-N'-(3-trifluoromethoxyphenyl)-N'-methylguanidine; N-(1-naphthyl)-N'-(3-trifluoromethoxyphenyl)guanidine; N-(3-ethylphenyl)-N'-(3-methylthiophenyl)-N'-methylguanidine; N-(3-ethylphenyl)-N,N'-dimethyl-N'-(3-methylthiophenyl)guanidine; N-(3-ethylphenyl)-N'-(3-methylthiophenyl)guanidine; N-(3-ethylphenyl)-N'-(3-methylsulfinylphenyl)-N'-methylguanidine; N-(3-ethylphenyl)-N,N'-dimethyl-N'-(3-methylsulfinylphenyl)guanidine; N-(3-ethylphenyl)-N'-(3-methylsulfinylphenyl)guanidine; N-(3-ethylphenyl)-N'-(3-methylsulfonylphenyl)-N'-methylguanidine; N-(3-ethylphenyl)-N,N'-dimethyl-N'-(3-methylsulfonylphenyl)guanidine; N-(3-ethylphenyl)-N'-(3-methylsulfonylphenyl)guanidine; N-(3-ethylphenyl)-N'-(3-trifluoromethylthiophenyl)-N'-methylguanidine; N-(3-ethylphenyl)-N-methyl-N'-(3-trifluoromethylthiophenyl)guanidine; N-(3-ethylphenyl)-N,N'-dimethyl-N'-(3-trifluoromethylthiophenyl)guanidine; N-(3-ethylphenyl)-N'-(3-trifluoromethylthiophenyl)guanidine; N-(3-ethylphenyl)-N'-(3-pentafluoroethylphenyl)-N'-methylguanidine; N-(3-ethylphenyl)-N-methyl-N'-(3-pentafluoroethylphenyl)guanidine; N-(3-ethylphenyl)-N-methyl-N'-(3-pentafluoroethylphenyl)-N'-methylguanidine; N-(3-ethylphenyl)-(3-pentafluoroethylphenyl)guanidine; N-(3-ethylphenyl)-N'-(3-trifluoromethylphenyl)-N'-methylguanidine; N-(3-ethylphenyl)-N-methyl-N'-(3-trifluoromethoxyphenyl)guanidine; N-(3-ethylphenyl)-N-methyl-N'-(3-trifluoromethoxyphenyl)-N'-methylguanidine; N-(3-ethylphenyl)-N-methyl-N'-(3-trifluoromethoxyphenyl)guanidine; N-(3-ethylphenyl)-N'-(3-trifluoromethoxyphenyl)guanidine; N-(3-methylthiophenyl)-N'-(3-methylthiophenyl)guanidine; N-(3-methylthiophenyl)-N'-(3-methylthiophenyl)-N'-methylguanidine; N-(3-methylthiophenyl)-N-methyl-N'-(3-methylthiophenyl)guanidine; N-(3-methylthiophenyl)-N,N'-dimethyl-N'-(3-methylthiophenyl)guanidine; N-(3-methylthiophenyl)-N'-(3-bromophenyl)guanidine; N-(3-methylthiophenyl)-N'-(3-bromophenyl)-N'-methylguanidine; N-(3-methylthiophenyl)-N-methyl-N'-(3-bromophenyl)guanidine; N-(3-methylthiophenyl)-N,N'- dimethyl-N'-(3-bromophenyl)guanidine; N-(3-ethylphenyl)-N,N'-dimethyl(3-trifluoromethylphenyl)guanidine; N-(3-ethylphenyl)-N-methyl-N'-(3-trifluoromethylphenyl)guanidine; N-(3-ethylphenyl)-N'-(3-trifluoromethylphenyl)-N'-methylguanidine; N-(1-naphthyl)-N'-(3-trifluoromethylphenyl)-N-methylguanidine; or N-(1-naphthyl)-N'-(3-trifluoromethylphenyl)-N,N'-dimethylguanidine; or a pharmaceutically acceptable salts thereof.

9. A method for treating decreased blood flow or nutrient supply to retinal tissue or optic nerve, or retinal ischemia or trauma, or optic nerve injury, comprising administering to a mammal in need of such treatment an effective amount of a compound of the following Formula V:

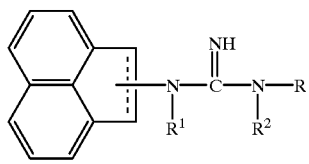

V wherein R is cycloalkyl; carbocyclic aryl; alkaryl; aralkyl or heterocyclic; $R^1$ and $R^2$ are the same or different and selected from the group consisting of hydrogen, lower $C_{1-6}$ alkyl, lower $C_{1-6}$ alkylamino, $C_{5-10}$ aryl or substituted aryl;

wherein R and the acenaphthyl group are optionally substituted by hydroxy, acetate, oxo, amino, lower $C_{1-6}$ alkyl, lower $C_{1-6}$ alkyl amino, alkoxy of 1–6 carbon atoms, di-lower $C_{2-12}$ alkyl amino, nitro, azido, sulfhydryl, cyano, isocyanato, halogen, amido, sulfonato or carbamido; and pharmaceutically acceptable salts thereof.

10. A method for treating decreased blood flow or nutrient supply to retinal tissue, or retinal ischemia or trauma, or optic nerve injury, comprising administering to a mammal in need of such treatment an effective amount of a compound of the following Formula VI:

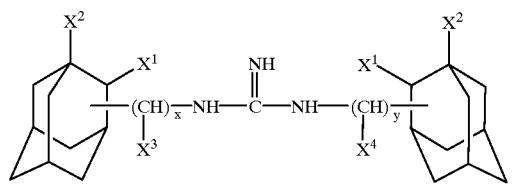

VI wherein $X^1$, $X^2$, $X^3$, and $X^4$ are the same or different and are selected from the group consisting of hydrogen, hydroxy, acetate, oxo, amino, lower $C_{1-6}$ alkyl, lower $C_{1-6}$ alkyl amino, alkoxy of 1–6 carbon atoms, lower $C_{1-6}$ alkyl amino, alkoxy of 1–6 carbon atoms, di-lower $C_{2-12}$ alkyl amino, nitro, azido, sulfhydryl, cyano, isocynato, halogen, amido, sulfonato or carbamido; wherein at least one of $X^1$, $X^2$, $X^3$, and $X^4$ is other than hydrogen; x and y are the same or different and are 0, 1, 2, 3 or 4; and pharmaceutically acceptable salts thereof.

11. A method for treating decreased blood flow or nutrient supply to retinal tissue or optic nerve, or retinal ischemia or trauma, or optic nerve injury, comprising administering to a mammal in need of such treatment an effective amount of a compound of the following Formula VII:

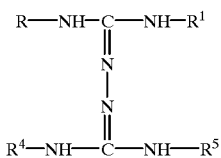

VII or a tautomer thereof, wherein R, $R^1$, $R^4$ and $R^5$ are the same or different and are cycloalkyl; carbocyclic aryl, alkaryl; aralkyl; or heterocyclic;

wherein R, $R^1$, $R^4$ or $R^5$ is optionally substituted hydroxy, acetate, oxo, amino, lower $C_{1-6}$ alkyl, lower $C_{1-6}$ alkyl amino, alkoxy of 1–6 carbon atoms, di-lower $C_{2-12}$ alkyl amino, nitro, azido, sulfhydryl, cyano, isocyanato, halogen, amido, sulfonato or carbamido; or pharmaceutically acceptable salt thereof.

12. A method for treating decreased blood flow or nutrient supply to retinal tissue or optic nerve, or retinal ischemia or trauma, or optic nerve injury, comprising administering to a mammal in need of such treatment an effective amount of a compound of the following Formula:

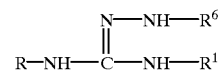

or a tautomer thereof, wherein R and $R^1$ are the same or different and are cycloalkyl; carbocyclic aryl; alkaryl; aralkyl; heterocyclic;

wherein R and $R^1$ are optionally substituted by hydroxy, acetate, oxo, amino, lower $C_{1-6}$ alkyl, lower $C_{1-6}$ alkyl amino, alkoxy of 1–6 carbon atoms, di-lower $C_{2-12}$ alkyl amino, nitro, azido, sulfhydryl, cyano, isocyanato, halogen, amido, sulfonato or carbamido;

$R^6$ is hydrogen, $C_1$–$C_6$ alkyl, $C_3$–$C_{12}$ cycloalkyl, carbocyclic aryl, nitrile, $C_1$–$C_6$ alkoxycarbonyl, $C_1$–$C_6$ acyl or benzoyl; or pharmaceutically acceptable salts thereof.

13. A method for treating decreased blood flow or nutrient supply to retinal tissue or optic nerve, or retinal ischemia or trauma, or optic nerve injury, comprising administering to a mammal in need of such treatment an effective amount of a compound of the following Formula XI:

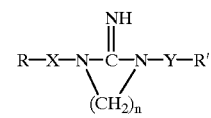

XI wherein n is 2, 3, 4 or 5;

X and Y are independently a single bond, a branched or straight chain $C_1$–$C_{12}$ alkylene or a branched or straight chain alkenylene;

R and R' are independently hydrogen, substituted or unsubstituted a cycloalkyl group of at least 3 carbons, a substituted or unsubstituted carbocyclic group of at least 6 carbon atoms, particularly substituted or unsubstituted phenyl; substituted or unsubstituted aralkyl of at least 6 carbon atoms and containing 1–3 separate or fused rings, or a substituted or unsubstituted heterocyclic or heteroaromatic group having from 1 to 3 rings, 3 to 8 ring members in each ring and 1 to 3 heteroatoms, and wherein each of R and R' may be substituted; or wherein R and R' together with the guanidine nitrogen to which they are attached form a saturated or unsaturated cyclic ring containing at least 2 carbon atoms exclusive of the guanidine carbon atom, and wherein said cyclic ring may be substituted with one or more alkyl groups of 1–6 carbon atoms, carbocyclic aryl or at least 6 carbon atoms, cycloalkyl groups of 3–12 carbon atoms, or 1–2 fused aromatic rings; and pharmaceutically acceptable salts thereof.

14. A method for treating decreased blood flow or nutrient supply to retinal tissue or optic nerve, or retinal ischemia or trauma, or optic nerve injury, comprising administering to a mammal in need of such treatment an effective amount of a compound of the following Formula XII:

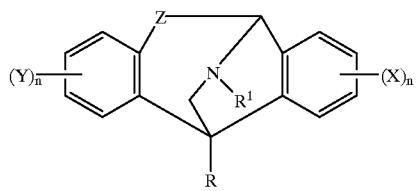

XII wherein:
R is hydrogen, $C_2$–$C_6$ acyl, $C_1$–$C_6$ alkyl, aryl, $C_1$–$C_6$ alkoxycarbonyl, $C_7$–$C_{10}$ aralkyl, $C_2$–$C_6$ alkenyl, $C_3$–$C_{15}$ dialkylaminoalkyl, $C_1$–$C_6$ hydroxyalkyl, $C_2$–$C_6$ alkynyl, $C_3$–$C_{15}$ trialkylsilyl, $C_4$–/$C_{10}$ alkylcycloalkyl, or $C_3$–$C_6$ cycloalkyl;

$R^1$ hydrogen, $C_1$–$C_6$ alkyl, $C_2$–$C_6$ alkenyl, $C_7$–$C_{10}$ aralkyl, $C_1$–$C_6$ alkoxy, $C_1$–$C_6$ alkylamino, or $C_3$–$C_{15}$ dialkylaminoalkyl;

X and Y are independently selected from the group consisting of a halogen such as chloro, fluoro, bromo, iodo, $C_1$–$C_6$ alkoxy, $C_2$–$C_6$ dialkoxymethyl, $C_1$–$C_6$ alkyl, cyano, $C_3$–$C_{15}$ dialkylaminoalkyl, carboxy, carboxamido, $C_1$–$C_6$ haloalkyl, e.g. trifluoromethyl; $C_1$–$C_6$ haloalkylthio, allyl, aralkyl, $C_3$–$C_6$ cycloalkyl, aroyl, aralkoxy, $C_2$–$C_6$ acyl, aryl, substituted aryl, heteroaryl, substituted heteroaryl, $C_3$–$C_6$ heterocycloalkyl, $C_1$–$C_6$ alkylthio, $C_1$–$C_6$ alkylsulfonyl, $C_1$–$C_6$ haloalkylsulfonyl, $C_1$–$C_6$ alkylsulfinyl, $C_1$–$C_6$ haloalkylsulfinyl, arylthio, $C_1$–$C_6$ haloalkoxy, amino, $C_1$–$C_6$ alkylamino, $C_2$–$C_{15}$ dialkylamino, hydroxy, carbamoyl, $C_1$–$C_6$ N-alkylcarbamoyl, $C_2$–$C_{15}$ N,N-dialkylcarbamoyl, nitro and $C_2$–$C_{15}$ dialkylsulfamoyl;

Z represents a group selected from

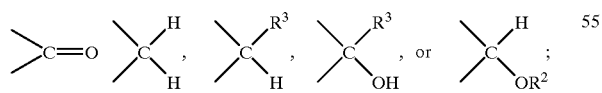

wherein $R^2$ is hydrogen, $C_1$–$C_6$ alkyl, $C_2$–$C_6$ alkenyl, aralkyl, $C_4$–$C_{15}$ dialkylaminoalkyl, heterocycloalkyl, $C_2$–$C_6$ acyl, aroyl, or aralkanoyl, and $R^3$ is $C_1$–$C_6$ alkyl, $C_2$–$C_6$ alkenyl, phenyl, aralkyl or $C_3$–$C_{15}$ dialkylaminoalkyl; and n is an integer selected from 0 (X or Y is hydrogen, respectively), 1, 2, 3 or 4, or a pharmaceutically acceptable salt thereof.

15. A method for treating decreased blood flow or nutrient supply to retinal tissue or optic nerve, or retinal ischemia or trauma, or optic nerve injury, comprising administering to a mammal in need of such treatment an effective amount of a compound of the following Formula XIII:

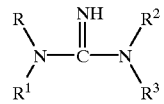

XIII wherein:
R and $R^1$ are each independently substituted or unsubstituted alkyl; substituted or unsubstituted alkenyl; substituted or unsubstituted alkynyl; substituted or unsubstituted alkoxy; substituted or unsubstituted aminoalkyl; substituted or unsubstituted alkylthio; substituted or unsubstituted alkylsulfinyl; substituted or unsubstituted carbocyclic aryl; substituted or unsubstituted aralkyl; or a substituted or unsubstituted heteroaromatic or heteroalicyclic group having from 1 to 3 rings, 3 to 8 ring members in each ring and from 1 to 3 heteroatoms, with at least one of R and $R^1$ being carbocyclic aryl, aralkyl, a heteroaromatic group or a heterocyclic group;

$R^2$ and $R^3$ each being independently selected from the group consisting of hydrogen, substituted and unsubstituted alkyl having from 1 to about 20 carbon atoms, substituted and unsubstituted alkoxy having from 1 to about 20 carbon atoms, substituted and unsubstituted alkylthio having from 1 to about 20 carbon atoms, substituted and unsubstituted alkylsulfinyl having from 1 to about 20 carbon atoms, substituted and unsubstituted alkylsulfonyl having from 1 to about 20 carbon atoms, and substituted and unsubstituted aminoalkyl; and pharmaceutically acceptable salts thereof.

16. A method for treating decreased blood flow or nutrient supply to retinal tissue or optic nerve, or retinal ischemia or trauma, or optic nerve injury, comprising administering to a mammal in need of such treatment an effective amount of a compound of the following Formula XIV:

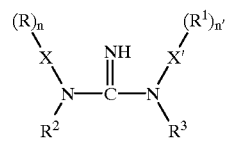

XIV wherein R and $R^1$ are each independently substituted or unsubstituted alkyl having from 1 to about 20 carbon atoms, substituted or unsubstituted alkenyl having from 2 to about 20 carbon atoms, substituted or unsubstituted alkynyl having from 2 to about 20 carbon atoms, substituted or unsubstituted alkoxy having from 1 to about 20 carbon atoms, substituted or unsubstituted aryloxy having from 6 to about 20 carbon atoms, substituted or unsubstituted aralkoxy having from 6 to about 20 carbon atoms, substituted or unsubstituted aminoalkyl having 1 to about 20 carbon atoms, substituted or unsubstituted alkylthio having from 1 to about 20 carbon atoms, substituted or unsubstituted alkylsulfinyl having from 1 to about 20 carbon atoms, substituted or unsubstituted alkylsulfonyl having 1 to about 20 carbon atoms, substituted or unsubstituted carbocyclic aryl having at least 5 ring atoms, substituted or unsubstituted aralkyl having at least 5 ring atoms, or a substituted or unsubstituted heteroaromatic or heteroalicyclic group having 1 to 3 rings, 3 to 8 ring members in each ring and 1 to 3 heteroatoms;

$R^2$ and $R^3$ are each independently hydrogen or a group as defined for R and $R^1$ above, and preferably are each substituted or unsubstituted alkyl, alkenyl, alkynyl, alkoxy, aminoalkyl, alkylthio or alkylsulfinyl; or $R^1$ and $R^3$ together form a ring having 5 or more ring members;

n and n' independently are each equal to 1, 2, or 3;

X and X' are each independently a chemical bond (i.e., a bond between the guanidine nitrogen and R or $R^1$), substituted or unsubstituted alkylene having from 1 to about 8 carbon atoms, substituted or unsubstituted alkenylene having from 2 to about 8 carbon atoms, or substituted or unsubstituted alkynylene having from 2 to about 8 carbon atoms, substituted or unsubstituted heteroalkylene having from 1 to about 8 carbon atoms, substituted or unsubstituted heteroalkenylene having 2 to about 8 carbon atoms, and substituted or unsubstituted heteroalkynylene having from 2 to about 8 carbon atoms, with at least one X and X' being other than a bond; and pharmaceutically acceptable salts thereof.

17. The method of any one of claims 1, 2 and 3–16 wherein the decreased blood flow or nutrient supply is associated with retinal ischemia.

18. The method of claim 17 wherein the retinal ischemia is associated with diabetes, atherosclerosis, venous capillary insufficiency, obstructive arterial or venous retinopathies, senile macular degeneration, cystoid macular edema or glaucoma.

19. The method of claim 17 wherein the retinal ischemia is associated with a tumor or injury to the mammal.

20. The method of any one of claims 1, 2 and 3–16 wherein the mammal has optic nerve injury or damage.

21. A method of claim 1 wherein a mammal is selected that is in need of treatment of decreased blood flow or decreased nutrient supply to retinal tissue or optic nerve, or retinal ischemia or trauma, or optic nerve injury and an effective amount of the compound administered to the selected mammal.

22. A method of claim 3 wherein a mammal is selected that is in need of treatment of decreased blood flow or decreased nutrient supply to retinal tissue or optic nerve, or retinal ischemia or trauma, or optic nerve injury and an effective amount of the compound administered to the selected mammal.

23. A method of claim 4 wherein a mammal is selected that is in need of treatment of decreased blood flow or decreased nutrient supply to retinal tissue or optic nerve, or retinal ischemia or trauma, or optic nerve injury and an effective amount of the compound administered to the selected mammal.

24. A method of claim 5 wherein a mammal is selected that is in need of treatment of decreased blood flow or decreased nutrient supply to retinal tissue or optic nerve, or retinal ischemia or trauma, or optic nerve injury and an effective amount of the compound administered to the selected mammal.

25. A method of claim 6 wherein a mammal is selected that is in need of treatment of decreased blood flow or decreased nutrient supply to retinal tissue or optic nerve, or retinal ischemia or trauma, or optic nerve injury and an effective amount of the compound administered to the selected mammal.

26. A method of claim 9 wherein a mammal is selected that is in need of treatment of decreased blood flow or decreased nutrient supply to retinal tissue or optic nerve, or retinal ischemia or trauma, or optic nerve injury and an effective amount of the compound administered to the selected mammal.

27. A method of claim 10 wherein a mammal is selected that is in need of treatment of decreased blood flow or decreased nutrient supply to retinal tissue or optic nerve, or retinal ischemia or trauma, or optic nerve injury and an effective amount of the compound administered to the selected mammal.

28. A method of claim 11 wherein a mammal is selected that is in need of treatment of decreased blood flow or decreased nutrient supply to retinal tissue or optic nerve, or retinal ischemia or trauma, or optic nerve injury and an effective amount of the compound administered to the selected mammal.

29. A method of claim 12 wherein a mammal is selected that is in need of treatment of decreased blood flow or decreased nutrient supply to retinal tissue or optic nerve, or retinal ischemia or trauma, or optic nerve injury and an effective amount of the compound administered to the selected mammal.

30. A method of claim 13 wherein a mammal is selected that is in need of treatment of decreased blood flow or decreased nutrient supply to retinal tissue or optic nerve, or retinal ischemia or trauma, or optic nerve injury and an effective amount of the compound administered to the selected mammal.

31. A method of claim 14 wherein a mammal is selected that is in need of treatment of decreased blood flow or decreased nutrient supply to retinal tissue or optic nerve, or retinal ischemia or trauma, or optic nerve injury and an effective amount of the compound administered to the selected mammal.

32. A method of claim 15 wherein a mammal is selected that is in need of treatment of decreased blood flow or decreased nutrient supply to retinal tissue or optic nerve, or retinal ischemia or trauma, or optic nerve injury and an effective amount of the compound administered to the selected mammal.

33. A method of claim 16 wherein a mammal is selected that is in need of treatment of decreased blood flow or decreased nutrient supply to retinal tissue or optic nerve, or retinal ischemia or trauma, or optic nerve injury and an effective amount of the compound administered to the selected mammal.

\* \* \* \* \*